US012799525B2

(12) United States Patent
Katsori et al.

(10) Patent No.: US 12,799,525 B2
(45) Date of Patent: Nov. 17, 2026

(54) METHOD FOR TRANSPOSASE MEDIATED SPATIAL TAGGING AND ANALYZING GENOMIC DNA IN A BIOLOGICAL SAMPLE

(71) Applicant: 10x Genomics, Inc., Pleasanton, CA (US)

(72) Inventors: Anna-Maria Katsori, Stockholm (SE); Christina Galonska, Stockholm (SE); Paulius Mielinis, Stockholm (SE); Marlon Stoeckius, Stockholm (SE)

(73) Assignee: 10x Genomics, Inc.

( * ) Notice: Subject to any disclaimer, the term of this patent is extended or adjusted under 35 U.S.C. 154(b) by 933 days.

(21) Appl. No.: 18/074,081

(22) Filed: Dec. 2, 2022

(65) Prior Publication Data

US 2023/0175045 A1 Jun. 8, 2023

Related U.S. Application Data

(60) Provisional application No. 63/285,677, filed on Dec. 3, 2021.

(51) Int. Cl.
*C12Q 1/6837* (2018.01)
*B01D 15/38* (2006.01)
*C12N 15/10* (2006.01)
*C12Q 1/6874* (2018.01)

(52) U.S. Cl.
CPC ....... *C12Q 1/6837* (2013.01); *B01D 15/3809* (2013.01); *C12N 15/1065* (2013.01); *C12Q 1/6874* (2013.01)

(58) Field of Classification Search
None
See application file for complete search history.

(56) References Cited

U.S. PATENT DOCUMENTS 4,683,195 A 7/1987 Mullis
4,683,202 A 7/1987 Mullis
4,800,159 A 1/1989 Mullis
4,883,867 A 11/1989 Lee
4,965,188 A 10/1990 Mullis
4,988,617 A 1/1991 Landegren et al.
5,002,882 A 3/1991 Lunnen
5,130,238 A 7/1992 Malek
5,308,751 A 5/1994 Ohkawa
5,321,130 A 6/1994 Yue
5,410,030 A 4/1995 Yue
5,436,134 A 7/1995 Haugland
5,455,166 A 10/1995 Walker
5,494,810 A 2/1996 Barany et al.
5,503,980 A 4/1996 Cantor
5,512,439 A 4/1996 Hornes
5,512,462 A 4/1996 Cheng
5,582,977 A 12/1996 Yue
5,599,675 A 2/1997 Brenner
5,641,658 A 6/1997 Adams
5,648,245 A 7/1997 Fire et al.
5,658,751 A 8/1997 Yue
5,695,940 A 12/1997 Drmanac et al.
5,750,341 A 5/1998 Macevicz
5,763,175 A 6/1998 Brenner
5,830,711 A 11/1998 Barany et al.
5,837,832 A 11/1998 Chee et al.
5,854,033 A 12/1998 Lizardi
5,863,753 A 1/1999 Haugland
5,871,921 A 2/1999 Landegren et al.
5,912,148 A 6/1999 Eggerding
5,925,545 A 7/1999 Reznikoff et al.
5,928,906 A 7/1999 Koester et al.
5,958,775 A 9/1999 Wickstrrom
5,962,271 A 10/1999 Chenchik et al.
5,962,272 A 10/1999 Chenchik et al.
5,965,443 A 10/1999 Reznikoff et al.
6,013,440 A 1/2000 Lipshutz
6,027,889 A 2/2000 Barany et al.
6,054,274 A 4/2000 Sampson et al.
6,060,240 A 5/2000 Kamb et al.
6,130,073 A 10/2000 Eggerding
6,143,496 A 11/2000 Brown
6,153,389 A 11/2000 Haarer
6,159,736 A 12/2000 Reznikoff et al.
6,165,714 A 12/2000 Lane et al.
6,210,891 B1 4/2001 Nyren (Continued)

FOREIGN PATENT DOCUMENTS

AU 2003200718 10/2006
CN 1273609 11/2000

(Continued)

OTHER PUBLICATIONS

10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
10xGenomics.com, [online], "Visium Spatial Gene Expression Reagent Kits—Tissue Optimization—User Guide," Feb. 2022, retrieved on Mar. 29, 2024, retrieved from URL<https://cdn.10xgenomics.com/image/upload/v1660261286/support-documents/CG000238_VisiumSpatialTissueOptimizationUserGuide_RevE.pdf>, 46 pages.

(Continued)

*Primary Examiner* — Christopher M Gross
(74) *Attorney, Agent, or Firm* — Fish & Richardson P.C.

(57) ABSTRACT

The present disclosure relates to materials and methods for spatially analyzing nucleic acids fragmented with a transposase enzyme, optionally complexed to an antibody-binding moiety (e.g., an antibody-binding protein) bound to an antibody for at least one chromatin protein, in a biological sample.

29 Claims, 11 Drawing Sheets

Specification includes a Sequence Listing.

(56) References Cited

U.S. PATENT DOCUMENTS

| | | | |
|---|---|---|---|
| 6,210,894 | B1 | 4/2001 | Brennan |
| 6,214,587 | B1 | 4/2001 | Dattagupta |
| 6,251,639 | B1 | 6/2001 | Kurn |
| 6,258,568 | B1 | 7/2001 | Nyren |
| 6,266,459 | B1 | 7/2001 | Walt |
| 6,268,148 | B1 | 7/2001 | Barany et al. |
| 6,274,320 | B1 | 8/2001 | Rothberg |
| 6,291,180 | B1 | 9/2001 | Chu |
| 6,291,187 | B1 | 9/2001 | Kingsmore et al. |
| 6,300,063 | B1 | 10/2001 | Lipshutz et al. |
| 6,309,824 | B1 | 10/2001 | Drmanac |
| 6,323,009 | B1 | 11/2001 | Lasken et al. |
| 6,344,316 | B1 | 2/2002 | Lockhart |
| 6,344,329 | B1 | 2/2002 | Lizardi et al. |
| 6,355,431 | B1 | 3/2002 | Chee |
| 6,368,801 | B1 | 4/2002 | Faruqi |
| 6,401,267 | B1 | 6/2002 | Drmanac |
| 6,404,907 | B1 | 6/2002 | Gilchrist |
| 6,432,360 | B1 | 8/2002 | Church et al. |
| 6,503,713 | B1 | 1/2003 | Rana |
| 6,506,561 | B1 | 1/2003 | Cheval et al. |
| 6,534,266 | B1 | 3/2003 | Singer |
| 6,544,732 | B1 | 4/2003 | Chee |
| 6,573,043 | B1 | 6/2003 | Cohen et al. |
| 6,579,695 | B1 | 6/2003 | Lambalot |
| 6,620,584 | B1 | 9/2003 | Chee |
| 6,632,641 | B1 | 10/2003 | Brennan |
| 6,737,236 | B1 | 5/2004 | Pieken et al. |
| 6,770,441 | B2 | 8/2004 | Dickinson |
| 6,773,886 | B2 | 8/2004 | Kaufman |
| 6,787,308 | B2 | 9/2004 | Balasubramanian |
| 6,797,470 | B2 | 9/2004 | Barany et al. |
| 6,800,453 | B2 | 10/2004 | Labaer |
| 6,812,005 | B2 | 11/2004 | Fan et al. |
| 6,828,100 | B1 | 12/2004 | Ronaghi |
| 6,833,246 | B2 | 12/2004 | Balasubramanian |
| 6,852,487 | B1 | 2/2005 | Barany et al. |
| 6,859,570 | B2 | 2/2005 | Walt |
| 6,864,052 | B1 | 3/2005 | Drmanac |
| 6,867,028 | B2 | 3/2005 | Janulaitis |
| 6,872,816 | B1 | 3/2005 | Hall et al. |
| 6,875,572 | B2 | 4/2005 | Prudent et al. |
| 6,890,741 | B2 | 5/2005 | Fan et al. |
| 6,897,023 | B2 | 5/2005 | Fu |
| 6,913,881 | B1 | 7/2005 | Aizenstein et al. |
| 6,942,968 | B1 | 9/2005 | Dickinson et al. |
| 7,011,944 | B2 | 3/2006 | Prudent et al. |
| 7,057,026 | B2 | 6/2006 | Barnes |
| 7,083,980 | B2 | 8/2006 | Reznikoff et al. |
| 7,115,400 | B1 | 10/2006 | Adessi |
| 7,118,883 | B2 | 10/2006 | Inoue |
| 7,166,431 | B2 | 1/2007 | Chee et al. |
| 7,192,735 | B2 | 3/2007 | Lambalot |
| 7,211,414 | B2 | 5/2007 | Hardin |
| 7,255,994 | B2 | 8/2007 | Lao |
| 7,258,976 | B2 | 8/2007 | Mitsuhashi |
| 7,282,328 | B2 | 10/2007 | Kong et al. |
| 7,297,518 | B2 | 11/2007 | Quake |
| 7,329,492 | B2 | 2/2008 | Hardin |
| 7,358,047 | B2 | 4/2008 | Hafner et al. |
| 7,361,488 | B2 | 4/2008 | Fan et al. |
| 7,378,242 | B2 | 5/2008 | Hurt |
| 7,393,665 | B2 | 7/2008 | Brenner |
| 7,405,281 | B2 | 7/2008 | Xu |
| 7,407,757 | B2 | 8/2008 | Brenner |
| 7,473,767 | B2 | 1/2009 | Dimitrov |
| 7,499,806 | B2 | 3/2009 | Kermani et al. |
| 7,537,897 | B2 | 5/2009 | Brenner |
| 7,563,576 | B2 | 7/2009 | Chee |
| 7,579,153 | B2 | 8/2009 | Brenner |
| 7,582,420 | B2 | 9/2009 | Oliphant et al. |
| 7,601,498 | B2 | 10/2009 | Mao |
| 7,608,434 | B2 | 10/2009 | Reznikoff et al. |
| 7,611,869 | B2 | 11/2009 | Fan |
| 7,635,566 | B2 | 12/2009 | Brenner |
| 7,666,612 | B2 | 2/2010 | Johnsson |
| 7,674,752 | B2 | 3/2010 | He |
| 7,709,198 | B2 | 5/2010 | Luo et al. |
| 7,776,547 | B2 | 8/2010 | Roth |
| 7,776,567 | B2 | 8/2010 | Mao |
| 7,803,943 | B2 | 9/2010 | Mao |
| 7,888,009 | B2 | 2/2011 | Barany et al. |
| 7,892,747 | B2 | 2/2011 | Barany et al. |
| 7,910,304 | B2 | 3/2011 | Drmanac |
| 7,914,981 | B2 | 3/2011 | Barany et al. |
| 7,955,794 | B2 | 6/2011 | Shen et al. |
| 7,960,119 | B2 | 6/2011 | Chee |
| 7,985,565 | B2 | 7/2011 | Mayer et al. |
| 8,003,354 | B2 | 8/2011 | Shen et al. |
| 8,076,063 | B2 | 12/2011 | Fan |
| 8,092,784 | B2 | 1/2012 | Mao |
| 8,148,068 | B2 | 4/2012 | Brenner |
| 8,206,917 | B2 | 6/2012 | Chee |
| 8,268,554 | B2 | 9/2012 | Schallmeiner |
| 8,288,103 | B2 | 10/2012 | Oliphant |
| 8,288,122 | B2 | 10/2012 | O'Leary et al. |
| 8,383,338 | B2 | 2/2013 | Kitzman |
| 8,431,691 | B2 | 4/2013 | McKernan et al. |
| 8,460,865 | B2 | 6/2013 | Chee |
| 8,481,257 | B2 | 7/2013 | Van Eijk |
| 8,481,258 | B2 | 7/2013 | Church et al. |
| 8,481,292 | B2 | 7/2013 | Casbon |
| 8,481,698 | B2 | 7/2013 | Lieberman et al. |
| 8,507,204 | B2 | 8/2013 | Pierce et al. |
| 8,519,115 | B2 | 8/2013 | Webster et al. |
| 8,551,710 | B2 | 10/2013 | Bernitz et al. |
| 8,568,979 | B2 | 10/2013 | Stuelpnagel et al. |
| 8,586,310 | B2 | 11/2013 | Mitra |
| 8,597,891 | B2 | 12/2013 | Barany et al. |
| 8,603,743 | B2 | 12/2013 | Liu et al. |
| 8,604,182 | B2 | 12/2013 | Luo et al. |
| 8,614,073 | B2 | 12/2013 | Van Eijk |
| 8,624,016 | B2 | 1/2014 | Barany et al. |
| 8,685,889 | B2 | 4/2014 | Van Eijk |
| 8,741,564 | B2 | 6/2014 | Seligmann |
| 8,741,606 | B2 | 6/2014 | Casbon |
| 8,771,950 | B2 | 7/2014 | Church et al. |
| 8,785,353 | B2 | 7/2014 | Van Eijk |
| 8,790,873 | B2 | 7/2014 | Namsaraev et al. |
| 8,809,238 | B2 | 8/2014 | Livak et al. |
| 8,815,512 | B2 | 8/2014 | Van Eijk |
| 8,835,358 | B2 | 9/2014 | Fodor |
| 8,865,410 | B2 | 10/2014 | Shendure |
| 8,906,626 | B2 | 12/2014 | Oliphant et al. |
| 8,911,945 | B2 | 12/2014 | Van Eijk |
| 8,936,912 | B2 | 1/2015 | Mitra |
| 8,951,726 | B2 | 2/2015 | Luo et al. |
| 8,951,728 | B2 | 2/2015 | Rasmussen |
| 8,986,926 | B2 | 3/2015 | Ferree et al. |
| 9,005,891 | B2 | 4/2015 | Sinicropi et al. |
| 9,005,935 | B2 | 4/2015 | Belyaev |
| 9,023,768 | B2 | 5/2015 | Van Eijk |
| 9,062,348 | B1 | 6/2015 | Van Eijk |
| 9,080,210 | B2 | 7/2015 | Van Eijk |
| 9,194,001 | B2 | 11/2015 | Brenner |
| 9,201,063 | B2 | 12/2015 | Sood et al. |
| 9,273,349 | B2 | 3/2016 | Nguyen et al. |
| 9,290,808 | B2 | 3/2016 | Fodor |
| 9,290,809 | B2 | 3/2016 | Fodor |
| 9,328,383 | B2 | 5/2016 | Van Eijk |
| 9,330,295 | B2 | 5/2016 | Dunn |
| 9,334,536 | B2 | 5/2016 | Van Eijk |
| 9,371,563 | B2 | 6/2016 | Geiss et al. |
| 9,371,598 | B2 | 6/2016 | Chee |
| 9,376,716 | B2 | 6/2016 | Van Eijk |
| 9,376,717 | B2 | 6/2016 | Gao et al. |
| 9,376,719 | B2 | 6/2016 | Van Eijk |
| 9,416,409 | B2 | 8/2016 | Hayden |
| 9,447,459 | B2 | 9/2016 | Van Eijk |
| 9,453,256 | B2 | 9/2016 | Van Eijk |
| 9,493,820 | B2 | 11/2016 | Van Eijk |
| 9,506,061 | B2 | 11/2016 | Brown et al. |
| 9,512,422 | B2 | 12/2016 | Barnard et al. |
| 9,574,230 | B2 | 2/2017 | Van Eijk |

(56) References Cited

U.S. PATENT DOCUMENTS 9,593,365 B2 3/2017 Frisen et al.
9,598,728 B2 3/2017 Barany et al.
9,624,538 B2 4/2017 Church et al.
9,644,204 B2 5/2017 Hindson et al.
9,657,335 B2 5/2017 Van Eijk
9,670,542 B2 6/2017 Van Eijk
9,694,361 B2 7/2017 Bharadwaj
9,702,004 B2 7/2017 Van Eijk
9,714,446 B2 7/2017 Webster et al.
9,714,937 B2 7/2017 Dunaway
9,727,810 B2 8/2017 Fodor et al.
9,745,627 B2 8/2017 Van Eijk
9,777,324 B2 10/2017 Van Eijk
9,783,841 B2 10/2017 Nolan et al.
9,790,476 B2 10/2017 Gloeckner et al.
9,816,134 B2 11/2017 Namsaraev
9,834,814 B2 12/2017 Peter et al.
9,850,536 B2 12/2017 Oliphant et al.
9,856,521 B2 1/2018 Stevens et al.
9,868,979 B2 1/2018 Chee et al.
9,879,313 B2 1/2018 Chee et al.
9,896,721 B2 2/2018 Van Eijk
9,898,576 B2 2/2018 Van Eijk
9,898,577 B2 2/2018 Van Eijk
9,902,991 B2 2/2018 Sinicropi et al.
9,909,167 B2 3/2018 Samusik et al.
9,938,566 B2 4/2018 Shepard et al.
9,957,550 B2 5/2018 Yeakley et al.
10,002,316 B2 6/2018 Fodor et al.
10,023,907 B2 7/2018 Van Eijk
10,030,261 B2 7/2018 Frisen et al.
10,035,992 B2 7/2018 Gloeckner et al.
10,041,949 B2 8/2018 Bendall et al.
10,059,989 B2 8/2018 Giresi et al.
10,059,990 B2 8/2018 Boyden et al.
10,095,832 B2 10/2018 Van Eijk
10,101,336 B2 10/2018 Bergo
10,144,966 B2 12/2018 Cantor
10,208,982 B2 2/2019 Bannish et al.
10,227,639 B2 3/2019 Levner et al.
10,273,541 B2 4/2019 Hindson et al.
10,308,982 B2 6/2019 Chee
10,317,321 B2 6/2019 Tillberg et al.
10,357,771 B2 7/2019 Bharadwaj
10,364,457 B2 7/2019 Wassie et al.
10,370,698 B2 8/2019 Nolan et al.
10,415,080 B2 9/2019 Dunaway et al.
10,465,235 B2 11/2019 Gullberg et al.
10,472,669 B2 11/2019 Chee
10,480,022 B2 11/2019 Chee
10,480,029 B2 11/2019 Bent et al.
10,494,662 B2 12/2019 Church et al.
10,494,667 B2 12/2019 Chee
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,544,403 B2 1/2020 Gloeckner et al.
10,550,429 B2 2/2020 Harada et al.
10,590,244 B2 3/2020 Delaney et al.
10,633,648 B2 4/2020 Seelig et al.
10,640,816 B2 5/2020 Beechem et al.
10,640,826 B2 5/2020 Church et al.
10,662,466 B2 5/2020 Berry et al.
10,662,468 B2 5/2020 Chee
10,669,569 B2 6/2020 Gullberg et al.
10,724,078 B2 7/2020 Van Driel et al.
10,725,027 B2 7/2020 Bell
10,774,372 B2 9/2020 Chee et al.
10,774,374 B2 9/2020 Frisen et al.
10,787,701 B2 9/2020 Chee
10,815,519 B2 10/2020 Husain et al.
10,829,803 B2 11/2020 Terbrueggen et al.
10,844,426 B2 11/2020 Daugharthy et al.
10,858,698 B2 12/2020 Church et al.
10,858,702 B2 12/2020 Lucero et al.
10,913,975 B2 2/2021 So et al.
10,914,730 B2 2/2021 Chee et al.
10,927,403 B2 2/2021 Chee et al.
10,961,566 B2 3/2021 Chee
10,995,361 B2 5/2021 Chen et al.
11,001,879 B1 5/2021 Chee
11,008,607 B2 5/2021 Chee
11,008,608 B2 5/2021 Samusik et al.
11,046,996 B1 6/2021 Chee et al.
11,067,567 B2 7/2021 Chee
11,104,936 B2 8/2021 Zhang et al.
11,118,216 B2 9/2021 Koshinsky et al.
11,156,603 B2 10/2021 Chee
11,162,132 B2 11/2021 Frisen et al.
11,168,350 B2 11/2021 Nolan et al.
11,208,684 B2 12/2021 Chee
11,214,796 B2 1/2022 Shirai et al.
11,286,515 B2 3/2022 Chee et al.
11,293,917 B2 4/2022 Chee
11,299,774 B2 4/2022 Frisen et al.
11,313,856 B2 4/2022 Chee
11,332,790 B2 5/2022 Chell et al.
11,352,659 B2 6/2022 Frisen et al.
11,352,667 B2 6/2022 Hauling et al.
11,359,228 B2 6/2022 Chee et al.
11,365,442 B2 6/2022 Chee
11,371,086 B2 6/2022 Chee
11,384,386 B2 7/2022 Chee
11,390,912 B2 7/2022 Frisen et al.
11,401,545 B2 8/2022 Chee
11,407,992 B2 8/2022 Dadhwal
11,408,029 B2 8/2022 Katiraee et al.
11,434,524 B2 9/2022 Ramachandran Iyer et al.
11,447,807 B2 9/2022 Church et al.
11,459,607 B1 10/2022 Terry et al.
11,479,809 B2 10/2022 Frisen et al.
11,479,810 B1 10/2022 Chee
11,492,612 B1 11/2022 Dadhwal
11,501,440 B2 11/2022 Weisenfeld et al.
11,505,828 B2 11/2022 Chell et al.
11,512,308 B2 11/2022 Gallant et al.
11,519,022 B2 12/2022 Chee
11,519,033 B2 12/2022 Schnall-Levin et al.
11,530,438 B2 12/2022 Persson et al.
11,535,887 B2 12/2022 Gallant et al.
11,542,543 B2 1/2023 Chee
11,549,138 B2 1/2023 Chee
11,560,587 B2 1/2023 Chee
11,560,592 B2 1/2023 Chew et al.
11,560,593 B2 1/2023 Chell et al.
11,592,447 B2 2/2023 Uytingco et al.
11,608,498 B2 3/2023 Gallant et al.
11,608,520 B2 3/2023 Galonska et al.
11,613,773 B2 3/2023 Frisen et al.
11,618,897 B2 4/2023 Kim et al.
11,618,918 B2 4/2023 Chee et al.
11,624,063 B2 4/2023 Dadhwal
11,624,086 B2 4/2023 Uytingco et al.
11,634,756 B2 4/2023 Chee
11,649,485 B2 5/2023 Yin et al.
11,661,626 B2 5/2023 Katiraee et al.
11,680,260 B2 6/2023 Kim et al.
11,692,218 B2 7/2023 Engblom et al.
11,702,693 B2 7/2023 Bharadwaj
11,702,698 B2 7/2023 Stoeckius
11,713,480 B2 8/2023 Lee
11,732,292 B2 8/2023 Chee
11,732,299 B2 8/2023 Ramachandran Iyer
11,732,300 B2 8/2023 Bava
11,733,238 B2 8/2023 Chee
11,739,372 B2 8/2023 Frisen et al.
11,739,381 B2 8/2023 Chew et al.
11,753,673 B2 9/2023 Chew et al.
11,753,674 B2 9/2023 Chee et al.
11,753,675 B2 9/2023 Ramachandran Iyer
11,761,030 B2 9/2023 Chee
11,761,038 B1 9/2023 Stoeckius
11,767,550 B2 9/2023 Chee

(56) References Cited

U.S. PATENT DOCUMENTS

| | | | |
|---|---|---|---|
| 11,768,175 | B1 | 9/2023 | Kim et al. |
| 11,773,433 | B2 | 10/2023 | Gallant et al. |
| 11,781,130 | B2 | 10/2023 | Dadhwal |
| 11,788,122 | B2 | 10/2023 | Frisen et al. |
| 11,795,498 | B2 | 10/2023 | Frisen et al. |
| 11,795,507 | B2 | 10/2023 | Chell et al. |
| 11,808,769 | B2 | 11/2023 | Uytingco et al. |
| 11,821,024 | B2 | 11/2023 | Chee et al. |
| 11,821,035 | B1 | 11/2023 | Bent et al. |
| 11,827,935 | B1 | 11/2023 | Ramachandran Iyer et al. |
| 11,835,462 | B2 | 12/2023 | Bava |
| 11,840,687 | B2 | 12/2023 | Gallant et al. |
| 11,840,724 | B2 | 12/2023 | Chew et al. |
| 11,845,979 | B2 | 12/2023 | Engblom et al. |
| 11,859,178 | B2 | 1/2024 | Gallant et al. |
| 11,866,767 | B2 | 1/2024 | Uytingco et al. |
| 11,866,770 | B2 | 1/2024 | Chee |
| 11,873,482 | B2 | 1/2024 | Kim et al. |
| 11,891,654 | B2 | 2/2024 | Alvarado Martinez et al. |
| 11,898,205 | B2 | 2/2024 | Bava |
| 11,926,822 | B1 | 3/2024 | Gohil et al. |
| 11,926,863 | B1 | 3/2024 | Boutet |
| 11,926,867 | B2 | 3/2024 | Yin et al. |
| 11,933,957 | B1 | 3/2024 | Tentori et al. |
| 11,952,627 | B2 | 4/2024 | Stoeckius |
| 11,959,076 | B2 | 4/2024 | Kim et al. |
| 11,959,130 | B2 | 4/2024 | Galonska et al. |
| 11,965,213 | B2 | 4/2024 | Williams |
| 11,970,739 | B2 | 4/2024 | Chew et al. |
| 11,981,958 | B1 | 5/2024 | Galonska |
| 11,981,960 | B1 | 5/2024 | Lin et al. |
| 11,981,965 | B2 | 5/2024 | Chell et al. |
| RE50,065 | E | 7/2024 | Frisen et al. |
| 12,024,741 | B2 | 7/2024 | Tentori et al. |
| 12,031,177 | B1 | 7/2024 | Tentori et al. |
| 12,060,604 | B2 | 8/2024 | Katiraee et al. |
| 12,071,655 | B2 | 8/2024 | Sukovich et al. |
| 12,076,701 | B2 | 9/2024 | Bava |
| 12,098,417 | B2 | 9/2024 | Engblom et al. |
| 12,098,985 | B2 | 9/2024 | Cox et al. |
| 12,110,541 | B2 | 10/2024 | Bava |
| 12,117,439 | B2 | 10/2024 | Delaney et al. |
| 12,128,403 | B2 | 10/2024 | Kim et al. |
| 12,129,516 | B2 | 10/2024 | Tentori et al. |
| 12,157,124 | B2 | 12/2024 | Cox et al. |
| 12,180,543 | B2 | 12/2024 | Uytingco et al. |
| 12,195,790 | B2 | 1/2025 | Sukovich et al. |
| 12,203,134 | B2 | 1/2025 | Nagendran et al. |
| 12,209,280 | B1 | 1/2025 | Mignardi et al. |
| D1,064,308 | S | 2/2025 | Alimsijah et al. |
| 12,223,751 | B2 | 2/2025 | Li et al. |
| 12,228,544 | B2 | 2/2025 | Kim et al. |
| 12,234,505 | B2 | 2/2025 | Chee |
| 12,241,060 | B2 | 3/2025 | Kim et al. |
| 12,241,890 | B2 | 3/2025 | Delaney et al. |
| 12,249,085 | B2 | 3/2025 | Tentori et al. |
| 12,265,079 | B1 | 4/2025 | Bent |
| 12,270,077 | B2 | 4/2025 | Schnall-Levin et al. |
| 12,275,988 | B2 | 4/2025 | Galonska et al. |
| 12,281,357 | B1 | 4/2025 | Tentori et al. |
| 12,286,673 | B2 | 4/2025 | Bava |
| 12,287,264 | B2 | 4/2025 | Cox et al. |
| 12,297,486 | B2 | 5/2025 | Patterson et al. |
| 12,297,487 | B2 | 5/2025 | Chee |
| 12,297,488 | B2 | 5/2025 | Chee |
| 12,344,892 | B2 | 7/2025 | Schnall-Levin et al. |
| 12,365,935 | B2 | 7/2025 | Chew et al. |
| 12,365,942 | B2 | 7/2025 | Stoeckius |
| 12,371,688 | B2 | 7/2025 | Kim et al. |
| 12,378,607 | B2 | 8/2025 | Schnall-Levin et al. |
| 12,385,083 | B2 | 8/2025 | Shah |
| 12,391,979 | B2 | 8/2025 | Chee |
| 12,391,980 | B2 | 8/2025 | Chee |
| 12,399,123 | B1 | 8/2025 | Shah et al. |
| 12,404,544 | B2 | 9/2025 | Tentori et al. |
| 12,405,264 | B2 | 9/2025 | Stoeckius |
| 12,416,603 | B2 | 9/2025 | Tentori et al. |
| 12,435,363 | B1 | 10/2025 | Gallant et al. |
| 12,442,045 | B2 | 10/2025 | Williams |
| 12,497,654 | B2 | 12/2025 | Ramachandran Iyer et al. |
| 12,508,590 | B2 | 12/2025 | Kim et al. |
| D1,108,656 | S | 1/2026 | Alimsijah et al. |
| 12,529,094 | B2 | 1/2026 | Bent et al. |
| 12,545,949 | B2 | 2/2026 | Bent et al. |
| 12,553,805 | B2 | 2/2026 | Shahjamali |
| 12,553,898 | B1 | 2/2026 | Uytingco et al. |
| 12,566,113 | B2 | 3/2026 | Delaney et al. |
| 12,566,114 | B2 | 3/2026 | Cox et al. |
| 12,571,029 | B1 | 3/2026 | Galonska et al. |
| 12,668,835 | B1 | 6/2026 | Tentori et al. |
| 2001/0055764 | A1 | 12/2001 | Empendocles et al. |
| 2002/0040275 | A1 | 4/2002 | Cravatt |
| 2002/0051986 | A1 | 5/2002 | Baez et al. |
| 2002/0055100 | A1 | 5/2002 | Kawashima |
| 2002/0058250 | A1 | 5/2002 | Firth |
| 2002/0086441 | A1 | 7/2002 | Baranov et al. |
| 2002/0164611 | A1 | 11/2002 | Bamdad |
| 2003/0017451 | A1 | 1/2003 | Wang et al. |
| 2003/0022207 | A1 | 1/2003 | Balasubramanian |
| 2003/0064398 | A1 | 4/2003 | Barnes |
| 2003/0092624 | A1 | 5/2003 | Wang et al. |
| 2003/0138879 | A1 | 7/2003 | Lambalot |
| 2003/0148335 | A1 | 8/2003 | Shen et al. |
| 2003/0162216 | A1 | 8/2003 | Gold |
| 2003/0165948 | A1 | 9/2003 | Alsmadi et al. |
| 2003/0211489 | A1 | 11/2003 | Shen et al. |
| 2003/0224419 | A1 | 12/2003 | Corcoran |
| 2003/0232348 | A1 | 12/2003 | Jones et al. |
| 2003/0232382 | A1 | 12/2003 | Brennan |
| 2003/0235854 | A1 | 12/2003 | Chan et al. |
| 2004/0009487 | A1 | 1/2004 | Kadushin et al. |
| 2004/0033499 | A1 | 2/2004 | Ilsley et al. |
| 2004/0067492 | A1 | 4/2004 | Peng et al. |
| 2004/0082059 | A1 | 4/2004 | Webb et al. |
| 2004/0096853 | A1 | 5/2004 | Mayer |
| 2004/0101835 | A1 | 5/2004 | Willis et al. |
| 2004/0106110 | A1 | 6/2004 | Balasubramanian |
| 2004/0235103 | A1 | 11/2004 | Reznikoff et al. |
| 2004/0241660 | A1 | 12/2004 | Wojtowicz et al. |
| 2004/0248325 | A1 | 12/2004 | Bukusoglu et al. |
| 2004/0259105 | A1 | 12/2004 | Fan et al. |
| 2005/0003431 | A1 | 1/2005 | Wucherpfennig |
| 2005/0014203 | A1 | 1/2005 | Darfler et al. |
| 2005/0037393 | A1 | 2/2005 | Gunderson et al. |
| 2005/0048498 | A1 | 3/2005 | Woudenberg et al. |
| 2005/0048580 | A1 | 3/2005 | Labaer |
| 2005/0064460 | A1 | 3/2005 | Holliger et al. |
| 2005/0095627 | A1 | 5/2005 | Kolman et al. |
| 2005/0100900 | A1 | 5/2005 | Kawashima et al. |
| 2005/0130173 | A1 | 6/2005 | Leamon et al. |
| 2005/0136414 | A1 | 6/2005 | Gunderson et al. |
| 2005/0164292 | A1 | 7/2005 | Farooqui |
| 2005/0170373 | A1 | 8/2005 | Monforte |
| 2005/0191656 | A1 | 9/2005 | Drmanac et al. |
| 2005/0191698 | A1 | 9/2005 | Chee et al. |
| 2005/0202433 | A1 | 9/2005 | Van Beuningen |
| 2005/0227271 | A1 | 10/2005 | Kwon |
| 2005/0239119 | A1 | 10/2005 | Tsukada et al. |
| 2005/0260653 | A1 | 11/2005 | LaBaer |
| 2005/0266417 | A1 | 12/2005 | Barany et al. |
| 2006/0041385 | A1 | 2/2006 | Bauer et al. |
| 2006/0046313 | A1 | 3/2006 | Roth |
| 2006/0084078 | A1 | 4/2006 | Zhao |
| 2006/0105352 | A1 | 5/2006 | Qiao et al. |
| 2006/0154286 | A1 | 7/2006 | Kong et al. |
| 2006/0188901 | A1 | 8/2006 | Barnes et al. |
| 2006/0199183 | A1 | 9/2006 | Valat et al. |
| 2006/0211001 | A1 | 9/2006 | Yu et al. |
| 2006/0216775 | A1 | 9/2006 | Burkart et al. |
| 2006/0240439 | A1 | 10/2006 | Smith et al. |
| 2006/0263789 | A1 | 11/2006 | Kincaid |
| 2006/0275782 | A1 | 12/2006 | Gunderson et al. |
| 2006/0281109 | A1 | 12/2006 | Barr Ost et al. |
| 2007/0020640 | A1 | 1/2007 | McCloskey et al. |

(56) References Cited

U.S. PATENT DOCUMENTS

2007/0020669 A1 1/2007 Ericsson
2007/0026430 A1 2/2007 Andersen et al.
2007/0054288 A1 3/2007 Su et al.
2007/0087360 A1 4/2007 Boyd
2007/0099208 A1 5/2007 Drmanac et al.
2007/0128624 A1 6/2007 Gormley et al.
2007/0128656 A1 6/2007 Agrawal
2007/0134723 A1 6/2007 Kozlov et al.
2007/0161020 A1 7/2007 Luo et al.
2007/0166705 A1 7/2007 Milton et al.
2007/0172873 A1 7/2007 Brenner et al.
2007/0207482 A1 9/2007 Church et al.
2007/0254305 A1 11/2007 Paik et al.
2007/0269805 A1 11/2007 Hogers
2008/0003586 A1 1/2008 Hyde et al.
2008/0009420 A1 1/2008 Schroth et al.
2008/0108082 A1 5/2008 Rank et al.
2008/0108804 A1 5/2008 Hayashizaki et al.
2008/0132429 A1 6/2008 Perov et al.
2008/0160580 A1 7/2008 Adessi et al.
2008/0220434 A1 9/2008 Thomas
2008/0261204 A1 10/2008 Lexow
2008/0286795 A1 11/2008 Kawashima et al.
2008/0293046 A1 11/2008 Allawi et al.
2009/0005252 A1 1/2009 Drmanac et al.
2009/0006002 A1 1/2009 Honisch et al.
2009/0018024 A1 1/2009 Church et al.
2009/0026082 A1 1/2009 Rothberg et al.
2009/0036323 A1 2/2009 van Eijk et al.
2009/0082212 A1 3/2009 Williams
2009/0099041 A1 4/2009 Church et al.
2009/0105959 A1 4/2009 Braverman et al.
2009/0117573 A1 5/2009 Fu et al.
2009/0127589 A1 5/2009 Rothberg et al.
2009/0155781 A1 6/2009 Drmanac et al.
2009/0170713 A1 7/2009 van Eijk et al.
2009/0202998 A1 8/2009 Schlumpberger et al.
2009/0233802 A1 9/2009 Bignell et al.
2009/0253581 A1 10/2009 van Eijk et al.
2009/0270273 A1 10/2009 Burns et al.
2009/0283407 A1 11/2009 Van Eijk
2009/0286249 A1 11/2009 Becker et al.
2009/0291854 A1 11/2009 Weisinger-Mayr et al.
2009/0312193 A1 12/2009 Kim et al.
2010/0035249 A1 2/2010 Hayashizaki et al.
2010/0047790 A1 2/2010 Southern et al.
2010/0069263 A1 3/2010 Shendure et al.
2010/0105052 A1 4/2010 Drmanac et al.
2010/0120097 A1 5/2010 Matz et al.
2010/0120098 A1 5/2010 Grunenwald et al.
2010/0129874 A1 5/2010 Mitra et al.
2010/0145037 A1 6/2010 Brive et al.
2010/0173384 A1 7/2010 Johnsson et al.
2010/0184618 A1 7/2010 Namsaraev et al.
2010/0210475 A1 8/2010 Lee et al.
2010/0227329 A1 9/2010 Cuppens
2010/0273219 A1 10/2010 May et al.
2011/0028685 A1 2/2011 Purkayastha et al.
2011/0031123 A1 2/2011 Schulze et al.
2011/0033854 A1 2/2011 Drmanac et al.
2011/0045462 A1 2/2011 Fu et al.
2011/0059436 A1 3/2011 Hardin et al.
2011/0111409 A1 5/2011 Sinicropi et al.
2011/0152111 A1 6/2011 Fan et al.
2011/0237449 A1 9/2011 McMaster et al.
2011/0245101 A1 10/2011 Chee et al.
2011/0245111 A1 10/2011 Chee
2011/0269631 A1 11/2011 Fu et al.
2011/0287435 A1 11/2011 Grunenwald et al.
2012/0021930 A1 1/2012 Schoen et al.
2012/0046175 A1 2/2012 Rodesch et al.
2012/0046178 A1 2/2012 Van Den Boom et al.
2012/0065081 A1 3/2012 Chee
2012/0135871 A1 5/2012 van Eijk et al.
2012/0202698 A1 8/2012 van Eijk et al.
2012/0202704 A1 8/2012 Fan et al.
2012/0220479 A1 8/2012 Ericsson et al.
2012/0245053 A1 9/2012 Shirai et al.
2012/0252702 A1 10/2012 Muratani et al.
2012/0258871 A1 10/2012 Kozlov et al.
2012/0289414 A1 11/2012 Mitra et al.
2012/0301925 A1 11/2012 Belyaev
2013/0005594 A1 1/2013 Terbrueggen et al.
2013/0005600 A1 1/2013 Olek
2013/0023433 A1 1/2013 Luo et al.
2013/0035239 A1 2/2013 Kong et al.
2013/0040842 A1 2/2013 Lim et al.
2013/0065768 A1 3/2013 Zheng et al.
2013/0079232 A1 3/2013 Kain et al.
2013/0171621 A1 7/2013 Luo et al.
2013/0244884 A1 9/2013 Jacobson et al.
2013/0261019 A1 10/2013 Lin et al.
2013/0302801 A1 11/2013 Asbury et al.
2013/0338042 A1 12/2013 Shen et al.
2014/0066318 A1 3/2014 Frisen et al.
2014/0121118 A1 5/2014 Warner
2014/0270435 A1 9/2014 Dunn
2014/0274731 A1 9/2014 Raymond et al.
2014/0323330 A1 10/2014 Glezer et al.
2014/0342921 A1 11/2014 Weiner
2014/0378350 A1 12/2014 Hindson et al.
2015/0285720 A1 10/2015 Hay et al.
2015/0292988 A1 10/2015 Bharadwaj et al.
2015/0344942 A1 12/2015 Frisen et al.
2016/0019337 A1 1/2016 Roberts et al.
2016/0024576 A1 1/2016 Chee
2016/0041159 A1 2/2016 Labaer et al.
2016/0060687 A1 3/2016 Zhu et al.
2016/0108458 A1 4/2016 Frei et al.
2016/0122817 A1 5/2016 Jarosz et al.
2016/0138091 A1 5/2016 Chee et al.
2016/0145677 A1 5/2016 Chee et al.
2016/0194692 A1 7/2016 Gore et al.
2016/0201125 A1 7/2016 Samuels et al.
2016/0253584 A1 9/2016 Fodor et al.
2016/0289740 A1 10/2016 Fu et al.
2016/0298180 A1 10/2016 Chee
2016/0305856 A1 10/2016 Boyden et al.
2016/0312276 A1 10/2016 Fu et al.
2016/0333403 A1 11/2016 Chee
2016/0376642 A1 12/2016 Landegren et al.
2017/0009278 A1 1/2017 Söderberg et al.
2017/0016053 A1 1/2017 Beechem et al.
2017/0058339 A1 3/2017 Chee
2017/0058340 A1 3/2017 Chee
2017/0058345 A1 3/2017 Chee
2017/0088881 A1 3/2017 Chee
2017/0159109 A1 6/2017 Zheng et al.
2017/0166962 A1 6/2017 van Eijk et al.
2017/0220733 A1 8/2017 Zhuang et al.
2017/0233722 A1 8/2017 Seelig et al.
2017/0283860 A1 10/2017 Kool et al.
2017/0335297 A1 11/2017 Ha et al.
2017/0335410 A1 11/2017 Driscoll et al.
2017/0342405 A1 11/2017 Fu et al.
2017/0349940 A1 12/2017 Morin et al.
2018/0057873 A1 3/2018 Zhou et al.
2018/0080019 A1 3/2018 Blainey et al.
2018/0088112 A1 3/2018 Fan et al.
2018/0094316 A1 4/2018 Oliphant et al.
2018/0112261 A1 4/2018 Van Driel et al.
2018/0119219 A1 5/2018 Chen et al.
2018/0127817 A1 5/2018 Borchert et al.
2018/0163265 A1 6/2018 Zhang et al.
2018/0179591 A1 6/2018 van Eijk
2018/0201925 A1 7/2018 Steemers et al.
2018/0201980 A1 7/2018 Chee et al.
2018/0208967 A1 7/2018 Larman et al.
2018/0216161 A1 8/2018 Chen et al.
2018/0216162 A1 8/2018 Belhocine et al.
2018/0237864 A1 8/2018 Imler et al.
2018/0245142 A1 8/2018 So et al.
2018/0247017 A1 8/2018 van Eijk et al.
2018/0291427 A1 10/2018 Edelman

(56) References Cited

U.S. PATENT DOCUMENTS

2018/0291439 A1 10/2018 van Eijk et al.
2018/0305681 A1 10/2018 Jovanovich et al.
2018/0312822 A1 11/2018 Lee et al.
2018/0320226 A1 11/2018 Church et al.
2018/0334670 A1 11/2018 Bharadwaj et al.
2019/0055594 A1 2/2019 Samusik et al.
2019/0064173 A1 2/2019 Bharadwaj et al.
2019/0071656 A1 3/2019 Chang et al.
2019/0085383 A1 3/2019 Church et al.
2019/0119735 A1 4/2019 Deisseroth et al.
2019/0135774 A1 5/2019 Orbai
2019/0145982 A1 5/2019 Chee et al.
2019/0161796 A1 5/2019 Hauling et al.
2019/0177777 A1 6/2019 Chee
2019/0177778 A1 6/2019 Chee
2019/0177789 A1 6/2019 Hindson et al.
2019/0177800 A1 6/2019 Boutet et al.
2019/0203275 A1 7/2019 Frisen et al.
2019/0218276 A1 7/2019 Regev et al.
2019/0218608 A1 7/2019 Daugharthy et al.
2019/0233878 A1 8/2019 Delaney et al.
2019/0233880 A1 8/2019 Mir
2019/0249226 A1 8/2019 Bent et al.
2019/0262831 A1 8/2019 West et al.
2019/0264268 A1 8/2019 Frisen et al.
2019/0271028 A1 9/2019 Khafizov et al.
2019/0271030 A1 9/2019 Chee
2019/0271031 A1 9/2019 Chee
2019/0300943 A1 10/2019 Chee et al.
2019/0300944 A1 10/2019 Chee et al.
2019/0300945 A1 10/2019 Chee et al.
2019/0309353 A1 10/2019 Chee
2019/0309354 A1 10/2019 Chee
2019/0309355 A1 10/2019 Chee
2019/0323071 A1 10/2019 Chee
2019/0323088 A1 10/2019 Boutet et al.
2019/0330617 A1 10/2019 Church et al.
2019/0338353 A1 11/2019 Belgrader et al.
2019/0360034 A1 11/2019 Zhou et al.
2019/0360043 A1 11/2019 Pham et al.
2019/0367969 A1 12/2019 Belhocine et al.
2019/0367982 A1 12/2019 Belhocine et al.
2019/0367997 A1 12/2019 Bent et al.
2020/0002763 A1 1/2020 Belgrader et al.
2020/0010891 A1 1/2020 Beechem et al.
2020/0024641 A1 1/2020 Nolan et al.
2020/0040376 A1 2/2020 Russel et al.
2020/0047010 A1 2/2020 Lee et al.
2020/0048690 A1 2/2020 Chee
2020/0063191 A1 2/2020 Kennedy-Darling et al.
2020/0063195 A1 2/2020 Chee
2020/0063196 A1 2/2020 Chee
2020/0071751 A1 3/2020 Daugharthy et al.
2020/0080136 A1 3/2020 Zhang et al.
2020/0109443 A1 4/2020 Chee
2020/0123597 A1 4/2020 Daniel
2020/0131570 A1 4/2020 Berti et al.
2020/0140920 A1 5/2020 Pierce et al.
2020/0173985 A1 6/2020 Dong et al.
2020/0199565 A1 6/2020 Chen et al.
2020/0199572 A1 6/2020 Kuersten et al.
2020/0224244 A1 7/2020 Nilsson et al.
2020/0239874 A1 7/2020 Mikkelsen
2020/0239946 A1 7/2020 Dewal
2020/0256867 A1 8/2020 Hennek et al.
2020/0277663 A1 9/2020 Iyer
2020/0277664 A1 9/2020 Frenz
2020/0283852 A1 9/2020 Oliphant et al.
2020/0299757 A1 9/2020 Chee et al.
2020/0325531 A1 10/2020 Chee
2020/0362398 A1 11/2020 Kishi et al.
2020/0370095 A1 11/2020 Farmer et al.
2020/0399687 A1 12/2020 Frisen et al.
2020/0407781 A1 12/2020 Schnall-Levin
2021/0010068 A1 1/2021 Chee et al.
2021/0010070 A1 1/2021 Schnall-Levin et al.
2021/0017587 A1 1/2021 Cai et al.
2021/0095331 A1 4/2021 Fan et al.
2021/0115504 A1 4/2021 Cai et al.
2021/0123040 A1 4/2021 Macosko et al.
2021/0130881 A1 5/2021 Cox
2021/0140982 A1 5/2021 Uytingco et al.
2021/0150707 A1 5/2021 Weisenfeld et al.
2021/0155982 A1 5/2021 Yin et al.
2021/0158522 A1 5/2021 Weisenfeld et al.
2021/0172007 A1 6/2021 Chee et al.
2021/0189475 A1 6/2021 Tentori et al.
2021/0190770 A1 6/2021 Delaney et al.
2021/0198741 A1 7/2021 Williams
2021/0199660 A1 7/2021 Williams et al.
2021/0207202 A1 7/2021 Chee
2021/0214785 A1 7/2021 Stoeckius
2021/0222235 A1 7/2021 Chee
2021/0222241 A1 7/2021 Bharadwaj
2021/0222242 A1 7/2021 Ramachandran Iyer
2021/0222253 A1 7/2021 Uytingco
2021/0223227 A1 7/2021 Stoeckius
2021/0230584 A1 7/2021 Mikkelsen et al.
2021/0230681 A1 7/2021 Patterson et al.
2021/0230692 A1 7/2021 Daugharthy et al.
2021/0237022 A1 8/2021 Bava
2021/0238581 A1 8/2021 Mikkelsen et al.
2021/0238664 A1 8/2021 Bava et al.
2021/0238675 A1 8/2021 Bava
2021/0238680 A1 8/2021 Bava
2021/0247316 A1 8/2021 Bava
2021/0255175 A1 8/2021 Chee et al.
2021/0262018 A1 8/2021 Bava et al.
2021/0262019 A1 8/2021 Alvarado Martinez et al.
2021/0269864 A1 9/2021 Chee
2021/0270822 A1 9/2021 Chee
2021/0277460 A1 9/2021 Bava
2021/0285036 A1 9/2021 Yin et al.
2021/0285046 A1 9/2021 Chell et al.
2021/0292748 A1 9/2021 Frisen et al.
2021/0292822 A1 9/2021 Frisen et al.
2021/0317510 A1 10/2021 Chee et al.
2021/0317524 A1 10/2021 Lucero et al.
2021/0324457 A1 10/2021 Ramachandran Iyer et al.
2021/0332424 A1 10/2021 Schnall-Levin
2021/0332425 A1 10/2021 Pfeiffer et al.
2021/0348221 A1 11/2021 Chell et al.
2022/0002791 A1 1/2022 Frisen et al.
2022/0003755 A1 1/2022 Chee
2022/0010367 A1 1/2022 Ramachandran Iyer et al.
2022/0017951 A1 1/2022 Ramachandran Iyer et al.
2022/0025446 A1 1/2022 Shah
2022/0025447 A1 1/2022 Tentori et al.
2022/0033888 A1 2/2022 Schnall-Levin et al.
2022/0049293 A1 2/2022 Frenz et al.
2022/0064630 A1 3/2022 Bent et al.
2022/0081728 A1 3/2022 Williams
2022/0090058 A1 3/2022 Frisen et al.
2022/0090175 A1 3/2022 Uytingco et al.
2022/0098576 A1 3/2022 Dadhwal
2022/0098661 A1 3/2022 Chew et al.
2022/0106632 A1 4/2022 Galonska et al.
2022/0106633 A1 4/2022 Engblom et al.
2022/0112486 A1 4/2022 Ramachandran Iyer et al.
2022/0112545 A1 4/2022 Chee
2022/0119869 A1 4/2022 Ramachandran Iyer et al.
2022/0127659 A1 4/2022 Frisen et al.
2022/0127666 A1 4/2022 Katiraee et al.
2022/0127672 A1 4/2022 Stoeckius
2022/0145361 A1 5/2022 Frenz et al.
2022/0154255 A1 5/2022 Chee et al.
2022/0170083 A1 6/2022 Khaled et al.
2022/0195422 A1 6/2022 Gallant et al.
2022/0195505 A1 6/2022 Frisen et al.
2022/0196644 A1 6/2022 Chee
2022/0213526 A1 7/2022 Frisen et al.
2022/0220544 A1 7/2022 Ach et al.
2022/0241780 A1 8/2022 Tentori et al.
2022/0267844 A1 8/2022 Ramachandran Iyer et al.

(56) References Cited

U.S. PATENT DOCUMENTS

2022/0282329 A1 9/2022 Chell et al.
2022/0290217 A1 9/2022 Frenz et al.
2022/0290219 A1 9/2022 Chee
2022/0298560 A1 9/2022 Frisen et al.
2022/0325325 A1 10/2022 Chee et al.
2022/0326251 A1 10/2022 Uytingco et al.
2022/0333171 A1 10/2022 Chee
2022/0333191 A1 10/2022 Mikkelsen et al.
2022/0333192 A1 10/2022 Uytingco
2022/0333195 A1 10/2022 Schnall-Levin et al.
2022/0334031 A1 10/2022 Delaney et al.
2022/0348905 A1 11/2022 Dadhwal
2022/0348992 A1 11/2022 Stoeckius et al.
2022/0356464 A1 11/2022 Kim et al.
2022/0364163 A1 11/2022 Stahl et al.
2022/0389491 A1 12/2022 Chee
2022/0389503 A1 12/2022 Mikkelsen et al.
2022/0389504 A1 12/2022 Chew et al.
2022/0403455 A1 12/2022 Ramachandran Iyer et al.
2022/0404245 A1 12/2022 Chell et al.
2023/0002812 A1 1/2023 Stoeckius et al.
2023/0014008 A1 1/2023 Shastry
2023/0017773 A1 1/2023 Kim et al.
2023/0031305 A1 2/2023 Hernandez Neuta et al.
2023/0033960 A1 2/2023 Gallant et al.
2023/0034039 A1 2/2023 Shahjamali
2023/0034216 A1 2/2023 Bava
2023/0040363 A1 2/2023 Chee
2023/0042088 A1 2/2023 Chee
2023/0042817 A1 2/2023 Mignardi
2023/0047782 A1 2/2023 Tentori et al.
2023/0056549 A1 2/2023 Dadhwal
2023/0064372 A1 3/2023 Chell et al.
2023/0069046 A1 3/2023 Chew et al.
2023/0077364 A1 3/2023 Patterson et al.
2023/0080543 A1 3/2023 Katiraee et al.
2023/0081381 A1 3/2023 Chew et al.
2023/0100497 A1 3/2023 Frisen et al.
2023/0107023 A1 4/2023 Chee
2023/0111225 A1 4/2023 Chew et al.
2023/0113230 A1 4/2023 Kim et al.
2023/0126825 A1 4/2023 Nagendran et al.
2023/0129552 A1 4/2023 Ramachandran Iyer
2023/0135010 A1 5/2023 Tentori et al.
2023/0143569 A1 5/2023 Iyer et al.
2023/0145575 A1 5/2023 Gallant et al.
2023/0147726 A1 5/2023 Hadrup et al.
2023/0151412 A1 5/2023 Chee
2023/0159994 A1 5/2023 Chee
2023/0159995 A1 5/2023 Iyer et al.
2023/0160008 A1 5/2023 Chell et al.
2023/0183684 A1 6/2023 Gallant et al.
2023/0183785 A1 6/2023 Frisen et al.
2023/0194469 A1 6/2023 Tentori et al.
2023/0194470 A1 6/2023 Kim et al.
2023/0203478 A1 6/2023 Kim et al.
2023/0212650 A1 7/2023 Chew et al.
2023/0212655 A1 7/2023 Chee
2023/0212656 A1 7/2023 Chow et al.
2023/0220368 A1 7/2023 Kim
2023/0220454 A1 7/2023 Bent et al.
2023/0220455 A1 7/2023 Galonska et al.
2023/0227811 A1 7/2023 Dadhwal
2023/0228762 A1 7/2023 Uytingco et al.
2023/0242973 A1 8/2023 Frisen et al.
2023/0242976 A1 8/2023 Tentori et al.
2023/0265488 A1 8/2023 Gohil et al.
2023/0265489 A1 8/2023 Uytingco et al.
2023/0265491 A1 8/2023 Tentori et al.
2023/0267625 A1 8/2023 Tentori et al.
2023/0279474 A1 9/2023 Katiraee
2023/0279477 A1 9/2023 Kvastad et al.
2023/0279481 A1 9/2023 Marrache et al.
2023/0287399 A1 9/2023 Gallant et al.
2023/0287475 A1 9/2023 Chell et al.
2023/0287481 A1 9/2023 Katsori et al.
2023/0295699 A1 9/2023 Sukovich et al.
2023/0295722 A1 9/2023 Bharadwaj
2023/0304072 A1 9/2023 Gohil et al.
2023/0304074 A1 9/2023 Chee et al.
2023/0304078 A1 9/2023 Frisen et al.
2023/0313279 A1 10/2023 Giacomello et al.
2023/0323340 A1 10/2023 Dadhwal
2023/0323434 A1 10/2023 Yin et al.
2023/0323436 A1 10/2023 Chee
2023/0323447 A1 10/2023 Schnall-Levin et al.
2023/0323453 A1 10/2023 Stoeckius
2023/0332138 A1 10/2023 Kim et al.
2023/0332211 A1 10/2023 Chee
2023/0332212 A1 10/2023 Chew et al.
2023/0332227 A1 10/2023 Ramachandran Iyer
2023/0332247 A1 10/2023 Singh et al.
2023/0351619 A1 11/2023 Tentori et al.
2023/0358733 A1 11/2023 Chee
2023/0366008 A1 11/2023 Chew et al.
2023/0383285 A1 11/2023 Kim et al.
2023/0383344 A1 11/2023 Stoeckius
2023/0392204 A1 12/2023 Chell et al.
2023/0393071 A1 12/2023 Bava
2023/0407404 A1 12/2023 Baumgartner et al.
2023/0416807 A1 12/2023 Chee
2023/0416808 A1 12/2023 Sukovich et al.
2023/0416850 A1 12/2023 Singh et al.
2024/0002931 A1 1/2024 Bava
2024/0011081 A1 1/2024 Chee
2024/0011090 A1 1/2024 Chew et al.
2024/0018572 A1 1/2024 Mignardi
2024/0018575 A1 1/2024 Gallant et al.
2024/0018589 A1 1/2024 Schnall-Levin et al.
2024/0026445 A1 1/2024 Ramachandran Iyer et al.
2024/0033743 A1 2/2024 Tentori et al.
2024/0035937 A1 2/2024 Cox et al.
2024/0043908 A1 2/2024 Chew et al.
2024/0043925 A1 2/2024 Bent et al.
2024/0052343 A1 2/2024 Gallant et al.
2024/0053351 A1 2/2024 Uytingco et al.
2024/0060115 A1 2/2024 Chee et al.
2024/0067953 A1 2/2024 Mikkelsen et al.
2024/0068016 A1 2/2024 Frisen et al.
2024/0068017 A1 2/2024 Lundeberg et al.
2024/0076723 A1 3/2024 Mignardi
2024/0080346 A1 3/2024 Engblom et al.
2024/0084365 A1 3/2024 Frisen et al.
2024/0084366 A1 3/2024 Chee
2024/0084383 A1 3/2024 Ramachandran Iyer et al.
2024/0093274 A1 3/2024 Frisen et al.
2024/0093290 A1 3/2024 Stahl et al.
2024/0110228 A1 4/2024 Uytingco et al.
2024/0124933 A1 4/2024 Chell et al.
2024/0125772 A1 4/2024 Delaney et al.
2024/0141327 A1 5/2024 Kim et al.
2024/0158838 A1 5/2024 Alvarado Martinez et al.
2024/0175080 A1 5/2024 Galonska et al.
2024/0182968 A1 6/2024 Bava
2024/0191286 A1 6/2024 Boutet et al.
2024/0200121 A1 6/2024 Boutet
2024/0209425 A1 6/2024 Yin et al.
2024/0218427 A1 7/2024 Sukovich et al.
2024/0218432 A1 7/2024 Mielinis
2024/0219701 A1 7/2024 Tentori et al.
2024/0253036 A1 8/2024 Kim et al.
2024/0263218 A1 8/2024 Katiraee et al.
2024/0271190 A1 8/2024 Stoeckius et al.
2024/0271195 A1 8/2024 Mikhaiel et al.
2024/0279712 A1* 8/2024 Fan .................. B01L 3/502707
2024/0279747 A1 8/2024 Williams
2024/0287600 A1 8/2024 Iyer et al.
2024/0294971 A1 9/2024 Galonska
2024/0294974 A1 9/2024 Galonska et al.
2024/0294975 A1 9/2024 Lin et al.
2024/0301488 A1 9/2024 Stoeckius
2024/0301489 A1 9/2024 Chew et al.
2024/0360494 A1 10/2024 Costa et al.
2024/0368711 A1 11/2024 Giacomello et al.

(56) References Cited

U.S. PATENT DOCUMENTS

| | | | |
|---|---|---|---|
| 2024/0377297 | A1 | 11/2024 | Cox et al. |
| 2024/0385088 | A1 | 11/2024 | Kim et al. |
| 2024/0392349 | A1 | 11/2024 | Frisen et al. |
| 2024/0392351 | A1 | 11/2024 | Chee |
| 2024/0392352 | A1 | 11/2024 | Stahl et al. |
| 2024/0392353 | A1 | 11/2024 | Engblom et al. |
| 2024/0401109 | A1 | 12/2024 | Kim et al. |
| 2024/0401117 | A1 | 12/2024 | Bava |
| 2024/0401118 | A1 | 12/2024 | Tentori et al. |
| 2024/0404301 | A1 | 12/2024 | Li et al. |
| 2024/0408593 | A1 | 12/2024 | Kim et al. |
| 2024/0416315 | A1 | 12/2024 | Bava |
| 2024/0417783 | A1 | 12/2024 | Chew et al. |
| 2024/0417784 | A1 | 12/2024 | Sukovich et al. |
| 2025/0002980 | A1 | 1/2025 | Tentori et al. |
| 2025/0002982 | A1 | 1/2025 | Stoeckius et al. |
| 2025/0003956 | A1 | 1/2025 | Delaney et al. |
| 2025/0019689 | A1 | 1/2025 | Galonska et al. |
| 2025/0019749 | A1 | 1/2025 | Katiraee et al. |
| 2025/0066762 | A1 | 2/2025 | Man et al. |
| 2025/0066770 | A1 | 2/2025 | Costa |
| 2025/0073719 | A1 | 3/2025 | Cox et al. |
| 2025/0075261 | A1 | 3/2025 | Kim |
| 2025/0101501 | A1 | 3/2025 | Chee |
| 2025/0101502 | A1 | 3/2025 | Chee |
| 2025/0101504 | A1 | 3/2025 | Nagendran et al. |
| 2025/0122564 | A1 | 4/2025 | Mignardi et al. |
| 2025/0122565 | A1 | 4/2025 | Schnall-Levin et al. |
| 2025/0129412 | A1 | 4/2025 | Uytingco et al. |
| 2025/0129421 | A1 | 4/2025 | Schnall-Levin et al. |
| 2025/0137043 | A1 | 5/2025 | Tentori |
| 2025/0145984 | A1 | 5/2025 | Ma et al. |
| 2025/0146057 | A1 | 5/2025 | Schnall-Levin et al. |
| 2025/0146058 | A1 | 5/2025 | Tentori |
| 2025/0146071 | A1 | 5/2025 | Schnall-Levin et al. |
| 2025/0146072 | A1 | 5/2025 | Schnall-Levin et al. |
| 2025/0154565 | A1 | 5/2025 | Chee |
| 2025/0154566 | A1 | 5/2025 | Chee |
| 2025/0154567 | A1 | 5/2025 | Chee |
| 2025/0154568 | A1 | 5/2025 | Frisen et al. |
| 2025/0154569 | A1 | 5/2025 | Stoeckius et al. |
| 2025/0154571 | A1 | 5/2025 | Ramachandran Iyer et al. |
| 2025/0154588 | A1 | 5/2025 | Ramachandran Iyer et al. |
| 2025/0155446 | A1 | 5/2025 | Uytingco et al. |
| 2025/0163501 | A1 | 5/2025 | Singh et al. |
| 2025/0163509 | A1 | 5/2025 | Daugharthy et al. |
| 2025/0171833 | A1 | 5/2025 | Frisen et al. |
| 2025/0171848 | A1 | 5/2025 | Chell et al. |
| 2025/0179475 | A1 | 6/2025 | Borgstrom et al. |
| 2025/0182305 | A1 | 6/2025 | Tentori et al. |
| 2025/0182503 | A1 | 6/2025 | Li et al. |
| 2025/0188526 | A1 | 6/2025 | Sukovich et al. |
| 2025/0189483 | A1 | 6/2025 | Kim et al. |
| 2025/0197847 | A1 | 6/2025 | Kim et al. |
| 2025/0197938 | A1 | 6/2025 | Bjorninen |
| 2025/0207125 | A1 | 6/2025 | Gupta et al. |
| 2025/0207182 | A1 | 6/2025 | Chee |
| 2025/0207183 | A1 | 6/2025 | Chee |
| 2025/0207195 | A1 | 6/2025 | Chell et al. |
| 2025/0208115 | A1 | 6/2025 | Bent |
| 2025/0215482 | A1 | 7/2025 | Mignardi et al. |
| 2025/0215484 | A1 | 7/2025 | Ramachandran Iyer et al. |
| 2025/0216300 | A1 | 7/2025 | Delaney et al. |
| 2025/0216303 | A1 | 7/2025 | Cox et al. |
| 2025/0223633 | A1 | 7/2025 | Frenz et al. |
| 2025/0230487 | A1 | 7/2025 | Chee et al. |
| 2025/0230498 | A1 | 7/2025 | Katiraee |
| 2025/0250621 | A1 | 8/2025 | Galonska et al. |
| 2025/0250632 | A1 | 8/2025 | Mignardi et al. |
| 2025/0257393 | A1 | 8/2025 | Katiraee et al. |
| 2025/0263791 | A1 | 8/2025 | Bava |
| 2025/0264411 | A1 | 8/2025 | Bava |
| 2025/0283154 | A1 | 9/2025 | Ramachandran Iyer et al. |
| 2025/0283157 | A1 | 9/2025 | Uytingco et al. |
| 2025/0297308 | A1 | 9/2025 | Tentori |
| 2025/0313890 | A1 | 10/2025 | Lundeberg et al. |
| 2025/0313892 | A1 | 10/2025 | Stoeckius |
| 2025/0340932 | A1 | 11/2025 | Chee |
| 2025/0340933 | A1 | 11/2025 | Giacomello et al. |
| 2025/0354931 | A1 | 11/2025 | Shah et al. |
| 2025/0369037 | A1 | 12/2025 | Gupta |
| 2025/0376676 | A1 | 12/2025 | Kim et al. |
| 2025/0376719 | A1 | 12/2025 | Shah |
| 2025/0382665 | A1 | 12/2025 | Frenz et al. |
| 2026/0002202 | A1 | 1/2026 | Schnall-Levin et al. |
| 2026/0009784 | A1 | 1/2026 | Stoeckius |
| 2026/0015653 | A1 | 1/2026 | Chew et al. |
| 2026/0022419 | A1 | 1/2026 | Bent et al. |
| 2026/0035740 | A1 | 2/2026 | Chee |
| 2026/0049349 | A1 | 2/2026 | Gallant et al. |
| 2026/0055443 | A1 | 2/2026 | Tentori et al. |
| 2026/0071262 | A1 | 3/2026 | Yin et al. |
| 2026/0103754 | A1 | 4/2026 | Schnall-Levin et al. |
| 2026/0117286 | A1 | 4/2026 | Katiraee et al. |
| 2026/0117289 | A1 | 4/2026 | Kim |
| 2026/0117298 | A1 | 4/2026 | Doddridge |
| 2026/0117299 | A1 | 4/2026 | Kim et al. |
| 2026/0117302 | A1 | 4/2026 | Chell et al. |
| 2026/0124615 | A1 | 5/2026 | Kim et al. |
| 2026/0132449 | A1 | 5/2026 | Galonska et al. |
| 2026/0132451 | A1 | 5/2026 | Ramachandran Iyer et al. |
| 2026/0146280 | A1 | 5/2026 | Kuhnemund et al. |
| 2026/0185146 | A1 | 7/2026 | Tentori et al. |
| 2026/0185147 | A1 | 7/2026 | Tentori et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| EP | 1782737 | 5/2007 |
| EP | 1910562 | 4/2008 |
| EP | 1923471 | 5/2008 |
| EP | 1929039 | 6/2008 |
| EP | 2002017 | 12/2008 |
| EP | 2130913 | 12/2009 |
| EP | 2292788 | 3/2011 |
| EP | 2302070 | 3/2011 |
| EP | 2580351 | 4/2013 |
| EP | 2881465 | 6/2015 |
| EP | 3013984 | 5/2016 |
| EP | 3207134 | 7/2019 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 1998/044151 | 10/1998 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |

(56) References Cited

FOREIGN PATENT DOCUMENTS

| | | |
|---|---|---|
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/113804 | 12/2005 |
| WO | WO 2006/020515 | 2/2006 |
| WO | WO 2006/124771 | 11/2006 |
| WO | WO 2006/137733 | 12/2006 |
| WO | WO 2007/037678 | 4/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2008/093098 | 8/2008 |
| WO | WO 2009/032167 | 3/2009 |
| WO | WO 2009/036525 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/127006 | 10/2011 |
| WO | WO 2011/155833 | 12/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/140224 | 10/2012 |
| WO | WO 2012/159089 | 11/2012 |
| WO | WO 2013/022807 | 2/2013 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2013/192292 | 12/2013 |
| WO | WO 2014/044724 | 3/2014 |
| WO | WO 2014/060483 | 4/2014 |
| WO | WO 2014/066179 | 5/2014 |
| WO | WO 2014/071361 | 5/2014 |
| WO | WO 2014/130576 | 8/2014 |
| WO | WO 2014/144713 | 9/2014 |
| WO | WO 2014/152397 | 9/2014 |
| WO | WO 2014/210223 | 12/2014 |
| WO | WO 2014/210353 | 12/2014 |
| WO | WO 2015/031691 | 3/2015 |
| WO | WO 2015/057319 | 4/2015 |
| WO | WO 2015/069374 | 5/2015 |
| WO | WO 2015/094861 | 6/2015 |
| WO | WO 2015/122967 | 8/2015 |
| WO | WO 2015/161173 | 10/2015 |
| WO | WO 2016/057552 | 4/2016 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |

| | | |
|---|---|---|
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/144338 | 8/2017 |
| WO | WO 2017/156336 | 9/2017 |
| WO | WO 2017/184984 | 10/2017 |
| WO | WO 2017/192633 | 11/2017 |
| WO | WO 2018/023068 | 2/2018 |
| WO | WO 2018/026873 | 2/2018 |
| WO | WO 2018/045181 | 3/2018 |
| WO | WO 2018/064640 | 4/2018 |
| WO | WO 2018/085599 | 5/2018 |
| WO | WO 2018/089550 | 5/2018 |
| WO | WO 2018/091676 | 5/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2018/217862 | 11/2018 |
| WO | WO 2019/023214 | 1/2019 |
| WO | WO 2019/032760 | 2/2019 |
| WO | WO 2019/068880 | 4/2019 |
| WO | WO 2019/089836 | 5/2019 |
| WO | WO 2019/089851 | 5/2019 |
| WO | WO 2019/113457 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/222523 | 11/2019 |
| WO | WO 2019/241290 | 12/2019 |
| WO | WO 2020/028194 | 2/2020 |
| WO | WO 2020/041148 | 2/2020 |
| WO | WO 2020/047002 | 3/2020 |
| WO | WO 2020/047010 | 3/2020 |
| WO | WO 2020/053655 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/067514 | 4/2021 |
| WO | WO 2021/091611 | 5/2021 |
| WO | WO 2021/092433 | 5/2021 |
| WO | WO 2021/097255 | 5/2021 |
| WO | WO 2021/102003 | 5/2021 |
| WO | WO 2021/102005 | 5/2021 |
| WO | WO 2021/102039 | 5/2021 |
| WO | WO 2021/116715 | 6/2021 |
| WO | WO 2021/119320 | 6/2021 |

(56) References Cited

FOREIGN PATENT DOCUMENTS

| | | |
|---|---|---|
| WO | WO 2021/133842 | 7/2021 |
| WO | WO 2021/133845 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/247593 | 12/2021 |
| WO | WO 2021/252499 | 12/2021 |
| WO | WO 2021/252576 | 12/2021 |
| WO | WO 2021/252591 | 12/2021 |
| WO | WO 2021/252747 | 12/2021 |
| WO | WO 2021/263111 | 12/2021 |
| WO | WO 2022/025965 | 2/2022 |
| WO | WO 2022/032195 | 2/2022 |
| WO | WO 2022/060798 | 3/2022 |
| WO | WO 2022/060953 | 3/2022 |
| WO | WO 2022/061150 | 3/2022 |
| WO | WO 2022/061152 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2011/019964 | 6/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/015913 | 11/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/034739 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/130019 | 7/2023 |
| WO | WO 2023/147355 | 8/2023 |
| WO | WO 2023/150098 | 8/2023 |
| WO | WO 2023/150163 | 8/2023 |
| WO | WO 2023/150171 | 8/2023 |
| WO | WO 2023/150763 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |
| WO | WO 2024/238900 | 11/2024 |
| WO | WO 2024/254316 | 12/2024 |
| WO | WO 2025/029605 | 2/2025 |
| WO | WO 2025/029627 | 2/2025 |
| WO | WO 2025/043076 | 2/2025 |
| WO | WO 2025/072119 | 4/2025 |
| WO | WO 2025/090912 | 5/2025 |
| WO | WO 2025/096581 | 5/2025 |
| WO | WO 2025/101864 | 5/2025 |
| WO | WO 2026/024934 | 1/2026 |

OTHER PUBLICATIONS

Kuhn et al., "A novel, high-performance random array platform for quantitative gene expression profiling," Genome Res, 2004, 14:2347-2356.

Kishi et al., "Light-Seq: light-directed in situ barcoding of biomolecules in fixed cells and tissues for spatially indexed sequencing," Nature Methods, Oct. 10, 2022, 19(11):1393-1402.

Howell et al., "iFRET: An Improved Fluorescence System for DNA-Melting Analysis," Genome Research, 2002, 12: 1401-1407.

Nam et al., "Nanoparticle-Based Bio-Bar Codes for the Ultrasensitive Detection of Proteins," Science, Sep. 26, 2003, 301(5641):1884-1886.

Redmond et al., "Single-cell TCRseq: paired recovery of entire T-cell alpha and beta chain transcripts in T-cell receptors from single-cell RNAseq," Genome Med, 2016, 8:80, 12 pages.

[No Author Listed], "Chromium Next GEM Single Cell 3' Reagent Kits v3.1—User Guide," 10x Genomics, Document No. CG000204, Nov. 2019, 58 pages.

[No Author Listed], "Chromium Next GEM Single Cell 3' Reagent Kits v3.1 (Dual Index)—User Guide," 10x Genomics, Mar. 2021, Document No. CG000315, 61 pages.

[No Author Listed], "HuSNP Mapping Assay User's Manual, " Affymetrix Part No. 90094 (Affymetrix, Santa Clara, Calif.), GeneChip, 2000, 104 pages.

[No Author Listed], "Microarray technologies have excellent possibilities in genomics-related researches," Science Tools From Amersham Pharmacia Biotech, 1998, 3(4): 8 pages (with English Translation).

[No Author Listed], "Proseek® Multiplex 96x96 User Manual," Olink Proteomics, Olink Bioscience, Uppsala, Sweden, 2017, 20 pages.

10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 42 pages.

10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw5lee9/6a2ac61cf6388a72564eeb96bc294967/CG000238_VisiumSpatialTissueOptimizationUserGuide_Rev_A.pdf>, 46 pages.

10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0cH17rEk0UXwd19It/e54d99fb08a8f1500aba503005a04a56/CG000238_VisiumSpatialTissueOptimizationUserGuide_RevD.pdf>, 43 pages.

10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVhalpexR/8baa08d9007157592b65b2cdc7130990/CG000239_VisiumSpatialGeneExpression_UserGuide_RevD.pdf>, 69 pages.

10xGenomics.com, [online], "Visium Spatial Gene Expression Reagent Kits—User Guide," Oct. 2020, retrieved on Dec. 28, 2021, retrieved

(56) References Cited

OTHER PUBLICATIONS from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Adessi et al., "Solid phase DNA amplification: characterisation of primer attachment and amplification mechanisms, " Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al., "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes-Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates, " Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell Cut&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Boeke et al., "Transcription and reverse transcription of retrotransposons," Annu Rev Microbiol, 1989, 43:403-34.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4, " Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections, " Biotechniques, 1998, 24(1):92-100.

(56) References Cited

OTHER PUBLICATIONS

Caliari et al., "A practical guide to hydrogels for cell culture," Nat Methods., Apr. 2016, 13(5):405-14.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al., "DNA hybridization detection in a microfluidic Channel using two fluorescently labelled nucleic acid probes, " Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Fusion protein linkers: Property, design and functionality," Advanced Drug Delivery Reviews, Oct. 15, 2013, 65(10):1357-1369, 32 pages.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "μCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cho et al., "Seq-Scope: Submicrometer-resolution spatial transcriptomics for single cell and subcellular studies," bioRxiv, Jan. 27, 2021, retrieved from URL <https://www.biorxiv.org/node/1754517.abstract>, 50 pages.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.
Codeluppi et al., "Spatial organization of the somatosensory cortex revealed by osmFISH," Nature Methods, Nov. 2018, 15:932-935.
Colegio et al., "In vitro transposition system for efficient generation of random mutants of Campylobacter jejuni," J Bacteriol., Apr. 2001, 183(7):2384-8.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Craig, "Transposon Tn7" Curr Top Microbiol Immunol., 1996, 204:27-48.
Craig, "V(D)J recombination and transposition: closer than expected," Science, Mar. 1996, 271(5255):1512, 1 page.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60-6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Deng et al., "Spatial Epigenome Sequencing at Tissue Scale and Cellular Level," BioRxiv, Mar. 2021, 40 pages.
Devine et al., "Efficient integration of artificial transposons into plasmid targets in vitro: a useful tool for DNA mapping, sequencing and genetic analysis," Nucleic Acids Res., Sep. 1994, 22(18):3765-72.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Duncan et al., "Affinity chromatography of a sequence-specific DNA binding protein using Teflon-linked oligonucleotides," Anal. Biochem., 1988, 169(1):104-108.
Eberwine, "Amplification of mRNA populations using aRNA generated from immobilized oligo(dT)-T7 primed cDNA," BioTechniques, 1996, 20(4):584-91.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles, " Proc. Natl. Acad. Sci., 1995, 92(10):4641-4645.
Flanigon et al., "Multiplex protein detection with DNA readout via mass spectrometry," N. Biotechnol., 2013, 30(2):153-158.

(56) References Cited

OTHER PUBLICATIONS

Fluidigm, “Equivalence of Imaging Mass Cytometry and Immunofluorescence on FFPE Tissue Sections,” White Paper, 2017, 12 pages.
Fodor et al., “Light-directed, spatially addressable parallel chemical synthesis,” Science, 1995, 251(4995):767-773.
Forster et al., “A human gut bacterial genome and culture collection for improved metagenomic analyses,” Nature Biotechnology, 2019, 37(2):186-192.
Frese et al., “Formylglycine aldehyde Tag—protein engineering through a novel post-translational modification,” ChemBioChem., 2009, 10(3):425-27.
Fu et al., “Continuous Polony Gels for Tissue Mapping with High Resolution and RNA Capture Efficiency,” bioRxiv, 2021, 20 pages.
Fu et al., “Counting individual DNA molecules by the stochastic attachment of diverse labels,” PNAS, 2011, 108(22):9026-9031.
Fu et al., “Repeat subtraction-mediated sequence capture from a complex genome,” Plant J., Jun. 2010, 62(5): 898-909.
Fullwood et al., “Next-generation DNA sequencing of paired-end tags (PET) for transcriptome and genome analyses,” Genome Res., 2009, 19(4):521-532.
Ganguli et al., “Pixelated spatial gene expression analysis from tissue,” Nat Commun., Jan. 2018, 9(1):202, 9 pages.
Gansauge et al., “Single-stranded DNA library preparation from highly degraded DNA using T4 DNA ligase,” Nucleic Acids Res., Jun. 2017, 45(10):e79, 10 pages.
Gao et al., “A highly homogeneous expansion microscopy polymer composed of tetrahedron-like monomers,” bioRxiv, Oct. 22, 2019, 23 pages (Preprint).
Gao et al., “Q&A: Expansion microscopy,” BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., “Excess dNTPs minimize RNA hydrolysis during reverse transcription,” Biotechniques, Nov. 2002, 33(5):984, 986, 988, 990.
Gilar et al., “Study of phosphorothioate-modified oligonucleotide resistance to 3'-exonuclease using capillary electrophoresis,” J Chromatogr B Biomed Sci Appl., Aug. 28, 1998, 714(1):13-20.
Gill et al., “Nucleic acid isothermal amplification technologies: a review,” Nucleosides Nucleotides Nucleic Acids, Mar. 2008, 27(3):224-43.
Glass et al., “SIMPLE: a sequential immunoperoxidase labeling and erasing method,” J. Histochem. Cytochem., Oct. 2009, 57(10):899-905.
Gloor, “Gene targeting in *Drosophila*,” Methods Mol Biol., 2004, 260:97-114.
Gnanapragasam, “Unlocking the molecular archive: the emerging use of formalin-fixed paraffin-embedded tissue for biomarker research in urological cancer,” BJU International, 2009, 105(2):274-278.
Goh et al., “Highly Specific Multiplexed RNA Imaging in Tissues With Split-FISH,” Nat Methods, Jun. 15, 2020, 17(7):689-693, 21 pages.
Goldkorn et al., “A simple and efficient enzymatic method for covalent attachment of DNA to cellulose. Application for hybridization-restriction analysis and for in vitro synthesis of DNA probes,” Nucleic Acids Res., 1986, 14(22):9171-9191.
Goransson et al., “A single molecule array for digital targeted molecular analyses,” Nucleic Acids Res., Nov. 25, 2009, 37(1):e7, 9 pages.
Goryshin et al., “Tn5 in vitro transposition,” J Biol Chem., Mar. 1998, 273(13):7367-74.
Gracia Villacampa et al., “Genome-wide Spatial Expression Profiling in FFPE Tissues,” bioRxiv, 2020, pp. 38 pages.
Grokhovsky, “Specificity of DNA cleavage by ultrasound,” Molecular Biology, 2006, 40(2):276-283.
Grünweller et al., “Locked Nucleic Acid Oligonucleotides,” BioDrugs, Jul. 2007, 21(4): 235-243.
Gu et al., “Multiplex single-molecule interaction profiling of DNA-barcoded proteins,” Nature, Sep. 21, 2014, 515:554-557.
Gu et al., “Protein tag-mediated conjugation of oligonucleotides to recombinant affinity binders for proximity ligation,” N Biotechnol., 2013, 30(2):144-152.
Gunderson et al., “Decoding randomly ordered DNA arrays,” Genome Research, 2004, 14(5):870-877.
Guo et al., “Direct fluorescence analysis of genetic polymorphisms by hybridization with oligonucleotide arrays on glass supports,” Nucleic Acids Res., Dec. 1994, 22(24):5456-65.
Gupta et al., “Single-cell isoform RNA sequencing characterizes isoforms in thousands of cerebellar cells,” Nature Biotechnol., Oct. 2018, 36:1197-1202.
Hafner et al., “Identification of microRNAs and other small regulatory RNAs using cDNA library sequencing,” Methods, Jan. 2008, 44(1):3-12.
Hahnke et al., “Striptease on glass: validation of an improved stripping procedure for in situ microarrays,” J Biotechnol., Jan. 2007, 128(1):1-13.
Hamaguchi et al., “Direct reverse transcription-PCR on oligo(dT)-immobilized polypropylene microplates after capturing total mRNA from crude cell lysates,” Clin Chem., Nov. 1998, 44(11):2256-63.
Hanauer et al., “Separation of nanoparticles by gel electrophoresis according to size and shape,” Nano Lett., Sep. 2007, 7(9):2881-5.
Hardenbol et al., “Highly multiplexed molecular inversion probe genotyping: over 10,000 targeted SNPs genotyped in a single tube assay,” Genome Res., Feb. 2005, 15(2):269-75.
Hardenbol et al., “Multiplexed genotyping with sequence-tagged molecular inversion probes,” Nature Biotechnol., Jun. 2003, 21(6):673-678.
Hayes et al., “Electrophoresis of proteins and nucleic acids: I-Theory,” BMJ, Sep. 1989, 299(6703):843-6.
He et al., “In situ synthesis of protein arrays,” Current Opinion in Biotechnology, 2008, 19(1):4-9.
He et al., “Printing protein arrays from DNA arrays,” Nature Methods, 2008, 5(2):175-77.
He, “Cell-free protein synthesis: applications in proteomics and biotechnology,” New Biotechnology, 2008, 25(2-3):126-132.
Healy, “Nanopore-based single-molecule DNA analysis,” Nanomedicine (Lond), Aug. 2007, 2(4):459-81.
Hejatko et al., “In situ hybridization technique for mRNA detection in whole mount *Arabidopsis* samples,” Nature Protocols, 2006, 1(4):1939-1946.
Hessner et al., “Genotyping of factor V G1691A (Leiden) without the use of PCR by invasive cleavage of oligonucleotide probes,” Clin Chem., Aug. 2000, 46(8 Pt 1):1051-6.
Hiatt et al., “Parallel, tag-directed assembly of locally derived short sequence reads,” Nature Methods, 2010, 7(2):119-25.
Ho et al., “Bacteriophage T4 RNA ligase 2 (gp24.1) exemplifies a family of RNA ligases found in all phylogenetic domains,” PNAS, Oct. 2002, 99(20):12709-14.
Ho et al., “Characterization of an ATP-Dependent DNA Ligase Encoded by Chlorella Virus PBCV-1,” Journal of Virology, Mar. 1997, 71(3):1931-1937.
Hoffman et al., “Formaldehyde crosslinking: a tool for the study of chromatin complexes,” J Biol Chem., Oct. 2015, 290(44):26404-11.
Hsuih et al., “Novel, Ligation-Dependent PCR Assay for Detection of Hepatitis C Virus in Serum,” Journal of Clinical Microbiology, Mar. 1996, 34(3):501-507.
Hu et al., “High reproducibility using sodium hydroxide-stripped long oligonucleotide DNA microarrays,” Biotechniques, Jan. 2005, 38(1):121-4.
Hughes et al., “Microfluidic Western blotting,” PNAS, Dec. 2012, 109(52):21450-21455.
Hycultbiotech.com, [online], “Immunohistochemistry, Paraffin” Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., “In vitro transposition of transposon Tn3,” J Biol. Chem., Nov. 1990, 265(31):18829-32, Abstract.

(56) References Cited

OTHER PUBLICATIONS

Illumina.com [online], "Ribo-ZeroR rRNA Removal Kit Reference Guide," Aug. 2016, retrieved on Apr. 26, 2022, retrieved from URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Jucá et al., "Effect of dimethyl sulfoxide on reverse transcriptase activity," Braz. J. Med. Biol. Res., Mar. 1995, 28(3):285-90.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "Cut&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Korbel et al., "Paired-end mapping reveals extensive structural variation in the human genome," Science, 2007, 318(5849):420-426.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA—protein fusions: covalent protein—gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Fluorescent in situ sequencing (FISSEQ) of RNA for gene expression profiling in intact cells and tissues," Nature Protocols, 2015, 10(3):442-458.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Li et al., "A new GSH-responsive prodrug of 5-aminolevulinic acid for photodiagnosis and photodynamic therapy of tumors," European Journal of Medicinal Chemistry, Nov. 2019, 181:111583, 9 pages.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.
Liu et al., "High-Spatial-Resolution Multi-Omics Sequencing via Deterministic Barcoding in Tissue," Cell, Nov. 13, 2020, 183(6):1665-1681, 36 pages.
Liu et al., "Spatial transcriptome sequencing of FFPE tissues at cellular level," bioRxiv 788992, Oct. 14, 2020, 39 pages.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus, " Gene, 1991, 108(1):1-6.

(56) References Cited

OTHER PUBLICATIONS

Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved Cut&Run chromatin profiling tools," Elife, Jun. 2019, 8:e46314, 16 pages.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec. 1, 2001, 29(23):e118, 9 pages.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.

(56) References Cited

OTHER PUBLICATIONS

Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Ranki et al., "Sandwich hybridization as a convenient method for the detection of nucleic acids in crude samples," Gene, 1983, 21(1-2):77-85.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Salmén et al., "Barcoded solid-phase RNA capture for Spatial Transcriptomics profiling in mammalian tissue sections," Nature Protocols, Oct. 2018, 13(11):2501-2534.
Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.
Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A DNA microarray system for analyzing complex DNA samples using two-color fluorescent probe hybridization," Genome Res., Jul. 1996, 6(7):639-45.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Skipper et al., "DNA transposon-based gene vehicles—scenes from an evolutionary drive," J Biomed Sci., Dec. 2013, 20(1):92, 23 pages.
Slomovic et al., "Addition of poly(A) and poly(A)-rich tails during RNA degradation in the cytoplasm of human cells," Proc Natl Acad Sci USA, Apr. 2010, 107(16):7407-12.
Sountoulidis et al., "Scrinshot, a spatial method for single-cell resolution mapping of cell states in tissue sections," PLoS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sutherland et al., "Utility of formaldehyde cross-linking and mass spectrometry in the study of protein-protein interactions," J. Mass Spectrom., Jun. 2008, 43(6):699-715.
Takei et al., "Integrated Spatial Genomics Reveals Global Architecture of Single Nuclei," Nature, Jan. 27, 2021, 590(7845):344-350, 53 pages.

(56) References Cited

OTHER PUBLICATIONS

Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.
Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 RNA ligase 2 truncated active site mutants: improved tools for RNA analysis," BMC Biotechnol., Jul. 2011, 11:72, 14 pages.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Xia et al., "Spatial transcriptome profiling by MERFISH reveals subcellular RNA compartmentalization and cell cycle-dependent gene expression", Proceedings of the National Academy of Sciences, Sep. 2019, 116(39):19490-19499.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zhang et al., "A novel mechanism of transposon-mediated gene activation," PLoS Genet., Oct. 2009, 5(10):e1000689, 10 pages.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.

(56) References Cited

OTHER PUBLICATIONS

Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probest," Chem. Commun., 2013, 49:10013-10015.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Bibikova et al., "Quantitative gene expression profiling in formalin-fixed paraffin-embedded tissues using universal bead arrays," The American Journal of Pathology, Nov. 1, 2004, 165(5):1799-1807.
Choi et al., "Multiplexed detection of mRNA using porosity-tuned hydrogel microparticles," Analytical chemistry, Sep. 28, 2012, 84(21):9370-9378.
Fan et al., "A versatile assay for high-throughput gene expression profiling on universal array matrices," Genome Research, May 1, 2004, 14(5):878-885.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Sun et al., "Statistical Analysis of Spatial Expression Pattern for Spatially Resolved Transcriptomic Studies," Nature Methods, Jan. 27, 2020, 17(2): 193-200.
Svensson et al., "SpatialDE: identification of spatially variable genes," Nature Methods, May 2018, 15:343-346, 15 pages.
Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.
Belton et al., "Hi-C: A comprehensive technique to capture the conformation of genomes," Methods, Nov. 2012, 58(3):268-276, 16 pages.
Bentzen et al., "Large-scale detection of antigen-specific T cells using peptide-MHC-I multimers labeled with DNA barcodes," Nat Biotechnol., Oct. 2016, 34(10):1037-1045, 12 pages.
Chen et al. "Arrayed profiling of multiple glycans on whole living cell surfaces." Analytical chemistry, Oct. 15, 2013, 85(22):11153-11158.
Fan et al., "Illumina Universal Bead Arrays," Methods in Enzymology, 2006, 410:57-73.
Hadrup et al., "Parallel detection of antigen-specific T-cell responses by multidimensional encoding of MHC multimers," Nat. Methods., Jul. 2009, 6(7), 520-526.
Hobro et al, "An evaluation of fixation methods: Spatial and compositional cellular changes observed by Raman imaging," Vibrational Spectroscopy, Jul. 2017, 91:31-45.
Landegren et al., "A Ligase-Mediated Gene Detection Technique," Science, 1988, 241(4869):1077-1080.
Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Schmidl et al., "ChIPmentation: fast, robust, low-input ChIP-seq for histones and transcription factors," Nature Methods, Oct. 2015, 12:963-965.
Su et al., "Restriction enzyme selection dictates detection range sensitivity in chromatin conformation capture-based variant-to-gene mapping approaches," bioRxiv, Dec. 15, 2020, 22 pages.
Asp et al., "A spatiotemporal organ-wide gene expression and cell atlas of the developing human heart," Cell, Dec. 12, 2019, 179(7):1647-1660.
10x Genomics, "Assay Scheme and Configuration of Chromium™ Single Cell V(D)J Libraries," 10x Genomics, CG000109 Rev D, 2017, 10 pages.
Deng et al., "Spatial-ATAC-seq: spatially resolved chromatin accessibility profiling of tissues at genome scale and cellular level," bioRxiv, Jun. 7, 2021, retrieved from URL <https://www.biorxiv.org/content/10.1101/2021.06.06.447244v1>, 49 pages (Preprint).
Hong et al., "Cell Microarray Technologies for High-Throughput Cell-Based Biosensors," Sensors (Basel), Jun. 5, 2017, 17(6):1293.
Stickels et al., "Highly sensitive spatial transcriptomics at near-cellular resolution with Slide-seqV2," Nat Biotechnol., Mar. 2021, 39(3):313-319, 28 pages (Author Manuscript).

* cited by examiner

METHOD FOR TRANSPOSASE MEDIATED SPATIAL TAGGING AND ANALYZING GENOMIC DNA IN A BIOLOGICAL SAMPLE

CROSS-REFERENCE TO RELATED APPLICATIONS

This application claims priority to U.S. Provisional Patent Application No. 63/285,677, filed Dec. 3, 2021. The entire content of the foregoing application is incorporated herein by reference.

SEQUENCE LISTING

This application contains a Sequence Listing that has been submitted electronically as an XML file named 47706-0322001_SL_ST26.xml. The XML file, created on Dec. 1, 2022, is 3,772 bytes in size. The material in the XML file is hereby incorporated by reference in its entirety.

BACKGROUND

Cells within a tissue have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, signaling, and cross-talk with other cells in the tissue.

Spatial heterogeneity has been previously studied using techniques that typically provide data for a handful of analytes in the context of intact tissue or a portion of a tissue (e.g., tissue section), or provide significant analyte data from individual, single cells, but fails to provide information regarding the position of the single cells from the originating biological sample (e.g., tissue).

Chromatin structure can be different between cells in a biological sample or between biological samples from the same tissue. Assaying differences in accessible chromatin can be indicative of transcriptionally active sequences, e.g., genes, in a particular cell. Exemplary methods for assaying differences in accessible chromatin include, but are not limited to, nucleosome occupancy and methylome sequencing (NOMe-seq), assay for transposase-accessible chromatin using sequencing (ATAC-seq), DNase I hypersensitive sites sequencing (DNAse-seq), Hi-C sequencing, RNA-seq, bisulfate sequencing (BS-seq), DNA modification-dependent restriction endonuclease AbaSI coupled with sequencing (Aba-seq), chemical-labeling-enabled C-to-T conversion sequencing (CLEVER-seq), chromatin immunoprecipitation with massively parallel sequencing (ChIP-seq), cleavage under targets and release using nuclease (CUT & Run), cleavage under targets and tagmentation (CUT & Tag), scCUT & Tag, high-spatial-resolution chromatin modification state profiling by sequencing (hsrChST-seq), and single cell sequencing varieties thereof. Further understanding the transcriptionally active regions within chromatin will enable identification of which genes contribute to a cell's function and/or phenotype.

SUMMARY

The present disclosure generally describes methods for spatially analyzing genomic DNA present in a biological sample.

Methods have been developed to study epigenomes, e.g., CUT & Run or CUT & Tag sequencing. These assays help identify regulators (e.g., cis regulators and/or trans regulators) that contribute to dynamic cellular phenotypes. While CUT & Run and CUT & Tag sequencing have been valuable in defining epigenetic variability within a cell population, conventional applications of these methods are limited in their ability to spatially resolve the two- and three-dimensional structures and associated genes that promote cellular variation. Although spatial methods are also known, additional and/or alternative methods are still needed. In particular, methods that can simultaneously assess epigenomes and gene expression in a tissue sample would be useful.

Thus, the present disclosure relates generally to the spatial tagging and analysis of nucleic acids. In some instances, provided herein are methods that utilize a transposome to fragment genomic DNA and to capture the fragmented DNA on a spatial array, thus revealing epigenomic insights regarding the structural features contributing to cellular regulation within the spatial context of a biological sample.

Provided herein are methods for determining location of accessible genomic DNA in a biological sample, the method comprising: (a) providing the biological sample on an array comprising a plurality of capture probes, wherein a capture probe of the plurality of capture probes comprises: (i) a spatial barcode and (ii) a capture domain; (b) adding an antibody specific to a chromatin protein in the biological sample and binding the antibody to the chromatin protein; (c) binding a transposome-binding moiety complex to the antibody, wherein the transposome-antibody-binding moiety complex comprises: (i) a transposase, (ii) an antibody-binding moiety, (iii) a first transposon end sequence comprising a splint sequence that is substantially complementary to a portion of a splint oligonucleotide, and (iv) a second transposon end sequence comprising a functional sequence; and (d) generating fragmented genomic DNA; (e) adding a plurality of splint oligonucleotides to the biological sample, wherein a portion of a splint oligonucleotide hybridizes to a portion of the capture domain; (f) hybridizing the splint sequence of the fragmented genomic DNA to the splint oligonucleotide hybridized to the capture domain; and (g) determining (i) the spatial barcode or a complement thereof, of the capture probe and (ii) all or part of a sequence of the fragmented genomic DNA, or a complement thereof, to determine the location of the accessible genomic DNA in the biological sample.

In some embodiments, steps (b) and (c) are performed at the same time, and wherein the antibody and the transposome-antibody-binding moiety are combined to form a multi-complex.

In some embodiments, the splint oligonucleotide comprises about 12 to about 40 nucleotides.

In some embodiments, step (b), through step (f) are performed at substantially the same time.

In some embodiments, the methods described herein further comprise ligating the splint sequence of the fragmented genomic DNA to the capture domain of the capture probe.

In some embodiments, the methods described herein further comprise gap filling and ligation between the 3' end of the transposon and the 5' end of the fragmented genomic DNA.

In some embodiments, the methods described herein further comprise extending the 3' end of the captured fragmented genomic DNA using the capture probe as a template, wherein the gap filling, ligation, and extension occur at the substantially the same time.

In some embodiments, the functional sequence of the second transposon end sequence comprises a primer sequence.

In some embodiments, the antibody-binding moiety is protein A, protein G, or functional derivatives thereof.

In some embodiments, the transposase is a Tn5 transposase enzyme, a Mu transposase enzyme, a Tn7 transposase enzyme, a *vibhar* species transposase, or functional derivatives thereof.

In some embodiments, the methods described herein further comprise extending a 3' end of the capture probe using the fragmented genomic DNA as a template, wherein the extending step is performed using a DNA polymerase having strand displacement activity.

In some embodiments, the methods described herein further comprise staining the biological sample, optionally wherein the staining comprises hematoxylin and eosin (H&E) staining or immunofluorescence staining.

In some embodiments, the biological sample is permeabilized prior to step (b), wherein permeabilization is chemical or enzymatic, and wherein the chemical permeabilization condition comprises a detergent, optionally wherein the detergent is one or more of NP-40, polysorbate-20, and digitonin.

In some embodiments, the enzymatic permeabilization condition comprises a protease of the group consisting of a pepsin, a collagenase, a proteinase K, or combinations thereof.

In some embodiments, the biological sample is a fresh tissue sample or section, a frozen tissue sample or section, or a fixed tissue sample or section.

In some embodiments, the fixed tissue sample or section is a formalin-fixed, paraffin embedded (FFPE) tissue sample or section.

In some embodiments, the capture probe further comprises a cleavage domain, one or more functional domains, a unique molecular identifier, or combinations thereof.

In some embodiments, the methods described herein further comprise determining the location of an mRNA in the biological sample, the method comprising: hybridizing the mRNA or a portion thereof to the capture domain; and determining (i) the spatial barcode or a complement thereof, and (ii) all or part of a sequence of the mRNA, or a complement thereof, and using the determined sequences of (i) and (ii) to determine the location of the mRNA in the biological sample.

In some embodiments, hybridizing the mRNA or a portion thereof to the capture domain is performed concurrent with or after step (b).

In some embodiments, determining (i) the spatial barcode or a complement thereof, and (ii) all or part of a sequence of the mRNA, or a complement thereof occurs concurrent with step (g).

In some embodiments, determining (i) spatial barcode or a complement thereof, and (ii) all or part of a sequence of the mRNA, or a complement thereof comprises sequencing.

Also provided herein are kits for determining the location of accessible genomic DNA in a biological sample comprising: (a) an array comprising a plurality of capture probes, wherein a capture probe of the plurality of capture probes comprises: (i) a spatial barcode and (ii) a capture domain; (b) a complex comprising: (i) an antibody-binding protein, (ii) a transposase, (iii) a first transposon end sequence comprising a splint sequence that is substantially complementary to a portion of a splint oligonucleotide, and (iv) a second transposon end sequence comprising a functional sequence; and (c) instructions for performing any one of the methods described herein.

Also provided herein are kits for determining abundance and location of accessible genomic DNA in a biological sample comprising: (a) an array comprising a plurality of capture probes, wherein a capture probe of the plurality of capture probes comprises: (i) a spatial barcode and (ii) a capture domain; (b) a multi-complex comprising: (i) an antibody-binding protein, (ii) a transposase, (iii) a first transposon end sequence comprising a splint sequence that is substantially complementary to a portion of a splint oligonucleotide, (iv) a second transposon end sequence comprising a functional sequence, and (v) an antibody that binds to a chromatin protein in the biological sample; and (c) instructions for performing any one of the methods described herein.

Also provided herein are compositions for determining abundance and/or location of accessible genomic DNA in a biological sample comprising: (a) an array comprising a plurality of capture probes, wherein a capture probe of the plurality of capture probes comprises: (i) a spatial barcode and (ii) a capture domain; (b) a complex comprising: (i) an antibody-binding protein, (ii) a transposase, (iii) a first transposon end sequence comprising a splint sequence that is substantially complementary to a portion of a splint oligonucleotide, and (iv) a second transposon end sequence; and (c) an antibody bound to a chromatin protein in the biological sample, wherein the antibody is additionally bound to the complex from step (b).

Also provided herein are methods for determining the location of accessible genomic DNA in a biological sample, the method comprising: (a) providing the biological sample on a first substrate; (b) binding an antibody specific to a chromatin protein in the biological sample to the chromatin protein; (c) binding a transposome-binding moiety complex to the antibody, wherein the transposome-antibody-binding moiety complex comprises: (i) a transposase, (ii) an antibody-binding moiety, (iii) a first transposon end sequence comprising a splint sequence that is substantially complementary to a portion of a splint oligonucleotide, and (iv) a second transposon end sequence comprising a functional sequence; and (d) generating fragmented genomic DNA; (e) aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain; (f) adding a plurality of splint oligonucleotides to the biological sample, wherein a portion of a splint oligonucleotide hybridizes to a portion of the capture domain; (g) hybridizing the splint sequence of the fragmented genomic DNA to the splint oligonucleotide hybridized to the capture domain; and (h) determining (i) the spatial barcode or a complement thereof, of the capture probe and (ii) all or part of a sequence of the fragmented genomic DNA, or a complement thereof, to determine the location of the accessible genomic DNA in the biological sample.

In some embodiments, the aligning comprises: mounting the first substrate on a first member of a support device, the first member configured to retain the first substrate; mounting the second substrate on a second member of the support device; applying a reagent medium to the first substrate and/or the second substrate; and operating an alignment mechanism of the support device to move the first member and/or the second member such that at least a portion of the biological sample is aligned with at least a portion of the array, and such that the portion of the biological sample and the portion of the array contact the reagent medium.

In some embodiments, the reagent medium comprises a permeabilization agent selected from trypsin, pepsin, elastase, or proteinase K.

In some embodiments, at least one of the first substrate and the second substrate further comprise a spacer disposed on the first substrate or the second substrate, wherein when at least the portion of the biological sample is aligned with at least a portion of the array such that the portion of the biological sample and the portion of the array contact the reagent medium, the spacer is disposed between the first substrate and the second substrate and is configured to maintain the reagent medium within a chamber formed by the first substrate, the second substrate, and the spacer, and to maintain a separation distance between the first substrate and the second substrate, wherein the spacer is positioned to surround an area on the first substrate on which the biological sample is disposed and/or the array disposed on the second substrate, wherein the area of the first substrate, the spacer, and the second substrate at least partially encloses a volume comprising the biological sample.

In some embodiments, steps (b) and (c) are performed at the same time, and the antibody and the transposome-antibody-binding moiety are combined to form a multi-complex.

In some embodiments, the transposase is a Tn5 transposase enzyme, a Mu transposase enzyme, a Tn7 transposase enzyme, a *vibhar* species transposase, or functional derivatives thereof.

Also provided herein are methods for determining abundance and/or location of accessible genomic DNA in a biological sample, the method comprising (a) providing the biological sample on an array comprising a plurality of capture probes, wherein a capture probe of the plurality of capture probes comprises: (i) a spatial barcode and (ii) a capture domain; (b) adding an antibody that binds to a chromatin protein; (c) binding a transposome-antibody-binding moiety complex to the antibody, thereby generating fragmented genomic DNA, wherein the transposome-antibody-binding moiety complex comprises: (i) a transposase, (ii) an antibody-binding moiety (iii) a first transposon end sequence comprising a splint sequence that is substantially complementary to a portion of a splint oligonucleotide, and (iv) a second transposon end sequence comprising a functional sequence; and (d) adding a plurality of splint oligonucleotides to the biological sample, wherein a portion of a splint oligonucleotide of the plurality of splint oligonucleotides hybridizes to a portion of the capture domain; (e) hybridizing the splint sequence of the fragmented genomic DNA to the splint oligonucleotide and hybridizing the splint oligonucleotide to the capture probe; (f) ligating the splint sequence of the fragmented genomic DNA to the capture domain; and (g) determining (i) all or part of a sequence of the spatial barcode or a complement thereof, and (ii) all or part of a sequence of the fragmented genomic DNA, or a complement thereof, and using the determined sequences of (i) and (ii) to determine the abundance and/or location of the accessible genomic DNA in the biological sample.

Also provided herein are methods for determining abundance and/or location of accessible genomic DNA in a biological sample, the method comprising: (a) providing the biological sample on an array comprising a plurality of capture probes, wherein a capture probe of the plurality of capture probes comprises: (i) a spatial barcode and (ii) a capture domain; (b) complexing an antibody that binds to a chromatin protein in the biological sample to a transposome-antibody-binding moiety complex, generating a multi-complex, wherein the multi-complex comprises: (i) a transposase, (ii) an antibody-binding moiety, (iii) the first transposon end sequence comprising a splint sequence that is substantially complementary to a portion of a splint oligonucleotide, (iv) the second transposon end sequence comprising a functional sequence, and (v) the antibody; and (c) adding the multi-complex to the biological sample, thereby generating fragmented genomic DNA; (d) adding a plurality of splint oligonucleotides to the biological sample, wherein a portion of a splint oligonucleotide of the plurality of splint oligonucleotides hybridizes to a portion of the capture domain; (e) hybridizing the splint sequence of the fragmented genomic DNA to the splint oligonucleotide and hybridizing the splint oligonucleotide to the capture probe, (f) ligating the transposon splint sequence of the fragmented genomic DNA to the capture domain; and (g) determining (i) all or part of a sequence of the spatial barcode or a complement thereof, and (ii) all or part of a sequence of the fragmented genomic DNA, or a complement thereof, and using the determined sequences of (i) and (ii) to determine the abundance and/or location of the accessible genomic DNA in the biological sample.

In some instances, the splint oligonucleotide comprises about 12 to about 40 nucleotides.

In some instances, step (b), step (c), step (d), and step (e) are performed at substantially the same time.

In some instances, the ligating utilizes a DNA ligase.

In some instances, any of the methods described herein further comprise performing gap filling and ligation between the 3' end of a transposon and a 5' end of a fragmented genomic DNA. In some instances, any of the methods described herein further comprise extending the 3' end of the captured fragmented genomic DNA using the capture probe as a template.

In some instances, the gap filling, ligation, and extension occur at the same time.

In some instances, the functional sequence of the second transposon end sequence is a primer sequence.

In some instances, the antibody-binding moiety is protein A or functional derivatives thereof. In some instances, the antibody-binding moiety is protein G or functional derivatives thereof. In some instances, the transposase is a Tn5 transposase enzyme, a Mu transposase enzyme, a Tn7 transposase enzyme, a *vibhar* species transposase, or functional derivatives thereof.

In some instances, any of the methods described herein further comprise extending a 3' end of the capture probe using the fragmented genomic DNA as a template. In some instances, the extending step is performed using a DNA polymerase having strand displacement activity. In some instances, the determining step (g) comprises sequencing (i) all or part of the sequence of the spatial barcode or a complement thereof, and (ii) all or part of the sequence of the fragmented genomic DNA or a complement thereof.

In some instance, any of the methods herein further comprise staining the biological sample, optionally with hematoxylin and eosin (H&E) staining or immunofluorescence staining.

In some instances, adding the antibody or the multi-complex to the biological sample is performed under a chemical permeabilization condition, under an enzymatic permeabilization condition, or both. In some instances, the chemical permeabilization condition comprises a detergent. In some instances, the detergent is one or more of NP-40, polysorbate-20, and digitonin. In some instances, adding the antibody or the multi-complex to the biological sample is performed after an enzymatic pre-permeabilization condition. In some instances, the enzymatic pre-permeabilization condition comprises a protease. In some instances, the protease is a pepsin, a collagenase, a proteinase K, and combinations thereof.

In some instances, the biological sample is a fresh tissue sample, a frozen tissue sample, or a fixed tissue sample. In some instances, the biological sample is a formalin-fixed, paraffin embedded (FFPE) tissue sample. In some instances, the biological sample is a tissue section.

In some instances, the array comprises one or more features. In some instances, the capture probe further comprises a cleavage domain, one or more functional domains, a unique molecular identifier, or combinations thereof.

In some instances, any of the methods herein further comprise determining abundance and location of an analyte in the biological sample, the method comprising: hybridizing the analyte or a portion thereof to the capture domain; and determining (i) all or part of a sequence of the spatial barcode or a complement thereof, and (ii) all or part of a sequence of the analyte, or a complement thereof, and using the determined sequences of (i) and (ii) to determine the abundance and the location of the analyte in the biological sample.

In some instances, the analyte is RNA. In some instances, the RNA is mRNA.

In some instances, hybridizing the analyte or a portion thereof to the capture domain is performed at the same time as step (e).

In some instances, determining (i) all or part of a sequence of the spatial barcode or a complement thereof, and (ii) all or part of a sequence of the analyte, or a complement thereof occurs at the same time as step (g). In some instances, determining (i) all or part of a sequence of the spatial barcode or a complement thereof, and (ii) all or part of a sequence of the analyte, or a complement thereof comprises sequencing (i) all or part of the sequence of the spatial barcode or a complement thereof, and (ii) all or part of the sequence of the fragmented genomic DNA or a complement thereof.

Also provided herein are kits for determining a location of accessible genomic DNA in a biological sample comprising: (a) an array comprising a plurality of capture probes, wherein a capture probe of the plurality of capture probes comprises: (i) a spatial barcode and (ii) a capture domain; (b) a complex comprising: (i) an antibody-binding moiety, (ii) a transposase, (iii) a first transposon end sequence comprising a splint sequence that is substantially complementary to a portion of a splint oligonucleotide, and (iv) a second transposon end sequence comprising a functional sequence; and (c) instructions for performing any one of the methods described herein.

Also provided herein are kits for determining abundance and/or location of accessible genomic DNA in a biological sample comprising: (a) an array comprising a plurality of capture probes, wherein a capture probe of the plurality of capture probes comprises: (i) a spatial barcode and (ii) a capture domain; (b) a multi-complex comprising: (i) an antibody-binding moiety, (ii) a transposase, (iii) a first transposon end sequence comprising a splint sequence that is substantially complementary to a portion of a splint oligonucleotide, (iv) a second transposon end sequence comprising a functional sequence, and (v) an antibody that binds to a chromatin protein; and (c) instructions for performing any one of the methods described herein.

Also provided herein are compositions for determining abundance and/or location of accessible genomic DNA in a biological sample comprising: (a) an array comprising a plurality of capture probes, wherein a capture probe of the plurality of capture probes comprises: (i) a spatial barcode and (ii) a capture domain; and (b) a complex comprising: (i) an antibody-binding moiety, (ii) a transposase, (iii) a first transposon end sequence comprising a splint sequence that is substantially complementary to a portion of a splint oligonucleotide, and (iv) a second transposon end sequence.

Also provided herein are compositions for determining abundance and/or location of accessible genomic DNA in a biological sample comprising: (a) an array comprising a plurality of capture probes, wherein a capture probe of the plurality of capture probes comprises: (i) a spatial barcode and (ii) a capture domain; and (b) a multi-complex comprising: (i) an antibody-binding moiety, (ii) a transposase, (iii) a first transposon end sequence comprising a splint sequence that is substantially complementary to a portion of a splint oligonucleotide, (iv) a second transposon end sequence, and (v) an antibody that binds to a chromatin protein.

All publications, patents, and patent applications mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various instances of the features of this disclosure are described herein. However, it should be understood that such instances are provided merely by way of example, and numerous variations, changes, and substitutions can occur to those skilled in the art without departing from the scope of this disclosure. It should also be understood that various alternatives to the specific instances described herein are also within the scope of this disclosure.

BRIEF DESCRIPTION OF DRAWINGS

The following drawings illustrate certain instances of the features and advantages of this disclosure. These instances are not intended to limit the scope of the appended claims in any manner. Like reference symbols in the drawings indicate like elements.

DETAILED DESCRIPTION

Figure 1A:
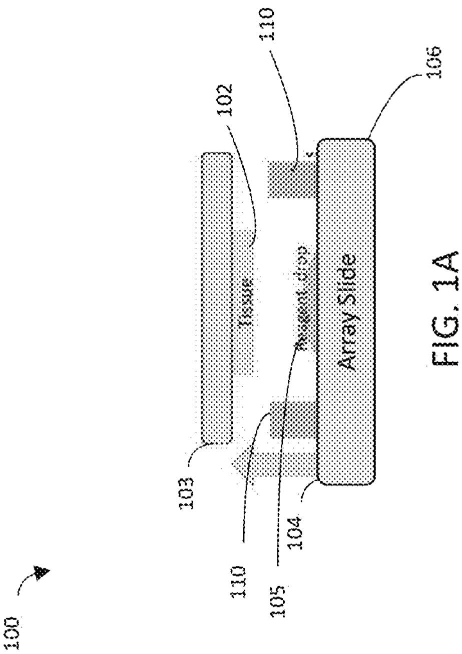
FIG. 1A shows an exemplary sandwiching process where a first substrate (e.g., a slide), including a biological sample, and a second substrate (e.g., array slide) are brought into proximity with one another.

Epigenomic methods such as CUT & Run or CUT & Tag methodologies help identify regulators (e.g., cis regulators and/or trans regulators) that contribute to dynamic cellular phenotypes. While CUT & Run and CUT & Tag methodologies have been valuable in defining epigenetic variability within a cell population, conventional applications of these methods are limited in their ability to spatially resolve the two- and three-dimensional structures and associated genes that promote cellular variation. Methods that can simultaneously assess epigenomes and localize gene expression in a tissue sample would be useful.

Thus, the present disclosure relates generally to the spatial tagging and analysis of nucleic acids. In some instances, provided herein are methods that utilize a transposome to fragment genomic DNA and to capture the fragmented DNA on a spatial array, thus revealing epigenomic insights regarding the structural features contributing to cellular regulation within the spatial context of a biological sample.

Spatial Analysis Methods

Spatial analysis methodologies described herein can provide a vast amount of analyte and/or expression data for a variety of analytes within a biological sample at high spatial resolution, while retaining native spatial context. Spatial analysis methods can include, e.g., the use of a capture probe including a spatial barcode (e.g., a nucleic acid sequence that provides information as to the location or position of an analyte within a cell or a tissue sample (e.g., mammalian cell or a mammalian tissue sample) and a capture domain that is capable of binding to an analyte (e.g., a protein and/or a nucleic acid) produced by and/or present in a cell. Spatial analysis methods and compositions can also include the use of a capture probe having a capture domain that captures an intermediate agent for indirect detection of an analyte. For example, the intermediate agent can include a nucleic acid sequence (e.g., a barcode) associated with the intermediate agent. Detection of the intermediate agent is therefore indicative of the analyte in the cell or tissue sample.

Non-limiting aspects of spatial analysis methodologies and compositions are described in U.S. Pat. Nos. 11,447,807, 11,352,667, 11,168,350, 11,104,936, 11,008,608, 10,995,361, 10,913,975, 10,774,374, 10,724,078, 10,640,816, 10,494,662, 10,480,022, 10,364,457, 10,317,321, 10,059,990, 10,041,949, 10,030,261, 10,002,316, 9,879,313, 9,783,841, 9,727,810, 9,593,365, 8,951,726, 8,604,182, and 7,709,198; U.S. Patent Application Publication Nos. 2020/0239946, 2020/0080136, 2020/0277663, 2019/0330617, 2020/0256867, 2020/0224244, 2019/0085383, and 2013/0171621; PCT Publication Nos. WO2018/091676, WO2020/176788, WO2017/144338, and WO2016/057552; Non-patent literature references Rodrigues et al., Science 363(6434):1463-1467, 2019; Lee et al., Nat. Protoc. 10(3): 442-458, 2015; Trejo et al., PLoS ONE 14(2):e0212031, 2019; Chen et al., Science 348(6233):aaa6090, 2015; Gao et al., BMC Biol. 15:50, 2017; and Gupta et al., Nature Biotechnol. 36:1197-1202, 2018; the Visium Spatial Gene Expression Reagent Kits User Guide (e.g., Rev F, dated January 2022); and/or the Visium Spatial Gene Expression Reagent Kits—Tissue Optimization User Guide (e.g., Rev E, dated February 2022), both of which are available at the 10× Genomics Support Documentation website, and can be used herein in any combination, and each of which is incorporated herein by reference in their entireties. Further non-limiting aspects of spatial analysis methodologies and compositions are described herein.

Some general terminology that may be used in this disclosure can be found in Section (I)(b) of PCT Publication No. WO2020/176788 and/or U.S. Patent Application Publication No. 2020/0277663. Typically, a “barcode” is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes. For the purpose of this disclosure, an “analyte” can include any biological substance, structure, moiety, or component to be analyzed. The term “target” can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral proteins (e.g., viral capsid, viral envelope, viral coat, viral accessory, viral glycoproteins, viral spike, etc.), extracellular and intracellular proteins, antibodies, and antigen binding fragments. In some embodiments, the analyte(s) can be localized to subcellular location(s), including, for example, organelles, e.g., mitochondria, Golgi apparatus, endoplasmic reticulum, chloroplasts, endocytic vesicles, exocytic vesicles, vacuoles, lysosomes, etc. In some embodiments, analyte(s) can be peptides or proteins, including without limitation antibodies and enzymes. Additional examples of analytes can be found in Section (I)(c) of PCT Publication No. WO2020/176788 and/or U.S. Patent Application Publication No. 2020/0277663. In some embodiments, an analyte can be detected indirectly, such as through detection of an intermediate agent, for example, a ligation product or an analyte capture agent (e.g., an oligonucleotide-conjugated antibody), such as those described herein.

A "biological sample" is typically obtained from the subject for analysis using any of a variety of techniques including, but not limited to, biopsy, surgery, and laser capture microscopy (LCM), and generally includes cells and/or other biological material from the subject. In some instances, the biological sample is an organism (e.g., a small organism such as a parasite). In some embodiments, a biological sample can be a fixed and/or stained biological sample (e.g., a fixed and/or stained tissue or sample). Additional methods of fixation and preparation are provided in this application.

In some instances, the biological sample is fixed using PAXgene. PAXgene is a formalin-free, non-cross-linking fixative that preserves morphology and biomolecules. It is a mixture of different alcohols, acid, and a soluble organic compound. Ergin B. et al., J Proteome Res. 2010 Oct. 1; 9(10):5188-96 appears to have first developed and described PAXgene. Kap M. et al., PLoS One.; 6(11):e27704 (2011) and Mathieson W. et al., Am J Clin Pathol.; 146(1):25-40 (2016) both describe and evaluate PAXgene for tissue fixation. Non-limiting examples of stains include histological stains (e.g., hematoxylin and/or eosin) and immunological stains (e.g., fluorescent stains). In some embodiments, a biological sample (e.g., a fixed and/or stained biological sample) can be imaged. Biological samples are also described in Section (I)(d) of PCT Publication No. WO2020/176788 and/or U.S. Patent Application Publication No. 2020/0277663.

The following embodiments can be used with any of the methods described herein. In some embodiments, the biological sample is imaged. In some embodiments, the biological sample is visualized or imaged using bright field microscopy. In some embodiments, the biological sample is visualized or imaged using fluorescence microscopy. Additional methods of visualization and imaging are known in the art. Non-limiting examples of visualization and imaging include expansion microscopy, bright field microscopy, dark field microscopy, phase contrast microscopy, electron microscopy, fluorescence microscopy, reflection microscopy, interference microscopy and confocal microscopy. In some embodiments, the sample is stained and imaged prior to adding the primer to the biological sample.

In some embodiments, the method includes staining the biological sample. In some embodiments, the staining includes the use of hematoxylin and eosin. In some embodiments, a biological sample can be stained using any number of biological stains, including but not limited to, acridine orange, Bismarck brown, carmine, coomassie blue, cresyl violet, DAPI, eosin, ethidium bromide, acid fuchsine, hematoxylin, Hoechst stains, iodine, methyl green, methylene blue, neutral red, Nile blue, Nile red, osmium tetroxide, propidium iodide, rhodamine, or safranin. In some instances, the biological sample can be stained using known staining techniques, including Can-Grunwald, Giemsa, hematoxylin and eosin (H&E), Jenner's, Leishman, Masson's trichrome, Papanicolaou, Romanowsky, silver, Sudan, Wright's, and/or Periodic Acid Schiff (PAS) staining techniques. PAS staining is typically performed after formalin or acetone fixation.

In some embodiments, the staining includes the use of a detectable label selected from the group consisting of a radioisotope, a fluorophore, a chemiluminescent compound, a bioluminescent compound, or a combination thereof.

In some embodiments, a biological sample is permeabilized with one or more permeabilization reagents. For example, permeabilization of a biological sample can facilitate analyte capture. Exemplary permeabilization agents and conditions are described in Section (I)(d)(ii)(13) or the Exemplary Embodiments Section of PCT Publication No. WO2020/176788 and/or U.S. Patent Application Publication No. 2020/0277663. Briefly, in any of the methods described herein, the method includes a step of permeabilizing the biological sample. For example, the biological sample can be permeabilized to facilitate transfer of the extension products to the capture probes on the array. In some embodiments, the permeabilizing includes the use of an organic solvent (e.g., acetone, ethanol, and methanol), a detergent (e.g., saponin, Triton X-100™, Tween-20™, or sodium dodecyl sulfate (SDS)), an enzyme (an endopeptidase, an exopeptidase, a protease), or combinations thereof. In some embodiments, the permeabilizing includes the use of an endopeptidase, a protease, SDS, polyethylene glycol tert-octylphenyl ether, polysorbate 80, and polysorbate 20, N-lauroylsarcosine sodium salt solution, saponin, Triton X-100™, Tween-20™, or combinations thereof. In some embodiments, the endopeptidase is pepsin. In some embodiments, the endopeptidase is Proteinase K. Additional methods for sample permeabilization are described, for example, in Jamur et al., *Method Mol. Biol.* 588:63-66, 2010, the entire contents of which are incorporated herein by reference.

Array-based spatial analysis methods involve the transfer of one or more analytes from a biological sample to an array of features on a substrate, where each feature is associated with a unique spatial location on the array. Subsequent analysis of the transferred analytes includes determining the identity of the analytes and the spatial location of the analytes within the biological sample. The spatial location of an analyte within the biological sample is determined based on the feature to which the analyte is bound (e.g., directly or indirectly) on the array, and the feature's relative spatial location within the array.

A "capture probe" refers to any molecule capable of capturing (directly or indirectly) and/or labelling an analyte (e.g., an analyte of interest) in a biological sample. In some embodiments, the capture probe is a nucleic acid or a polypeptide. In some embodiments, the capture probe includes a barcode (e.g., a spatial barcode and/or a unique molecular identifier (UMI)) and a capture domain). In some instances, the capture probe includes a homopolymer sequence, such as a poly(T) sequence. In some embodiments, a capture probe can include a cleavage domain and/or a functional domain (e.g., a primer-binding site, such as for next-generation sequencing (NGS)). See, e.g., Section (II)(b) (e.g., subsections (i)-(vi)) of PCT Publication No. WO2020/176788 and/or U.S. Patent Application Publication No. 2020/0277663. Generation of capture probes can be achieved by any appropriate method, including those described in Section (II)(d)(ii) of PCT Publication No. WO2020/176788 and/or U.S. Patent Application Publication No. 2020/0277663.

In some embodiments, the biological sample is mounted on a first substrate and the substrate comprising the array of capture probes is a second substrate. During this process, one or more analytes or analyte derivatives (e.g., intermediate agents; e.g., ligation products) are released from the biological sample and migrate to the second substrate comprising an array of capture probes. In some embodiments, the release and migration of the analytes or analyte derivatives to the second substrate comprising the array of capture probes occurs in a manner that preserves the original spatial context of the analytes in the biological sample. This method can be referred to as a sandwiching process, which is described e.g., in U.S. Patent Application Pub. No. 2021/0189475 and PCT Pub. Nos. WO 2021/252747 A1, WO 2022/061152 A2, and WO 2022/140028 A1.

FIG. 1A shows an exemplary sandwiching process 100 where a first substrate (e.g., slide 103), including a biological sample 102 (e.g., a parasitic organism), and a second substrate (e.g., array slide 104 including an array having spatially barcoded capture probes 106) are brought into proximity with one another. As shown in FIG. 1A a liquid reagent drop (e.g., permeabilization solution 105) is introduced on the second substrate in proximity to the capture probes 106 and in between the biological sample 102 and the second substrate (e.g., slide 104 including an array having spatially barcoded capture probes 106). The permeabilization solution 105 may release analytes or analyte derivatives (e.g., intermediate agents; e.g., ligation products) that can be captured by the capture probes of the array 106.

During the exemplary sandwiching process, the first substrate is aligned with the second substrate, such that at least a portion of the biological sample is aligned with at least a portion of the capture probes (e.g., aligned in a sandwich configuration). As shown, the second substrate (e.g., array slide 104) is in a superior position to the first substrate (e.g., slide 103). In some embodiments, the first substrate (e.g., slide 103) may be positioned superior to the second substrate (e.g., slide 104). A reagent medium 105 within a gap between the first substrate (e.g., slide 103) and the second substrate (e.g., slide 104) creates a liquid interface between the two substrates. The reagent medium may be a permeabilization solution which permeabilizes and/or digests the biological sample 102. In some embodiments wherein the biological sample 102 has been pre-permeabilized, the reagent medium is not a permeabilization solution. In some embodiments, analytes (e.g., mRNA transcripts) and/or analyte derivatives (e.g., intermediate agents; e.g., ligation products) of the biological sample 102 may release from the biological sample, actively or passively migrate (e.g., diffuse) across the gap toward the capture probes on the array 106. Alternatively, in certain embodiments, migration of the analyte or analyte derivative (e.g., intermediate agent; e.g., ligation product) from the biological sample is performed actively (e.g., electrophoretic, by applying an electric field to promote migration). Exemplary methods of electrophoretic migration are described in WO 2020/176788, and US. Patent Application Pub. No. 2021/0189475, each of which is hereby incorporated by reference.

As further shown, one or more spacers 110 may be positioned between the first substrate (e.g., slide 103) and the second substrate (e.g., array slide 104 including spatially barcoded capture probes 106). The one or more spacers 110 may be configured to maintain a separation distance between the first substrate and the second substrate. While the one or more spacers 110 is shown as disposed on the second substrate, the spacer may additionally or alternatively be disposed on the first substrate.

In some embodiments, the one or more spacers 110 is configured to maintain a separation distance between first and second substrates that is between about 2 microns and 1 mm (e.g., between about 2 microns and 800 microns, between about 2 microns and 700 microns, between about 2 microns and 600 microns, between about 2 microns and 500 microns, between about 2 microns and 400 microns, between about 2 microns and 300 microns, between about 2 microns and 200 microns, between about 2 microns and 100 microns, between about 2 microns and 25 microns, or between about 2 microns and 10 microns), measured in a direction orthogonal to the surface of first substrate that supports the biological sample. In some instances, the separation distance is about 2, 3, 4, 5, 6, 7, 8, 9, 10, 11, 12, 13, 14, 15, 16, 17, 18, 19, 20, 21, 22, 23, 24, or 25 microns. In some embodiments, the separation distance is less than 50 microns. In some embodiments, the separation distance is less than 25 microns. In some embodiments, the separation distance is less than 20 microns. The separation distance may include a distance of at least 2 μm.

Figure 1B:
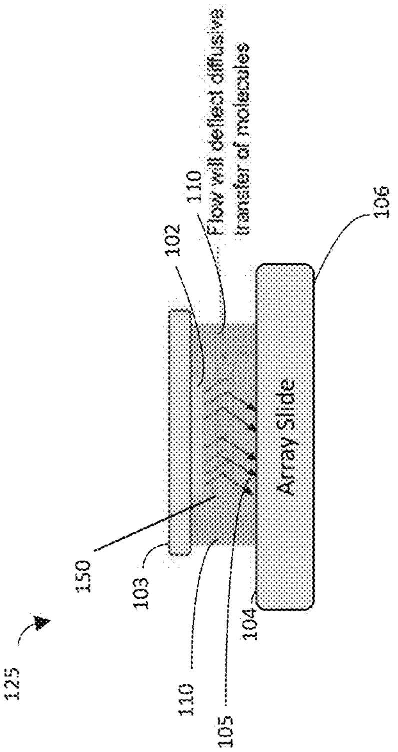
FIG. 1B shows a fully formed sandwich configuration creating a chamber formed from one or more spacers, the first substrate, and the second substrate.

FIG. 1B shows a fully formed sandwich configuration 125 creating a chamber 150 formed from the one or more spacers 110, the first substrate (e.g., the slide 103), and the second substrate (e.g., the slide 104 including an array 106 having spatially barcoded capture probes) in accordance with some example implementations. In the example of FIG. 1B, the liquid reagent (e.g., the permeabilization solution 105) fills the volume of the chamber 150 and may create a permeabilization buffer that allows analytes (e.g., mRNA transcripts and/or other molecules) or analyte derivatives (e.g., intermediate agents; e.g., ligation products) to diffuse from the biological sample 102 toward the capture probes of the second substrate (e.g., slide 104). In some aspects, flow of the permeabilization buffer may deflect transcripts and/or molecules from the biological sample 102 and may affect diffusive transfer of analytes or analyte derivatives (e.g., intermediate agents; e.g., ligation products) for spatial analysis. A partially or fully sealed chamber 150 resulting from the one or more spacers 110, the first substrate, and the second substrate may reduce or prevent flow from undesirable convective movement of transcripts and/or molecules over the diffusive transfer from the biological sample 102 to the capture probes.

The sandwiching process methods described above can be implemented using a variety of hardware components. For example, the sandwiching process methods can be implemented using a sample holder (also referred to herein as a support device, a sample handling apparatus, and an array alignment device). Further details on support devices, sample holders, sample handling apparatuses, or systems for implementing a sandwiching process are described in, e.g., US. Patent Application Pub. No. 2021/0189475, and PCT Publ. No. WO 2022/061152 A2, each of which are incorporated by reference in their entirety.

In some embodiments of a sample holder, the sample holder can include a first member including a first retaining mechanism configured to retain a first substrate comprising a biological sample. The first retaining mechanism can be configured to retain the first substrate disposed in a first plane. The sample holder can further include a second member including a second retaining mechanism configured to retain a second substrate disposed in a second plane. The sample holder can further include an alignment mechanism connected to one or both of the first member and the second member. The alignment mechanism can be configured to align the first and second members along the first plane and/or the second plane such that the sample contacts at least a portion of the reagent medium when the first and second members are aligned and within a threshold distance along an axis orthogonal to the second plane. The adjustment mechanism may be configured to move the second member along the axis orthogonal to the second plane and/or move the first member along an axis orthogonal to the first plane.

In some embodiments, the adjustment mechanism includes a linear actuator. In some embodiments, the linear actuator is configured to move the second member along an axis orthogonal to the plane of the first member and/or the second member. In some embodiments, the linear actuator is configured to move the first member along an axis orthogonal to the plane of the first member and/or the second member. In some embodiments, the linear actuator is configured to move the first member, the second member, or both the first member and the second member at a velocity of at least 0.1 mm/sec. In some embodiments, the linear actuator is configured to move the first member, the second member, or both the first member and the second member with an amount of force of at least 0.1 lbs.

Figure 2A:
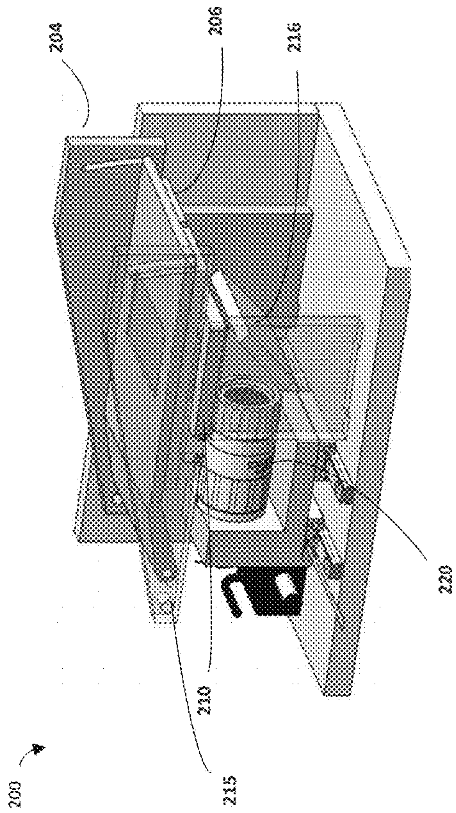
FIG. 2A shows a perspective view of an exemplary sample handling apparatus in a closed position.

FIG. 2A is a perspective view of an example sample handling apparatus 200 in a closed position in accordance with some example implementations. As shown, the sample handling apparatus 200 includes a first member 204, a second member 210, optionally an image capture device 220, a first substrate 206, optionally a hinge 215, and optionally a mirror 216. The hinge 215 may be configured to allow the first member 204 to be positioned in an open or closed configuration by opening and/or closing the first member 204 in a clamshell manner along the hinge 215.

Figure 2B:
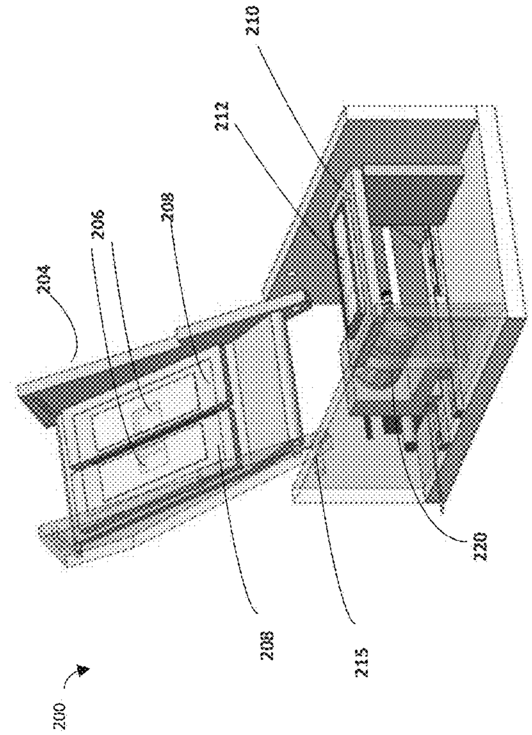
FIG. 2B shows a perspective view of an exemplary sample handling apparatus in an open position.

FIG. 2B is a perspective view of the example sample handling apparatus 200 in an open position in accordance with some example implementations. As shown, the sample handling apparatus 200 includes one or more first retaining mechanisms 208 configured to retain one or more first substrates 206. In the example of FIG. 2B, the first member 204 is configured to retain two first substrates 206, however the first member 204 may be configured to retain more or fewer first substrates 206.

In some aspects, when the sample handling apparatus 200 is in an open position (e.g., in FIG. 2B), the first substrate 206 and/or the second substrate 212 may be loaded and positioned within the sample handling apparatus 200 such as within the first member 204 and the second member 210, respectively. As noted, the hinge 215 may allow the first member 204 to close over the second member 210 and form a sandwich configuration.

In some aspects, after the first member 204 closes over the second member 210, an adjustment mechanism of the sample handling apparatus 200 may actuate the first member 204 and/or the second member 210 to form the sandwich configuration for the permeabilization step (e.g., bringing the first substrate 206 and the second substrate 212 closer to each other and within a threshold distance for the sandwich configuration). The adjustment mechanism may be configured to control a speed, an angle, a force, or the like of the sandwich configuration.

In some embodiments, the biological sample (e.g., sample 102 from FIG. 1A) may be aligned within the first member 204 (e.g., via the first retaining mechanism 208) prior to closing the first member 204 such that a desired region of interest of the sample is aligned with the barcoded array of the second substrate (e.g., the slide 104 from FIG. 1A), e.g., when the first and second substrates are aligned in the sandwich configuration. Such alignment may be accomplished manually (e.g., by a user) or automatically (e.g., via an automated alignment mechanism). After or before alignment, spacers may be applied to the first substrate 206 and/or the second substrate 212 to maintain a minimum spacing between the first substrate 206 and the second substrate 212 during sandwiching. In some aspects, the permeabilization solution (e.g., permeabilization solution 305) may be applied to the first substrate 206 and/or the second substrate 212. The first member 204 may then close over the second member 210 and form the sandwich configuration. Analytes or analyte derivatives (e.g., intermediate agents; e.g., ligation products) may be captured by the capture probes of the array and may be processed for spatial analysis.

In some embodiments, during the permeabilization step, the image capture device 220 may capture images of the overlap area between the biological sample and the capture probes on the array 106. If more than one first substrates 206 and/or second substrates 212 are present within the sample handling apparatus 200, the image capture device 220 may be configured to capture one or more images of one or more overlap areas.

Figures 3A, 3B, 3C:
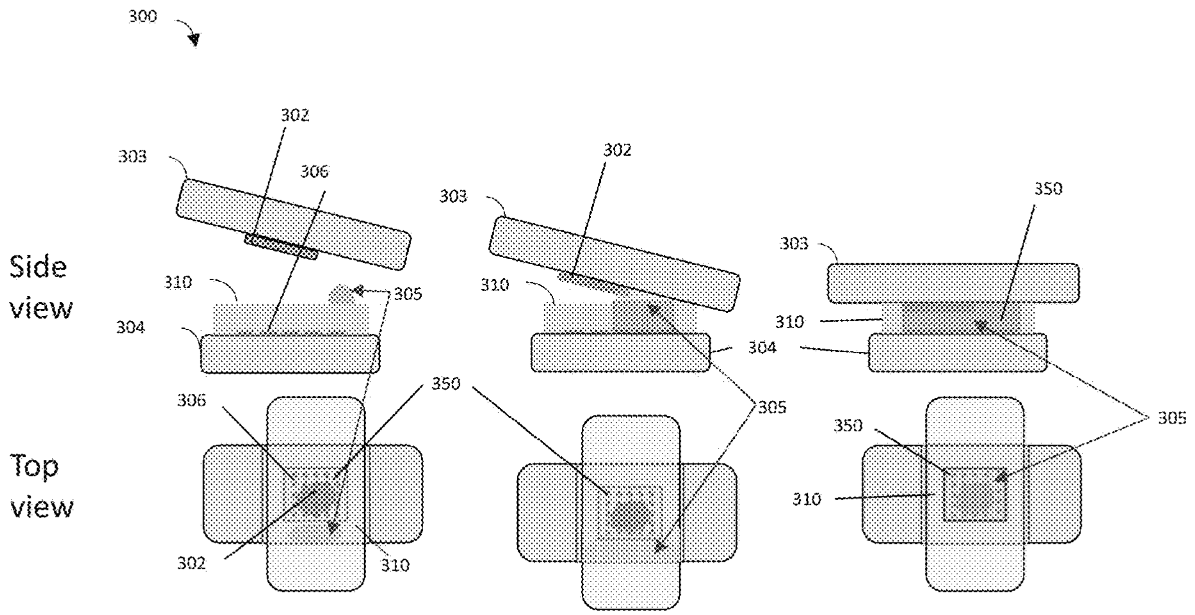
FIG. 3A shows the first substrate angled over (superior to) the second substrate.
FIG. 3B shows that as the first substrate lowers, and/or as the second substrate rises, the dropped side of the first substrate may contact a drop of reagent medium.
FIG. 3C shows a full closure and sandwiching of the first substrate and the second substrate with one or more spacers contacting both the first substrate and the second substrate.

Provided herein are methods for delivering a fluid to a biological sample disposed on an area of a first substrate and an array disposed on a second substrate. FIGS. 3A-3C depict a side view and a top view of an exemplary angled closure workflow 300 for sandwiching a first substrate (e.g., slide 303) having a biological sample 302 and a second substrate (e.g., slide 304 having capture probes 306) in accordance with some exemplary implementations.

FIG. 3A depicts the first substrate (e.g., the slide 303 including a biological sample 302) angled over (superior to) the second substrate (e.g., slide 304). As shown, reagent medium (e.g., permeabilization solution) 305 is located on the spacer 310 toward the right-hand side of the side view in FIG. 3A. While FIG. 3A depicts the reagent medium on the right hand side of side view, it should be understood that such depiction is not meant to be limiting as to the location of the reagent medium on the spacer.

FIG. 3B shows that as the first substrate lowers, and/or as the second substrate rises, the dropped side of the first substrate (e.g., a side of the slide 303 angled toward the second substrate) may contact the reagent medium 305. The dropped side of the first substrate may urge the reagent medium 305 toward the opposite direction (e.g., towards an opposite side of the spacer 310, towards an opposite side of the first substrate relative to the dropped side). For example, in the side view of FIG. 3B the reagent medium 305 may be urged from right to left as the sandwich is formed.

In some embodiments, the first substrate and/or the second substrate are further moved to achieve an approximately parallel arrangement of the first substrate and the second substrate.

FIG. 3C depicts a full closure of the sandwich between the first substrate and the second substrate with the spacer 310 contacting both the first substrate and the second substrate and maintaining a separation distance and optionally the approximately parallel arrangement between the two substrates. As shown in the top view of FIG. 3C, the spacer 310 fully encloses and surrounds the biological sample 302 and the capture probes 306, and the spacer 310 form the sides of chamber 350 which holds a volume of the reagent medium 305.

While FIG. 3C depicts the first substrate (e.g., the slide 303 including biological sample 302) angled over (superior to) the second substrate (e.g., slide 304) and the second substrate comprising the spacer 310, it should be understood that an exemplary angled closure workflow can include the second substrate angled over (superior to) the first substrate and the first substrate comprising the spacer 310.

It may be desirable that the reagent medium be free from air bubbles between the substrates to facilitate transfer of target analytes with spatial information. Additionally, air bubbles present between the substrates may obscure at least a portion of an image capture of a desired region of interest. Accordingly, it may be desirable to ensure or encourage suppression and/or elimination of air bubbles between the two substrates (e.g., slide 303 and slide 304) during a permeabilization step (e.g., step 104). In some aspects, it may be possible to reduce or eliminate bubble formation between the substrates using a variety of filling methods and/or closing methods. In some instances, the first substrate and the second substrate are arranged in an angled sandwich assembly as described herein. For example, during the sandwiching of the two substrates (e.g., the slide 303 and the slide 304), an angled closure workflow may be used to suppress or eliminate bubble formation.

Figures 4A, 4B:
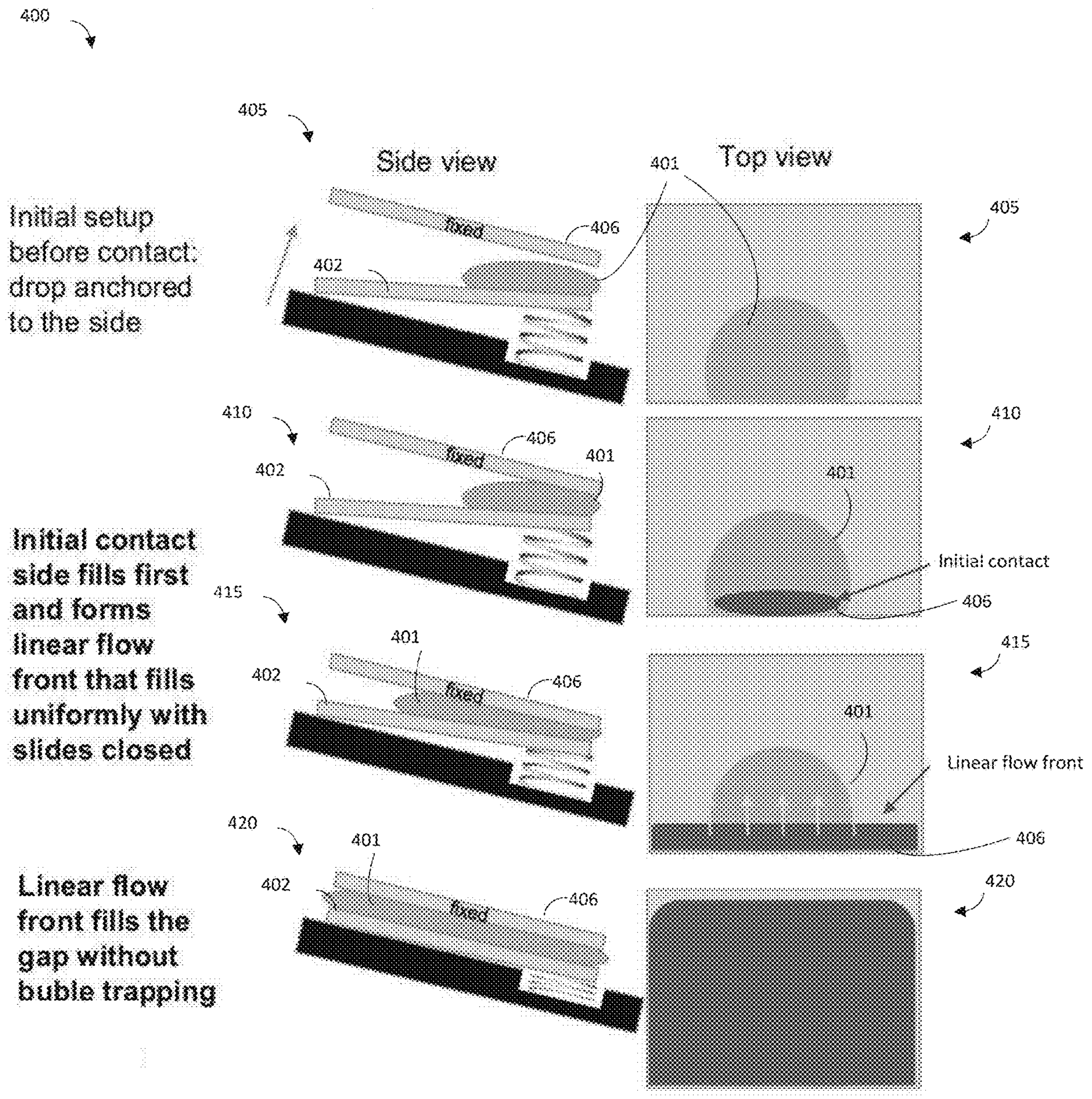
FIG. 4A shows a side view of the angled closure workflow.
FIG. 4B shows a top view of the angled closure workflow.

FIG. 4A is a side view of the angled closure workflow 400 in accordance with some exemplary implementations. FIG. 4B is a top view of the angled closure workflow 400 in accordance with some exemplary implementations. As shown at 405, reagent medium 401 is positioned to the side of the substrate 402 contacting the spring.

At step 410, the dropped side of the angled substrate 406 contacts the reagent medium 401 first. The contact of the substrate 406 with the reagent medium 401 may form a linear or low curvature flow front that fills uniformly with the slides closed.

At step 415, the substrate 406 is further lowered toward the substrate 402 (or the substrate 402 is raised up toward the substrate 406) and the dropped side of the substrate 406 may contact and may urge the liquid reagent toward the side opposite the dropped side and creating a linear or low curvature flow front that may prevent or reduce bubble trapping between the substrates. As further shown, the spring may begin to compress as the substrate 406 is lowered.

At step 420, the reagent medium 401 fills the gap between the substrate 406 and the substrate 402. The linear flow front of the liquid reagent may form by squeezing the 401 volume along the contact side of the substrate 402 and/or the substrate 406. Additionally, capillary flow may also contribute to filling the gap area. As further shown in step 420, the spring may be fully compressed such that the substrate 406, the substrate 402, and the base are substantially parallel to each other.

In some embodiments, the reagent medium (e.g., 105 in FIG. 1A) comprises a permeabilization agent. In some embodiments, following initial contact between the biological sample and a permeabilization agent, the permeabilization agent can be removed from contact with the biological sample (e.g., by opening sample holder). Suitable agents for this purpose include, but are not limited to, organic solvents (e.g., acetone, ethanol, and methanol), cross-linking agents (e.g., paraformaldehyde), detergents (e.g., saponin, Triton X100™, Tween-20™, or sodium dodecyl sulfate (SDS)), and enzymes (e.g., trypsin, proteases (e.g., proteinase K). In some embodiments, the detergent is an anionic detergent (e.g., SDS or N-lauroylsarcosine sodium salt solution).

In some embodiments, the reagent medium comprises a lysis reagent. Lysis solutions can include ionic surfactants such as, for example, sarkosyl and sodium dodecyl sulfate (SDS). More generally, chemical lysis agents can include, without limitation, organic solvents, chelating agents, detergents, surfactants, and chaotropic agents. In some embodiments, the reagent medium comprises a protease. Exemplary proteases include, e.g., pepsin, trypsin, pepsin, elastase, and proteinase K. In some embodiments, the reagent medium comprises a nuclease. In some embodiments, the nuclease comprises an RNase. In some embodiments, the Rnase is selected from Rnase A, Rnase C, Rnase H, and Rnase I. In some embodiments, the reagent medium comprises one or more of sodium dodecyl sulfate (SDS), proteinase K, pepsin, N-lauroylsarcosine, RNAse, and a sodium salt thereof.

In some embodiments, the reagent medium comprises polyethylene glycol (PEG). In some embodiments, the PEG is from about PEG 2K to about PEG 16K. In some embodiments, the PEG is PEG 2K, 3K, 4K, 5K, 6K, 7K, 8K, 9K, 10K, 11K, 12K, 13K, 14K, 15K, or 16K. In some embodiments, the PEG is present at a concentration from about 2% to 25%, from about 4% to about 23%, from about 6% to about 21%, or from about 8% to about 20% (v/v).

In certain embodiments a dried permeabilization reagent is applied or formed as a layer on the first substrate or the second substrate or both prior to contacting the biological sample and the array. For example, a permeabilization reagent can be deposited in solution on the first substrate or the second substrate or both and then dried.

In some instances, the aligned portions of the biological sample and the array are in contact with the reagent medium for about 1 minute, about 5 minutes, about 10 minutes, about 12 minutes, about 15 minutes, about 18 minutes, about 20 minutes, about 25 minutes, about 30 minutes, about 36 minutes, about 45 minutes, or about an hour. In some instances, the aligned portions of the biological sample and the array are in contact with the reagent medium for about 1-60 minutes.

In some instances, the device is configured to control a temperature of the first and second substrates. In some embodiments, the temperature of the first and second members is lowered to a first temperature that is below room temperature.

There are at least two methods to associate a spatial barcode with one or more neighboring cells, such that the spatial barcode identifies the one or more cells, and/or contents of the one or more cells, as associated with a particular spatial location. One method is to promote analytes or analyte proxies (e.g., intermediate agents) out of a cell and towards a spatially-barcoded array (e.g., including spatially-barcoded capture probes). Another method is to cleave spatially-barcoded capture probes from an array and promote the spatially-barcoded capture probes towards and/or into or onto the biological sample.

In some cases, capture probes may be configured to prime, replicate, and consequently yield optionally barcoded extension products from a template (e.g., a DNA or RNA template, such as an analyte or an intermediate agent (e.g., a ligation product or an analyte capture agent), or a portion thereof), or derivatives thereof (see, e.g., Section (II)(b)(vii) of PCT Publication No. WO2020/176788 and/or U.S. Patent Application Publication No. 2020/0277663 regarding extended capture probes). In some cases, capture probes may be configured to form ligation products with a template (e.g., a DNA or RNA template, such as an analyte or an intermediate agent, or portion thereof), thereby creating ligations products that serve as proxies for the template.

As used herein, an "extended capture probe" refers to a capture probe having additional nucleotides added to the terminus (e.g., 3' or 5' end) of the capture probe thereby extending the overall length of the capture probe. For example, an "extended 3' end" indicates additional nucleotides were added to the most 3' nucleotide of the capture probe to extend the length of the capture probe, for example, by polymerization reactions used to extend nucleic acid molecules including templated polymerization catalyzed by a polymerase (e.g., a DNA polymerase or a reverse transcriptase). In some embodiments, extending the capture probe includes adding to a 3' end of a capture probe a nucleic acid sequence that is complementary to a nucleic acid sequence of an analyte or intermediate agent specifically bound to the capture domain of the capture probe. In some embodiments, the capture probe is extended by a reverse transcriptase. In some embodiments, the capture probe is extended using one or more DNA polymerases. In some embodiments, the extended capture probes include the sequence of the capture domain and the sequence of the spatial barcode of the capture probe.

In some embodiments, extended capture probes are amplified (e.g., in bulk solution or on the array) to yield quantities that are sufficient for downstream analysis, e.g., sequencing. In some embodiments, extended capture probes (e.g., DNA molecules) can act as templates for an amplification reaction (e.g., a polymerase chain reaction).

Additional variants of spatial analysis methods, including in some embodiments, an imaging step, are described in Section (II)(a) of PCT Publication No. WO2020/176788 and/or U.S. Patent Application Publication No. 2020/0277663. Analysis of captured analytes (and/or intermediate agents or portions thereof), for example, including sample removal, extension of capture probes, sequencing (e.g., of a cleaved extended capture probe and/or a cDNA molecule complementary to an extended capture probe), sequencing on the array (e.g., using, for example, in situ hybridization or in situ ligation approaches), temporal analysis, and/or proximity capture, is described in Section (II)(g) of PCT Publication No. WO2020/176788 and/or U.S. Patent Application Publication No. 2020/0277663. Some quality control measures are described in Section (II)(h) of PCT Publication No. WO2020/176788 and/or U.S. Patent Application Publication No. 2020/0277663.

Spatial information can provide information of medical importance. For example, the methods described herein can allow for: identification of one or more biomarkers (e.g., diagnostic, prognostic, and/or for determination of efficacy of a treatment) of a disease or disorder; identification of a candidate drug target for treatment of a disease or disorder; identification (e.g., diagnosis) of a subject as having a disease or disorder; identification of stage and/or prognosis of a disease or disorder in a subject; identification of a subject as having an increased likelihood of developing a disease or disorder; monitoring of progression of a disease or disorder in a subject; determination of efficacy of a treatment of a disease or disorder in a subject; identification of a patient subpopulation for which a treatment is effective for a disease or disorder; modification of a treatment of a subject with a disease or disorder; selection of a subject for participation in a clinical trial; and/or selection of a treatment for a subject with a disease or disorder. Exemplary methods for identifying spatial information of biological and/or medical importance can be found in U.S. Patent Application Publication Nos. 2021/0140982, 2021/0198741, and 2021/0199660.

Spatial information can provide information of biological importance. For example, the methods described herein can allow for: identification of transcriptome and/or proteome expression profiles (e.g., in healthy and/or diseased tissue); identification of multiple analyte types in close proximity (e.g., nearest neighbor or proximity based analysis); determination of up- and/or down-regulated genes and/or proteins in diseased tissue; characterization of tumor microenvironments; characterization of tumor immune responses; characterization of cells types and their co-localization in healthy and diseased tissue; and identification of genetic variants within tissues (e.g., based on gene and/or protein expression profiles associated with specific disease or disorder biomarkers).

Typically, for spatial array-based methods, a substrate functions as a support for direct or indirect attachment of capture probes to features of the array. A “feature” is an entity that acts as a support or repository for various molecular entities used in spatial analysis. In some embodiments, some or all of the features in an array are functionalized for analyte capture. Exemplary substrates are described in Section (II)(c) of PCT Publication No. WO2020/176788 and/or U.S. Patent Application Publication No. 2020/0277663. Exemplary features and geometric attributes of an array can be found in Sections (II)(d)(i), (II)(d)(iii), and (II)(d)(iv) of PCT Publication No. WO2020/176788 and/or U.S. Patent Application Publication No. 2020/0277663.

Generally, analytes and/or intermediate agents (or portions thereof) can be captured when contacting a biological sample with a substrate including capture probes (e.g., a substrate with capture probes embedded, spotted, printed, fabricated on the substrate, or a substrate with features (e.g., beads, wells) comprising capture probes). As used herein, “contact,” “contacted,” and/or “contacting,” a biological sample with a substrate refers to any contact (e.g., direct or indirect) such that capture probes can interact (e.g., bind covalently or non-covalently (e.g., hybridize)) with analytes from the biological sample. Capture can be achieved actively (e.g., using electrophoresis) or passively (e.g., using diffusion). Analyte capture is further described in Section (II)(e) of PCT Publication No. WO2020/176788 and/or U.S. Patent Application Publication No. 2020/0277663.

Figure 5:
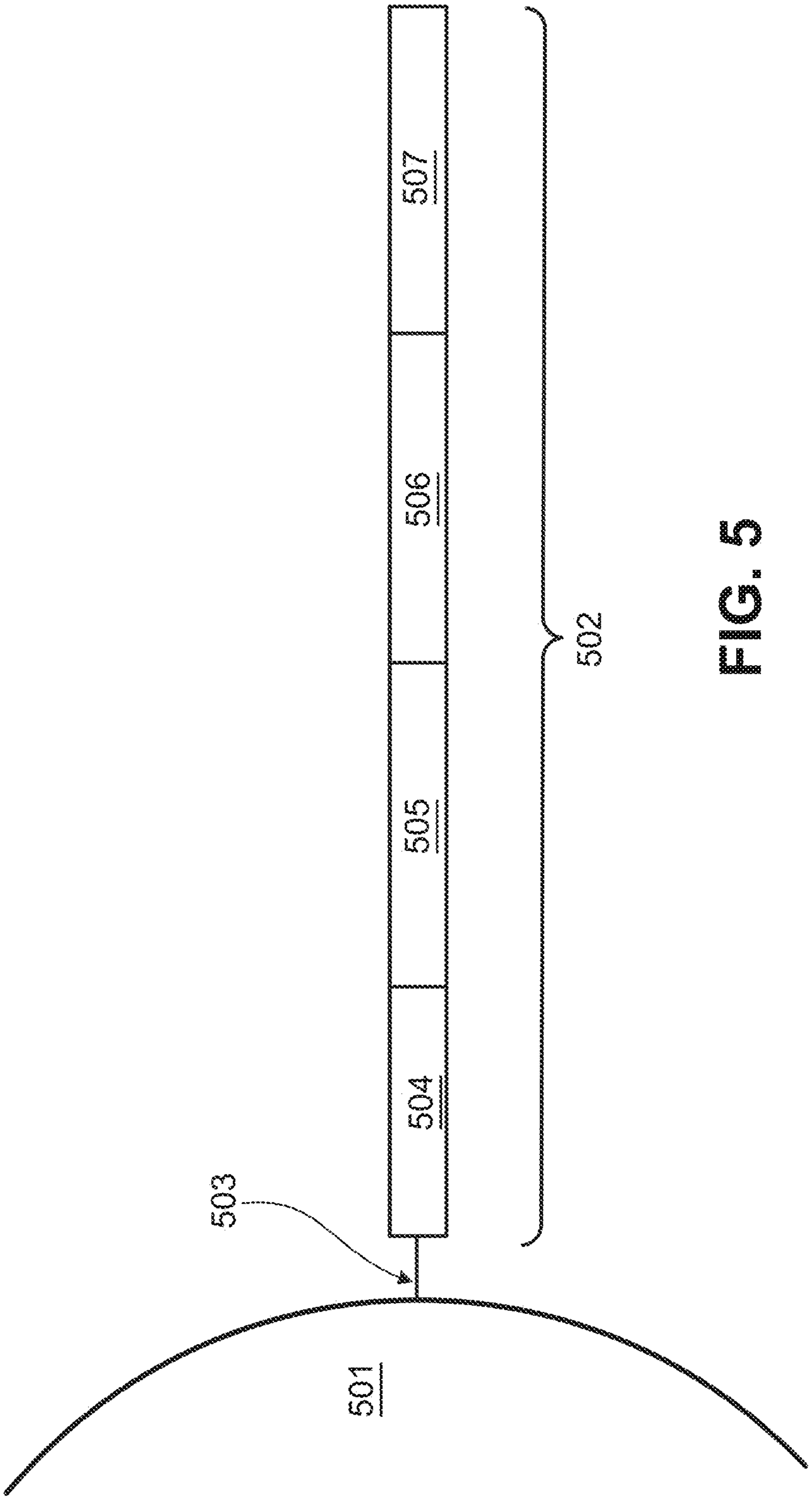
FIG. 5 is a schematic diagram showing an example of a barcoded capture probe, as described herein.

FIG. 5 is a schematic diagram showing an exemplary capture probe, as described herein. As shown, the capture probe 502 is optionally coupled to a feature 501 by a cleavage domain 503, such as a disulfide linker. The capture probe can include a functional sequence 504 that are useful for subsequent processing. The functional sequence 504 can include all or a part of sequencer specific flow cell attachment sequence (e.g., a P5 or P7 sequence), all or a part of a sequencing primer sequence, (e.g., a R1 primer binding site, a R2 primer binding site), or combinations thereof. The capture probe can also include a spatial barcode 505. The capture probe can also include a unique molecular identifier (UMI) sequence 506. While FIG. 5 shows the spatial barcode 505 as being located upstream (5') of UMI sequence 506, it is to be understood that capture probes wherein UMI sequence 506 is located upstream (5') of the spatial barcode 505 is also suitable for use in any of the methods described herein. The capture probe can also include a capture domain 507 to facilitate capture of a target analyte. The capture domain can have a sequence complementary to a sequence of a nucleic acid analyte. The capture domain can have a sequence complementary to a connected probe described herein. The capture domain can have a sequence complementary to a capture handle sequence present in an analyte capture agent. The capture domain can have a sequence complementary to a splint oligonucleotide. Such splint oligonucleotide, in addition to having a sequence complementary to a capture domain of a capture probe, can have a sequence complementary to a sequence of a nucleic acid analyte, a portion of a connected probe described herein, a capture handle sequence described herein, and/or a methylated adaptor described herein.

The functional sequences can generally be selected for compatibility with any of a variety of different sequencing systems, e.g., Ion Torrent Proton or PGM, Illumina sequencing instruments, PacBio, Oxford Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Ion Torrent Proton or PGM sequencing, Illumina sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 505 and functional sequences 504 is common to all of the probes attached to a given feature. In some embodiments, the UMI sequence 506 of a capture probe attached to a given feature is different from the UMI sequence of a different capture probe attached to the given feature.

In some embodiments, more than one analyte type (e.g., nucleic acids and proteins) from a biological sample can be detected (e.g., simultaneously or sequentially) using any appropriate multiplexing technique, such as those described in Section (IV) of PCT Publication No. WO2020/176788 and/or U.S. Patent Application Publication No. 2020/0277663.

In some cases, spatial analysis can be performed by attaching and/or introducing a molecule (e.g., a peptide, a lipid, or a nucleic acid molecule) having a barcode (e.g., a spatial barcode) to a biological sample (e.g., to a cell in a biological sample). In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis. In some embodiments, after attaching and/or introducing a molecule having a barcode to a biological sample, the biological sample can be physically separated (e.g., dissociated) into single cells or cell groups for analysis. Some such methods of spatial analysis are described in Section (III) of PCT Publication No. WO2020/176788 and/or U.S. Patent Application Publication No. 2020/0277663.

In some cases, spatial analysis can be performed by detecting multiple oligonucleotides that hybridize to an analyte. In some instances, for example, spatial analysis can be performed using RNA-templated ligation (RTL). Methods of RTL have been described previously. See, e.g., Credle et al., *Nucleic Acids Res.* 2017 Aug. 21; 45(14):e128. Typically, RTL includes hybridization of two oligonucleotides to adjacent sequences on an analyte (e.g., an RNA molecule, such as an mRNA molecule). In some instances, the oligonucleotides are DNA molecules. In some instances, one of the oligonucleotides includes at least two ribonucleic acid bases at the 3' end and/or the other oligonucleotide includes a phosphorylated nucleotide at the 5' end. In some instances, one of the two oligonucleotides includes a capture binding capture domain (e.g., a poly(A) sequence, a non-homopolymeric sequence). After hybridization to the analyte, a ligase (e.g., a T4 RNA ligase (Rnl2), a PBCV-1 DNA Ligase or Chorella virus DNA Ligase, a single-stranded DNA ligase, or a T4 DNA ligase) ligates the two oligonucleotides together, creating a ligation product. In some instances, the two oligonucleotides hybridize to sequences that are not adjacent to one another. For example, hybridization of the two oligonucleotides creates a gap between the hybridized oligonucleotides. In some instances, a polymerase (e.g., a DNA polymerase) can extend one of the oligonucleotides prior to ligation. After ligation, the ligation product is released from the analyte. In some instances, the ligation product is released using an endonuclease (e.g., RNAse H). In some instances, the ligation product is removed using heat. In some instances, the ligation product is removed using KOH. The released ligation product can then be captured by capture probes (e.g., instead of direct capture of an analyte) on an array, optionally amplified, and sequenced, thus determining the location and optionally the abundance of the analyte in the biological sample.

Figure 6:
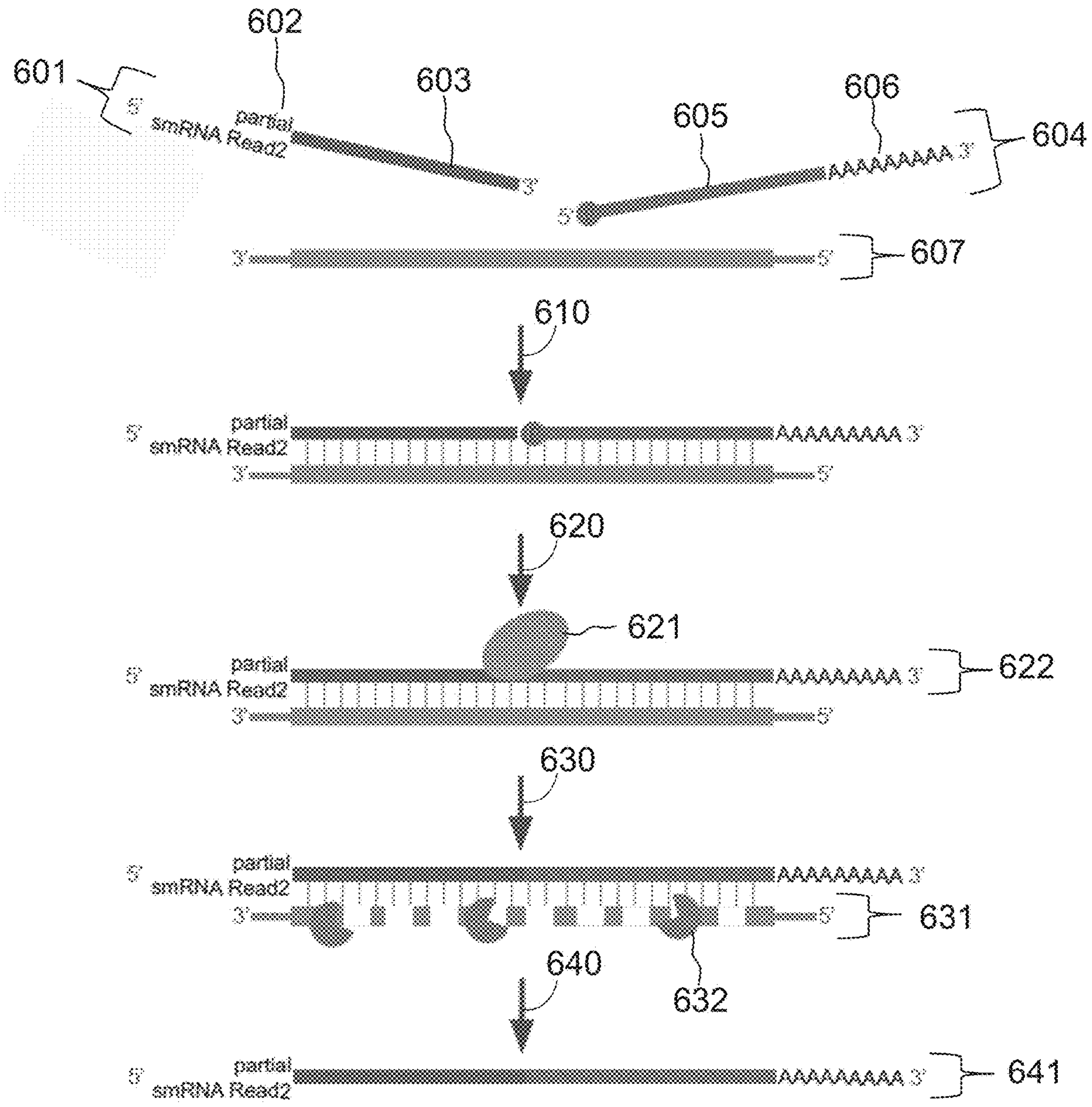
FIG. 6 is a schematic diagram showing an exemplary workflow for RNA-templated ligation.

A non-limiting example of templated ligation methods disclosed herein is depicted in FIG. 6. After a biological sample is contacted with a substrate including a plurality of capture probes and contacted with (a) a first probe 601 having a target-hybridization sequence 603 and a primer sequence 602 and (b) a second probe 604 having a target-hybridization sequence 605 and a capture domain (e.g., a poly-A sequence) 606, the first probe 601 and a second probe 604 hybridize 610 to an analyte 607. A ligase 621 ligates 620 the first probe to the second probe thereby generating a ligation product 622. The ligation product is released 630 from the analyte 631 by digesting the analyte using an endoribonuclease 632. The sample is permeabilized 640 and the ligation product 641 is able to hybridize to a capture probe on the substrate. Methods and composition for spatial detection using templated ligation have been described in PCT Publ. No. WO 2021/133849 A1, U.S. Pat. Nos. 11,332,790 and 11,505,828, each of which is incorporated by reference in its entirety.

In some embodiments, detection of one or more analytes (e.g., protein analytes) can be performed using one or more analyte capture agents. As used herein, an "analyte capture agent" refers to an agent that interacts with an analyte (e.g., an analyte in a biological sample) and with a capture probe (e.g., a capture probe attached to a substrate or a feature) to identify the analyte. In some embodiments, the analyte capture agent includes: (i) an analyte binding moiety (e.g., that binds to an analyte), for example, an antibody or antigen-binding fragment thereof; (ii) analyte binding moiety barcode; and (iii) an analyte capture sequence. As used herein, the term "analyte binding moiety barcode" refers to a barcode that is associated with or otherwise identifies the analyte binding moiety. As used herein, the term "analyte capture sequence" refers to a region or moiety configured to hybridize to, bind to, couple to, or otherwise interact with a capture domain of a capture probe. In some cases, an analyte binding moiety barcode (or portion thereof) may be able to be removed (e.g., cleaved) from the analyte capture agent. Additional description of analyte capture agents can be found in Section (II)(b)(ix) of PCT Publication No. WO2020/176788 and/or Section (II)(b)(viii) U.S. Patent Application Publication No. 2020/0277663.

Figure 7:
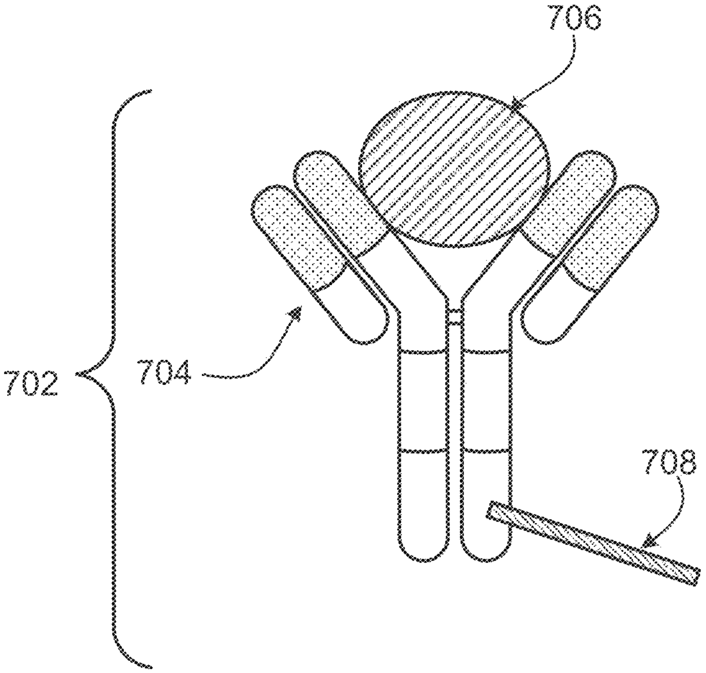
FIG. 7 is a schematic diagram of an exemplary analyte capture agent.

FIG. 7 is a schematic diagram of an exemplary analyte capture agent 702 comprised of an analyte-binding moiety 704 and an analyte-binding moiety barcode domain 708. The exemplary analyte-binding moiety 704 is a molecule capable of binding to an analyte 706 and the analyte capture agent is capable of interacting with a spatially-barcoded capture probe. The analyte-binding moiety can bind to the analyte 706 with high affinity and/or with high specificity. The analyte capture agent can include an analyte-binding moiety barcode domain 708, a nucleotide sequence (e.g., an oligonucleotide), which can hybridize to at least a portion or an entirety of a capture domain of a capture probe. The analyte-binding moiety barcode domain 708 can comprise an analyte binding moiety barcode and a capture handle sequence described herein. The analyte-binding moiety 704 can include a polypeptide and/or an aptamer. The analyte-binding moiety 704 can include an antibody or antibody fragment (e.g., an antigen-binding fragment).

Figure 8:
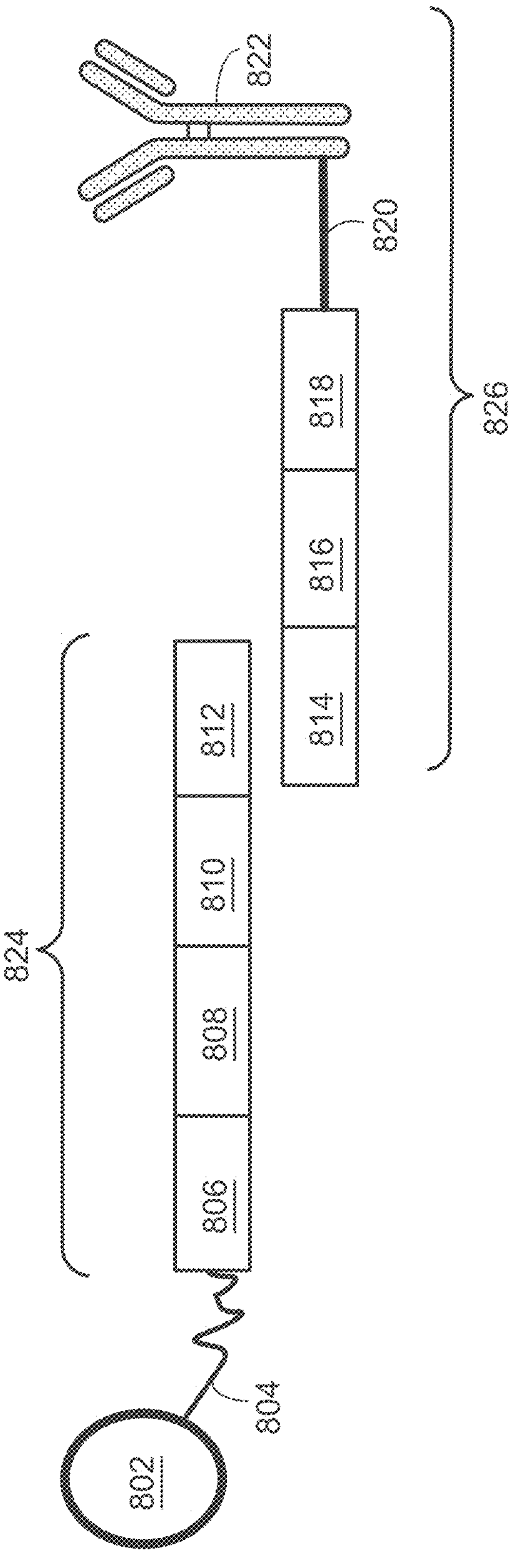
FIG. 8 is a schematic diagram depicting an exemplary interaction between a feature-immobilized capture probe 824 and an analyte capture agent 826.

FIG. 8 is a schematic diagram depicting an exemplary interaction between a feature-immobilized capture probe 824 and an analyte capture agent 826. The feature-immobilized capture probe 824 can include a spatial barcode 808 as well as functional sequences 806 and UMI 810, as described elsewhere herein. The capture probe can be affixed 804 to a feature (e.g., bead) or array 802. The capture probe can also include a capture domain 812 that is capable of binding to an analyte capture agent 826. The analyte capture agent 826 can include a functional sequence 818, analyte binding moiety barcode 816, and a capture handle sequence 814 that is capable of binding to the capture domain 812 of the capture probe 824. The analyte capture agent can also include a linker 820 that allows the capture agent barcode domain 816 to couple to the analyte binding moiety 822.

During analysis of spatial information, sequence information for a spatial barcode associated with an analyte is obtained, and the sequence information can be used to provide information about the spatial distribution of the analyte in the biological sample. Various methods can be used to obtain the spatial information. In some embodiments, specific capture probes and the analytes they capture are associated with specific locations in an array of features on a substrate. For example, specific spatial barcodes can be associated with specific array locations prior to array fabrication, and the sequences of the spatial barcodes can be stored (e.g., in a database) along with specific array location information, so that each spatial barcode uniquely maps to a particular array location.

Alternatively, specific spatial barcodes can be deposited at predetermined locations in an array of features during fabrication such that at each location, only one type of spatial barcode is present so that spatial barcodes are uniquely associated with a single feature of the array. Where necessary, the arrays can be decoded using any of the methods described herein so that spatial barcodes are uniquely associated with array feature locations, and this mapping can be stored as described above.

When sequence information is obtained for capture probes and/or analytes during analysis of spatial information, the locations of the capture probes and/or analytes can be determined by referring to the stored information that uniquely associates each spatial barcode with an array feature location. In this manner, specific capture probes and captured analytes are associated with specific locations in the array of features. Each array feature location represents a position relative to a coordinate reference point (e.g., an array location, a fiducial marker) for the array. Accordingly, each feature location has an "address" or location in the coordinate space of the array.

Some exemplary spatial analysis workflows are described in the Exemplary Embodiments section of PCT Publication No. WO2020/176788 and/or U.S. Patent Application Publication No. 2020/0277663. See, for example, the Exemplary embodiment starting with "In some non-limiting examples of the workflows described herein, the sample can be immersed . . . " of PCT Publication No. WO2020/176788 and/or U.S. Patent Application Publication No. 2020/0277663. See also, e.g., the Visium Spatial Gene Expression Reagent Kits User Guide (e.g., Rev F, dated January 2022); and/or the Visium Spatial Gene Expression Reagent Kits—Tissue Optimization User Guide (e.g., Rev E, dated February 2022).

In some embodiments, spatial analysis can be performed using dedicated hardware and/or software, such as any of the systems described in Sections (II)(e)(ii) and/or (V) of PCT Publication No. WO2020/176788 and/or U.S. Patent Application Publication No. 2020/0277663, or any of one or more of the devices or methods described in Sections Control Slide for Imaging, Methods of Using Control Slides and Substrates for, Systems of Using Control Slides and Substrates for Imaging, and/or Sample and Array Alignment Devices and Methods, Informational labels of PCT Publication No. WO2020/123320.

Suitable systems for performing spatial analysis can include components such as a chamber (e.g., a flow cell or sealable, fluid-tight chamber) for containing a biological sample. The biological sample can be mounted for example, in a biological sample holder. One or more fluid chambers can be connected to the chamber and/or the sample holder via fluid conduits, and fluids can be delivered into the chamber and/or sample holder via fluidic pumps, vacuum sources, or other devices coupled to the fluid conduits that create a pressure gradient to drive fluid flow. One or more valves can also be connected to fluid conduits to regulate the flow of reagents from reservoirs to the chamber and/or sample holder.

The systems can optionally include a control unit that includes one or more electronic processors, an input interface, an output interface (such as a display), and a storage unit (e.g., a solid state storage medium such as, but not limited to, a magnetic, optical, or other solid state, persistent, writeable and/or re-writeable storage medium). The control unit can optionally be connected to one or more remote devices via a network. The control unit (and components thereof) can generally perform any of the steps and functions described herein. Where the system is connected to a remote device, the remote device (or devices) can perform any of the steps or features described herein. The systems can optionally include one or more detectors (e.g., CCD, CMOS) used to capture images. The systems can also optionally include one or more light sources (e.g., LED-based, diode-based, lasers) for illuminating a sample, a substrate with features, analytes from a biological sample captured on a substrate, and various control and calibration media.

The systems can optionally include software instructions encoded and/or implemented in one or more of tangible storage media and hardware components such as application specific integrated circuits. The software instructions, when executed by a control unit (and in particular, an electronic processor) or an integrated circuit, can cause the control unit, integrated circuit, or other component executing the software instructions to perform any of the method steps or functions described herein.

In some cases, the systems described herein can detect (e.g., register an image) the biological sample on the array. Exemplary methods to detect the biological sample on an array are described in PCT Publication No. WO2021/102003 and/or U.S. Patent Application Publication No. 2021/0150707, each of which is incorporated herein by reference in their entireties.

Prior to transferring analytes from the biological sample to the array of features on the substrate, the biological sample can be aligned with the array. Alignment of a biological sample and an array of features including capture probes can facilitate spatial analysis, which can be used to detect differences in analyte presence and/or level within different positions in the biological sample, for example, to generate a three-dimensional map of the analyte presence and/or level. Exemplary methods to generate a two- and/or three-dimensional map of the analyte presence and/or level are described in PCT Publication No. WO2020/053655 and spatial analysis methods are generally described in PCT Publication No. WO2021/102039 and/or U.S. Patent Application Publication No. 2021/0155982, each of which is incorporated herein by reference in their entireties.

In some cases, a map of analyte presence and/or level can be aligned to an image of a biological sample using one or more fiducial markers, e.g., objects placed in the field of view of an imaging system which appear in the image produced, as described in the Substrate Attributes Section, Control Slide for Imaging Section of PCT Publication Nos. WO2020/123320, WO 2021/102005, and/or U.S. Patent Application Publication No. 2021/0158522, each of which is incorporated herein by reference in their entireties. Fiducial markers can be used as a point of reference or measurement scale for alignment (e.g., to align a sample and an array, to align two substrates, to determine a location of a sample or array on a substrate relative to a fiducial marker) and/or for quantitative measurements of sizes and/or distances.

Spatial Assay for Transposase Accessible Chromatin

The human body includes a large collection of diverse cell types, each providing a specialized and context-specific function. Understanding a cell's chromatin structure can reveal information about a cell's function. Open chromatin, or accessible chromatin, or accessible genomic DNA, is often indicative of transcriptionally active sequences, e.g., genes, in a particular cell. Further understanding the transcriptionally active regions within chromatin will enable identification of which genes contribute to a cell's function and/or phenotype.

Methods have been developed to study epigenomes, e.g., chromatin accessibility assays (ATAC-seq, CUT & RUN, Cleavage Under Targets and Tagmentation (CUT & Tag)) or identifying proteins associated with chromatin e.g., (ChIP-seq). These assays help identify, for example, regulators (e.g., cis regulators and/or trans regulators) that contribute to dynamic cellular phenotypes. See, e.g., CUT & RUN and CUT & Tag described in Skene and Henikoff, eLife 2017; 6:e21856; Meers et al., eLIFE (2019) 8:e46314; and Kaya-Okur et al., Nature Communications (2019):10, 1930, each of which is incorporated by reference in its entirety. See also, e.g., single-cell CUT & Tag described in Bartosovic et al., Nature Biotechnology (2021):39, 825-835; Deng et al. bioRxiv (2021) preprint doi: https://doi.org/10.1101/2021.03.11.434985, each of which is incorporated by reference in its entirety. While CUT & RUN and CUT & Tag have been invaluable in defining epigenetic variability within a cell population, conventional applications of these methods are limited in their ability to spatially resolve the three dimensional structures and associated genes that promote cellular variation.

Thus, the present disclosure relates generally to the spatial tagging and analysis of nucleic acids. In some instances, provided herein are methods that utilize a transposase enzyme fused to an antibody-binding moiety (e.g. an antibody-binding protein that contains an antibody-binding moiety, such as protein A, protein G, fusion of protein A and protein G, or functional equivalent thereof), to engage and fragment, for example, the accessible (e.g., open chromatin) genomic DNA and enable the simultaneous capture of DNA and RNA from a biological sample, thus revealing epigenomic insights regarding the structural features contributing to cellular regulation.

In some instances of any of the spatial analysis methods described herein, CUT & Tag based methods or methods based on assays for transposase-accessible chromatin using sequencing (ATAC-seq) is used to generate genome-wide chromatin accessibility maps. These genome-wide accessibility maps can be integrated with additional genome-wide profiling data (e.g., RNA-seq, ChIP-seq, Methyl-Seq) to produce gene regulatory interaction maps that facilitate understanding of transcriptional regulation. For example, interrogation of genome-wide accessibility maps can reveal the underlying transcription factors and the transcription factor motifs responsible for chromatin accessibility at a given genomic location. Correlating changes in chromatin accessibility with changes in gene expression (RNA-seq), changes in transcription factor (TF) binding (e.g., ChIP-seq) and/or changes in DNA methylation levels (e.g., Methyl-seq) can identify the transcription regulation driving these changes. In disease states, there is often an imbalance in this transcriptional regulation. Thus, analyzing both chromatin accessibility and, for example, gene expression using spatial analysis methods enables identification of causes underlying the imbalances in transcriptional regulation.

Accordingly, provided herein are methods for determining a location of accessible genomic DNA in a biological sample. In some instances, the method includes (a) providing the biological sample on an array comprising a plurality of capture probes, wherein a capture probe of the plurality of capture probes comprises: (i) a spatial barcode and (ii) a capture domain; (b) contacting a plurality of splint oligonucleotides to the biological sample, wherein a portion of a splint oligonucleotide of the plurality of splint oligonucleotides hybridizes to a portion of the capture domain; (c) contacting one or more antibodies, for example, antibodies that recognize a portion of a histone to the biological sample, (d) contacting a transposome complex to the biological sample, thereby generating fragmented and tagged genomic DNA (e.g., tagmented genomic DNA), wherein the transposome complex includes (i) an antibody-binding moiety (e.g. an antibody-binding protein), (ii) a transposase, (iii) a first transposon end sequence comprising a splint sequence that is substantially complementary to a portion of the splint oligonucleotide, and (iv) the second transposon end sequence comprising a functional sequence (collectively, (ii), (iii) and (iv) form a transposome); (d) hybridizing a transposon splint sequence of the fragmented genomic DNA to the splint oligonucleotide and ligating the transposon splint sequence of the fragmented genomic DNA to the capture domain, thereby generating a capture probe that is ligated to the fragmented genomic DNA; and (e) determining (i) all or part of a sequence of the spatial barcode or a complement thereof, and (ii) all or part of a sequence of the fragmented genomic DNA, or a complement thereof, and using the determined sequences of (i) and (ii) to determine and correlate the location of the accessible genomic DNA in the biological sample.

Also provided herein are methods for determining and correlating a location of accessible genomic DNA in a biological sample. In some instances, the method includes (a) providing the biological sample on an array comprising a plurality of capture probes, wherein a capture probe of the plurality of capture probes comprises: (i) a spatial barcode and (ii) a capture domain; (b) adding an antibody that binds to a chromatin protein to the biological sample; (c) binding a transposome-antibody-binding moiety (e.g. an antibody-binding protein that contains an antibody-binding moiety, such as protein A, protein G, or a fusion protein thereof) complex ("the complex") to the antibody, thereby generating fragmented genomic DNA, wherein the complex comprises: (i) a transposase, (ii) an antibody-binding moiety (e.g. an antibody-binding protein that contains an antibody-binding moiety, such as protein A, protein G, or a fusion protein thereof), (iii) a first transposon end sequence comprising a splint sequence that is substantially complementary to a portion of the a splint oligonucleotide, and (iv) a second transposon end sequence comprising a functional sequence; and (d) adding a plurality of splint oligonucleotides to the biological sample, wherein a portion of a splint oligonucleotide of the plurality of splint oligonucleotides hybridizes to a portion of the capture domain; (e) hybridizing the splint sequence of the fragmented genomic DNA to the splint oligonucleotide and hybridizing the splint oligonucleotide to the capture probe; (f) ligating the splint sequence of the fragmented genomic DNA to the capture domain; and (g) determining (i) all or part of a sequence of the spatial barcode or a complement thereof, and (ii) all or part of a sequence of the fragmented genomic DNA, or a complement thereof, and using the determined sequences of (i) and (ii) to determine the location of the accessible genomic DNA in the biological sample.

In any of the methods described herein, binding a transposome-antibody-binding moiety (e.g. an antibody-binding protein that contains an antibody-binding moiety, such as protein A, protein G, or a fusion protein thereof) complex ("the complex") to the antibody, thereby generating fragmented genomic DNA, is performed at room temperature. For example, room temperature can include any temperature between 22° C. to 30° C. In some instance, room temperature is 26° C., 27° C., or 28° C.

In any of the methods described herein, binding a transposome-antibody-binding moiety (e.g. an antibody-binding protein that contains an antibody-binding moiety, such as protein A, protein G, or a fusion protein thereof) complex ("the complex") to the antibody, thereby generating fragmented genomic DNA further comprises incubating the multi-complex added to the biological sample for one or more hours (e.g. 1, 2, 3, 4, 5, 6, 7, 8, 9, or 10 hours), for example, at room temperature.

In another embodiment of any of the methods described herein, binding a transposome-antibody-binding moiety (e.g. an antibody-binding protein that contains an antibody-binding moiety, such as protein A, protein G, or a fusion protein thereof) complex ("the complex") to the antibody, thereby generating fragmented genomic DNA further comprises incubating the multi-complex added to the biological sample for one or more days (e.g., 1, 2, 3, 4, 5, 6, 7, 8, 9, 10, 11, 12, 13, or 14 days), for example, at room temperature.

In some instances, step (d) and the step of determining (i) all or part of a sequence of the spatial barcode or a complement thereof, and (ii) all or part of a sequence of the fragmented genomic DNA, or a complement thereof, and using the determined sequences of (i) and (ii) to determine and correlate the location of the accessible genomic DNA in the biological sample are performed sequentially. In some instances, step (d) and the step of determining (i) all or part of a sequence of the spatial barcode or a complement thereof, and (ii) all or part of a sequence of the fragmented genomic DNA, or a complement thereof, and using the determined sequences of (i) and (ii) to determine and correlate the location of the accessible genomic DNA in the biological sample are performed simultaneously. For example, some tagmented DNA fragments can be captured with non-ligated transposon end sequences still hybridized. In such examples, the non-ligated transposon end sequences are released after capture of the tagmented DNA. In some instances, the non-ligated transposon end sequences are released prior to capture by the capture domain.

Also provided herein are methods for determining genomic DNA accessibility including (a) a biological sample on an array comprising a plurality of capture probes, wherein a capture probe of the plurality of capture probes comprises: (i) a spatial barcode and (ii) a capture domain; (b) contacting the biological sample with one or more antibodies, for example that will recognize and bind a portion of a histone, (d) contacting a transposome and/or transposome complex to the biological sample to insert transposon end sequences into accessible genomic DNA, thereby generating fragmented genomic DNA; (c) binding the transposon end sequences of the fragmented genomic DNA to the capture domain of the capture probe; (d) releasing one or more transposon end sequences not bound to the capture domain; (e) determining (i) all or a portion of a sequence of the spatial barcode or a complement thereof, and (ii) all or a portion of a sequence of the fragmented genomic DNA, or a complement thereof, and using the determined sequences of (i) and (ii) to determine a location of the accessible genomic DNA in the biological sample.

In some instances, steps (c) and (d) are performed sequentially. In some instances, steps (c) and (d) are performed simultaneously. For example, some tagmented DNA fragments can be captured with one or more transposon end sequences still hybridized. In such examples, the one or more transposon end sequences are released after capture of the tagmented DNA. In some instances, the one or more transposon end sequences are released prior to capture by the capture domain.

In some instances, provided herein are methods for spatial analysis of nucleic acids (e.g., genomic DNA, mRNA) in a biological sample. In some instances, an array is provided, wherein the array comprises a plurality of capture probes. In some instances, the capture probes may be attached directly to the substrate (e.g., an array comprising a substrate comprising a plurality of capture probes). In some instances, the capture probes may be attached indirectly to the substrate. For example, the capture probes can be attached to features on the substrate. In some instances, a feature is a bead. In some instances, the capture probes comprise a spatial barcode and a capture domain. In some instances, the capture probe can be partially double stranded. In some instances, the capture probe can bind a complementary oligonucleotide. In some instances, the complementary oligonucleotide (e.g., splint oligonucleotide) can have a single stranded portion. In some instances, the single stranded portion can bind fragmented (e.g., tagmented) DNA. In some instances, a biological sample is treated under conditions sufficient to make nucleic acids in cells of the biological sample (e.g., genomic DNA) accessible to transposon insertion (e.g., tagging the DNA fragments with transposon ends). In some instances, a transposon end sequence and a transposase enzyme (collectively, a transposome) are provided to the biological sample such that the transposon end sequence can be inserted into the genomic DNA of cells present in the biological sample. In some instances, the transposase enzyme of the transposome complex fragments the genomic DNA and transposon ends are attached to the ends of the genomic DNA fragments (e.g., "tagmenting").

In some instances, the biological sample comprising nucleic acids (e.g., genomic DNA, mRNA) is contacted to the substrate such that a capture probe can interact with the fragmented and tagged (e.g., tagmented) genomic DNA. In some instances, the biological sample comprising nucleic acids (e.g., genomic DNA, mRNA) is contacted with the substrate such that the capture probe can interact with both the tagmented genomic DNA and the mRNA present in the biological sample (e.g., a first capture probe can bind genomic DNA, a second capture probe can bind mRNA).

In some instances, the location of the capture probe on the substrate can be correlated to a location in the biological sample, thereby spatially determining the location of the tagmented genomic DNA. In some instances, the location of the capture probe on the substrate can be correlated to a location in the biological sample, thereby spatially determining the location of the tagmented genomic DNA and mRNA in the biological sample.

In some instances, where spatial determining the location of analytes includes a concurrent analysis of different types of analytes from a single cell or a subpopulation of cells within a biological sample (e.g., a tissue section), an additional layer of spatial information can be integrated into the genome regulatory interaction maps. In some instances, the spatial determining of analytes can be done on whole genomes. In some instances, the spatial profiling can be done on an immobilized biological sample.

Spatial Cleavage Under Targets and Tagmentation (CUT & Tag)

In some instances, the genome-wide chromatic accessibility maps can be generated by spatial CUT & Tag methods. Without being bound by theory, CUT & Tag uses a transposome that includes a hyperactive Tn5 transposase, or another transposase, fused to Protein A (pA-Tn5) or Protein G (pG-Tn5), thereby creating a protein A or protein G, or a combination thereof-transposome complex. The pA-Tn5 or pG-Tn5 complex further is loaded with sequencing adapters to bind to a target protein that is bound to genomic DNA. Non-limiting examples include those of SEQ ID NOs: 1-2, and other modified varieties known in the art. (See, for example, U.S. Pat. Nos. 9,790,476; 10,035,992; and 10,544,403, which are incorporated in their entirety herein). After binding, the complex cuts (i.e., digests) the DNA under the target protein. Released are DNA fragments that are ready for fragment capture on an array described herein, PCR enrichment, and DNA sequencing. For a detailed description of CUT & Tag, see, for e.g., Kaya-Okur et al. Nature Communications (2019):1930, which is incorporated by reference in its entirety.

In some instances, the genome-wide chromatin accessibility maps generated by spatial CUT & Tag can be used for cell type identification. For example, traditional cell type classification relies on mRNA expression levels but chromatin accessibility can be more adept at capturing cell identity. Furthermore, in some instances, correlations between transcriptionally active regions (e.g., open chromatin, accessible) with expression profiles (e.g., expression profiles of mRNA) can be determined in a spatial manner.

Spatial ATAC-seq

In some instances, the genome-wide chromatic accessibility maps can be generated by spatial ATAC-seq. In some instances, the genome-wide chromatin accessibility maps generated by spatial ATAC-seq can be used for cell type identification. Without being bound by theory, ATAC-seq maps a chromatin protein by binding of a specific antibody, and then tethering a Protein A/Micrococcal Nuclease (pA-MNase) fusion protein in permeabilized cells without cross-linking. MNase is activated by addition of calcium, and fragments are released into the supernatant for extraction of DNA, library preparation and paired-end sequencing. For a detailed description of ATAC-seq, see, for e.g., Skene and Henikoff (2017). Elife 6, e21856.

In some instances, the genome-wide chromatin accessibility maps generated by spatial ATAC-seq can be used for cell type identification. As indicated above for use with spatial CUT&Tag, traditional cell type classification can rely on mRNA expression levels but chromatin accessibility can be more adept at capturing cell identity. Furthermore, in some instances, correlations between transcriptionally active regions (e.g., open chromatin, accessible) with expression profiles (e.g., expression profiles of mRNA) can be determined in a spatial manner.

Permeabilizing the Biological Sample

The present disclosure generally describes methods of tagmenting genomic DNA to generate DNA fragments in a biological sample. In some examples, a chemical or enzymatic "pre-permeabilization" of biological samples immobilized on a substrate can be employed to make DNA in the biological sample accessible to a transposase enzyme (e.g. a transposome or a transposome antibody complex). In some instances, permeabilizing the biological sample can be a two-step process (e.g., pre-permeabilization treatment, followed by a permeabilization treatment). In some instances, permeabilizing the biological sample can be a one-step process (e.g., a single permeabilization treatment sufficient to permeabilize the cellular and nuclear membranes in the biological sample).

In some instances, pre-permeabilization can include an enzymatic or chemical condition. In some instances, pre-permeabilization can be performed with an enzyme (e.g., a protease). In some instances, in a non-limiting way, the protease can include trypsin, pepsin, dispase, papain, accuses, or collagenase. In some instances, pre-permeabilization can include an enzymatic treatment with pepsin. In some instances, pre-permeabilization can include pepsin in 0.5M acetic acid. In some instances, pre-permeabilization can include pepsin in Exonuclease-1 buffer. In some instances, the pH of the buffer can be acidic. In some instances, pre-permeabilization can include enzymatic treatment with collagenase. In some instances, pre-permeabilization can include collagenase in HBSS buffer. In some instances, the HBSS buffer can include bovine serum albumin (BSA). In some instances, pre-permeabilization can last for about 1 to minute to about 20 minutes. In some instances, pre-permeabilization can last for about 2, about 3, about 4, about 5, about 6, about 7, about 8, about 9, about 10, about 11, about 12, about 13, about 14, about 15, about 16, about 17, about 18, or about 19 minutes. In some instances, pre-permeabilization can last for about 10 minutes to about one hour. For example, in some instances, pre-permeabilization can last for about 20, about 30, about 40, or about 50 minutes.

In some instances, permeabilizing the biological sample comprises an enzymatic treatment. In some instances, the enzymatic treatment can be a pepsin enzyme, or a pepsin-like enzyme treatment. In some instances, the enzymatic treatment can be protease treatment. In some instances, enzymatic treatment can be performed in the presence of reagents. In some instances, the enzymatic treatment (e.g., pre-permeabilization) can include contacting the biological specimen with an acidic solution including a protease enzyme. In some instances, the reagent can be HCl. In some instances, the reagent can be acetic acid. In some instances, the concentration of HCl can be about 100 mM. In some instances, the about 100 mM HCl can have a pH of around, or about 1.0. In some instances, the additional reagent can be 0.5M acetic acid, having a pH of around, or about 2.5. It is noted that enzymatic treatment of the biological sample can have different effects on tagmentation. For example, enzymatic treatment with pepsin and 100 mM HCl can result in tagmentation of chromatin regardless of chromatin accessibility. In some instances, enzymatic treatment with pepsin and 0.5M acetic acid can result in tagmentation of chromatin that can retain a nucleosomal pattern indicative of tagmentation.

In some instances, the enzymatic treatment can comprise contacting the biological sample with a reaction mixture (e.g., solution) comprising an aspartyl protease (e.g., pepsin) in an acidic buffer, e.g., a buffer with a pH of about 4.0 or less, such as about 3.0 or less, e.g., about 0.5 to about 3.0, or about 1.0 to about 2.5. In some instances, the aspartyl protease is a pepsin enzyme, pepsin-like enzyme, or a functional equivalent thereof. Thus, any enzyme or combination of enzymes in the enzyme commission number 3.4.23.1.

In some instances, the enzymatic treatment (e.g., pre-permeabilization) can be performed using collagenase. In some instances, enzymatic treatment with collagenase can provide access to the genomic DNA for the transposase, transposome, or transposome antibody complex while preserving nuclear integrity. In some instances, pre-permeabilization (e.g., enzymatic treatment) with collagenase yields nucleosomal patterns generally associated with tagmentation. Collagenases can be isolated from *Clostridium histolyticum*. In some instances, enzymatic treatment with a zinc endopeptidase (e.g., collagenase) with reagents and under conditions suitable for proteolytic activity comprises a buffered solution with a pH of about 7.0 to about 8.0 (e.g., about 7.4). Collagenases are zinc endopeptidases and can be inhibited by either EDTA or EGTA, or both. Therefore, in some instances, the biological sample can be contacted with a zinc endopeptidase (e.g., collagenase) in the absence of a chelator of divalent cations, (e.g., EDTA, EGTA). In some instances, it can be useful to stop the zinc endopeptidase (e.g., collagenase) and the permeabilization step can be stopped (e.g., inhibited) by contacting the biological sample with a chelator of divalent cations (e.g., EDTA, EGTA).

In some instances, the zinc endopeptidase is a collagenase enzyme, collagenase-like enzyme, or a functional equivalent thereof. In such instances, any enzyme or combination of enzymes in the enzyme commission number 3.4.23.3 can be used in accordance with materials and methods described herein. In some instances, the collagenase is one or more collagenases from the following group, (UniProtKB/Swiss-Prot accession numbers): P43153/COLA_CLOPE; P43154/COLA_VIBAL; Q9KRJ0/COLA_VIBCH; Q56696/COLA_VIBPA; Q8D4Y9/COLA_VIBVU; Q9X721/COLG_HATHI; Q46085/COLH_HATHI; Q899Y1/COLT_CLOTE URSTH and functional variants and derivatives thereof (described herein), or a combination thereof.

Methods of permeabilizing biological samples are well known in the art. It will be known to a person skilled in the art that different sources of biological samples can be treated with different reagents (e.g., proteases, RNAses, detergents, buffers) and under different conditions (e.g., pressure, temperature, concentration, pH, time). In some instances, permeabilizing the biological sample can comprise reagents and conditions to sufficiently disrupt the cell membrane of the biological sample to capture nucleic acid (e.g., mRNA). In some instances, permeabilizing the biological sample can comprise reagents and conditions to sufficiently disrupt the nuclear membrane of the biological sample to capture nucleic acid (e.g., genomic DNA). In some instances, commercially available proteases isolated from their native (e.g., animal, microbial) source can be used. In some instances, proteases produced recombinantly (e.g., bacterial expression system) can be used. In some instances, pre-permeabilizing and permeabilizing a biological sample can be a one-step process (e.g., enzymatic treatment). In some instances, pre-permeabilizing and permeabilizing a biological sample can be a two-step process (e.g., enzymatic treatment, followed by chemical or detergent treatment).

In some instances, the chemical permeabilization conditions comprise contacting the biological specimen with an alkaline solution, e.g. a buffered solution with a pH of about 8.0 to about 11.0, such as about 8.5 to about 10.5 or about 9.0 to about 10.0, e.g. about 9.5. In some instances, the buffer is a glycine-KOH buffer. Other buffers are known in the art.

In some instances, a biological sample can be treated with a detergent following an enzymatic treatment (e.g., permeabilization following a pre-permeabilization step). Detergents are known in the art. Any suitable detergent can be used, including, in a non-limiting way NP-40 or equivalent, Digitonin, Tween-20, IGEPAL-40 or equivalent, Saponin, SDS, Pitsop2, or combinations thereof. In some instances, a biological sample can be treated with other chemicals known to permeabilize cellular membranes. As further exemplified in the examples below, detergents described herein can be used at a concentration of between about 0.01% to about 0.1%. In some instances, detergents described herein can be used at a concentration of about 0.2%, about 0.3%, about 0.4%, about 0.5%, about 0.6%, about 0.7%, about 0.8%, or about 0.9%. In some instances, detergents described herein can be used at a concentration of about 1.1% to about 10% or more. In some instances, detergents described herein can be used at a concentration of about 2%, about 3%, about 4%, about 5%, about 6%, about 7%, about 8%, or about 9%, or about 10%.

Additional methods for sample permeabilization are described, for example, in Jamur et al., Method Mol. Biol. 588:63-66, 2010, the entire contents of which are incorporated herein by reference. Any suitable method for biological sample permeabilization can generally be used in connection with the biological samples described herein.

Different sources of biological samples can be treated with different reagents (e.g., proteases, RNAses, detergents, buffers) and under different suitable conditions (e.g., pressure, temperature, concentration, pH, time) to achieve sufficient pre-permeabilization and permeabilization to capture nucleic acids (e.g., genomic DNA, mRNA).

In some instances, the reaction mixture (e.g., solution) including the proteases described herein can contain other reagents, (e.g., buffer, salt, etc.) sufficient to ensure that the proteases are functional. For instance, the reaction mixture can further include an albumin protein, (e.g., BSA). In some instances, the reaction mixture (e.g., solution) including the collagenase enzyme (or functional variant or derivative thereof) includes an albumin protein, (e.g., BSA).

In some instances, there is one or more wash steps between pre-permeabilization and permeabilization of a biological sample. For example, it may be preferential to wash as much of the pre-permeabilization solution off of the biological sample prior to adding a permeabilization solution. Therefore, in some instances the biological sample is washed, for example with a SSC wash solution, after pre-permeabilization to remove the pre-permeabilization reagents and before applying permeabilization reagents to the biological sample. In some instances, the permeabilization solution is removed from the biological sample prior to the addition of the transposome or transposome complex reagents for tagmentation of the released genomic DNA. One or more washes may also be performed post permeabilization and pre-tagmentation, for example using a SSC solution. In some instances, there are no wash steps between permeabilization of the biological sample and tagmentation of the genomic DNA.

Tagmentation and Spatial Analysis

Transposase enzymes and transposons can be utilized in methods of spatial genomic analysis. Generally, transposition is the process by which a specific genetic sequence (e.g., a transposon sequence) is relocated from one place in a genome to another. Many transposition methods and transposable elements are known in the art (e.g., DNA transposons, retrotransposons, autonomous transposons, non-autonomous transposons). One non-limiting example of a transposition event is conservative transposition. Conservative transposition is a non-replicative mode of transposition in which the transposon is completely removed from the genome and reintegrated into a new locus, such that the transposon sequence is conserved, (e.g., a conservative transposition event can be thought of as a "cut and paste" event) (See, e.g., Griffiths A. J., et. al., Mechanism of transposition in prokaryotes. An Introduction to Genetic Analysis (7th Ed.). New York: W. H. Freeman (2000)).

In one example, transposition can occur when a transposase enzyme binds a sequence flanking the ends of the transposome (e.g., a recognition sequence, e.g., a mosaic end sequence). A transposome (e.g., a transposition complex) forms and the endogenous DNA can be manipulated into a pre-excision complex such that, for example, two transposase enzymes can interact to form a dimer when the transposase is a Tn5 transposase or a tetramer when the transposase is a Mu transposase. In some instances, when the transposases interact with the DNA, double stranded breaks are introduced into the DNA resulting in the insertion of the transposon sequence. The transposase enzymes can locate and bind a target site in the DNA, create a double stranded break, and insert the transposon end sequence (See, e.g., Skipper, K. A., et. al., DNA transposon-based gene vehicles-scenes from an evolutionary drive, *J Biomed Sci.,* 20: 92 (2013) doi:10.1186/1423-0127-20-92). Canonical transposases include Tn5. Alternative cut and paste transposases include Tn552 (College, et al, J. BacterioL, 183: 2384-8, 2001; Kirby C et al, Mol. Microbiol, 43: 173-86, 2002), Tyl (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol, 204:27-48, 1996), Tn/O and IS10 (Kleckner N, et al, Curr Top Microbiol Immunol, 204:49-82, 1996), Mariner transposase (Lampe D J, et al, EMBO J., 15: 5470-9, 1996), Tel (Plasterk R H, Curr. Topics Microbiol. Immunol, 204: 125-43, 1996), P Element (Gloor, G B, Methods Mol. Biol, 260: 97-114, 2004), Tn3 (Ichikawa & Ohtsubo, J Biol. Chem. 265: 18829-32, 1990), bacterial insertion sequences (Ohtsubo & Sekine, Curr. Top. Microbiol. Immunol. 204: 1-26, 1996), retroviruses (Brown, et al, Proc Natl Acad Sci USA, 86:2525-9, 1989), and retrotransposon of yeast (Boeke & Corces, Annu Rev Microbiol. 43:403-34, 1989). More examples include ISS, TnlO, Tn903, IS911, and engineered versions of transposase family enzymes (Zhang et al, (2009) PLoS Genet. 5:e1000689. Epub 2009 Oct. 16; Wilson C. et al (2007) J. Microbiol. Methods 71:332-5).

Transposome-mediated fragmentation and tagging ("tagmentation") is a process of transposase-mediated fragmentation and tagging of DNA. A transposome is a complex of a transposase enzyme and DNA which comprises a transposon end sequence (also known as "transposase recognition sequence" or "mosaic end" (MEs)). In some methods of spatial genomic analysis, DNA is fragmented in such a manner that a functional sequence such as a sequence complementary to a capture domain of a capture probe (e.g., capture domain of a splint oligonucleotide) is inserted into the fragmented DNA (e.g., the fragmented DNA is "tagged"), such that the sequence (e.g. an adapter) can hybridize to the capture probe. In some instances, the capture probe is present on a substrate. In some instances, the capture probe (e.g., a capture probe and a splint oligonucleotide) is present on a feature. A transposome dimer, in the case of the Tn5 transposome, is able to simultaneously fragment DNA based on its transposon recognition sequences and ligate the transposon sequences from the transposome to the fragmented DNA (e.g., tagmented DNA). This system has been adapted using hyperactive transposase enzymes and modified DNA molecules (adaptors) comprising MEs to fragment DNA and tag both strands of DNA duplex fragments with functional DNA molecules (e.g., primer binding sites). For instance, the Tn5 transposase may be produced as purified protein monomers. Tn5 transposase is also commercially available (e.g., manufacturer Illumina, Illumina.com, Catalog No. 15027865, TD Tagment DNA Buffer Catalog No. 15027866). These can be subsequently loaded with the oligonucleotides of interest, e.g., ssDNA oligonucleotides containing MEs (e.g., transposon sequences) for Tn5 recognition and additional functional sequences (e.g., Nextera adapters, e.g., primer binding sites) are annealed to form a dsDNA mosaic end oligonucleotide (MEDS) that is recognized by Tn5 during dimer assembly (e.g., transposome dimerization). In some instances, a hyperactive Tn5 transposase can be loaded with adapters (e.g., oligonucleotides of interest) which can simultaneously fragment and tag a genome with the sequences. As used herein, the term "tagmentation" refers to a step in the Assay for Transposase Accessible Chromatin using sequencing (ATAC-seq) or a step in the CUT & Tag assay. (See, e.g., Buenrostro, J. D., Giresi, P. G., Zaba, L. C, Chang, H. Y., Greenleaf, W. J., Transposition of native chromatin for fast and sensitive epi genomic profiling of open chromatin, DNA-binding proteins and nucleosome position, *Nature Methods,* 10 (12): 1213-1218 (2013)). ATAC-seq identifies regions of open chromatin using a hyperactive prokaryotic Tn5-transposase, which preferentially inserts into accessible chromatin and tags the sites with adaptors (Buenrostro, J. D., et. al., Transposition of native chromatin for fast and sensitive epigenomic profiling of open chromatin, DNA-binding proteins and nucleosome position. *Nat Methods,* 10: 1213-1218 (2013)).

As used herein "accessible chromatin" or "open chromatin" or "accessible genomic DNA" refers to portions of a genome that are nucleosome-depleted regions that can be bound by proteins and play various roles in nuclear organization, gene transcription, and are generally considered transcriptionally active regions of DNA (Zhang, Q., et al., Genome-wide open chromatin regions and their effects on the regulation of silk protein genes in *Bombyx mori, Scientific Reports,* 7: 12919 (2017).

In some instances, the step of fragmenting the genomic DNA in cells of the biological sample comprises contacting the biological sample containing the genomic DNA with the transposase enzyme (e.g., a transposome or transposome antibody complex, e.g., a reaction mixture (e.g., solution)) including a transposase, transposome, or transposome antibody complex), under any suitable conditions. In some instances, such suitable conditions result in the tagmentation of the genomic DNA of cells present in the biological sample. Typical conditions will depend on the transposase enzyme and/or antibody complexed to the transposome used and can be determined using routine methods known in the art. Therefore, suitable conditions can be conditions (e.g., buffer, salt, concentration, pH, temperature, time conditions) under which the transposase enzyme is functional, e.g., in which the transposase enzyme displays transposase activity, particularly tagmentation activity, in the biological sample.

The term "functional", as used herein in reference to transposase enzymes, is meant to include instances in which the transposase enzyme can show some reduced activity relative to the activity of the transposase enzyme in conditions that are optimum for the enzyme, e.g., in the buffer, salt and temperature conditions recommended by the manufacturer. Thus, the transposase can be considered to be "functional" if it has at least about 50%, e.g., at least about 60%, about 70%, about 80%, about 85%, about 90%, about 95%, about 96%, about 97%, about 98%, about 99%, or about 100%, activity relative to the activity of the transposase in conditions that are optimum for the transposase enzyme.

In one non-limiting example, the reaction mixture comprises a transposome and/or a transposome antibody complex in a buffered solution (e.g., Tris-acetate) having a pH of about 6.5 to about 8.5, e.g., about 7.0 to about 8.0 such as about 7.5. Additionally or alternatively, the reaction mixture can be used at any suitable temperature, such as about 10° to about 55° C., e.g., about 10° to about 54°, about 11° to about 53°, about 12° to about 52°, about 13° to about 51°, about 14° to about 50°, about 15° to about 49°, about 16° to about 48°, about 17° to about 47° C., e.g., about 10°, about 12°, about 15°, about 18°, about 20°, about 22°, about 25°, about 28°, about 30°, about 33°, about 35°, about or 37° C., preferably about 30° to about 40° C., e.g., about 37° C. In some instances, the transposome can be contacted with the biological sample for about 10 minutes to about one hour. In some instances, the transposome can be contacted with the biological sample for about 20, about 30, about 40, or about 50 minutes. In some instances, the transposome can be contacted with the biological sample for about 1 hour to about 4 hours.

In some instances, the transposase enzyme of the transposome complex is a Tn5 transposase, or a functional derivate or variant thereof (See, e.g., Reznikoff et al, WO 2001/009363, U.S. Pat. Nos. 5,925,545, 5,965,443, 7,083,980, and 7,608,434, and Goryshin and Reznikoff, J. Biol. Chem. 273:7367, (1998), which are herein incorporated by reference). In some instances, the Tn5 transposase is a hyper Tn5 transposase, or a functional derivate or variate thereof (U.S. Pat. No. 9,790,476, incorporated herein by reference). For example, the Tn5 transposase can be a fusion protein (e.g., a Tn5 fusion protein). Tn5 is a member of the RNase superfamily of proteins which includes retroviral integrases. The Tn5 transposon is a composite transposon in which two near-identical insertion sequences (IS50L and IS50R) flank three antibiotic resistance genes. Each IS50 contains two inverted 19-bp end sequences (ESs), an outside end (OE) and an inside end (IE). Wild-type Tn5 transposase enzyme is generally inactive (e.g., low transposition event activity). However, amino acid substitutions can result in hyperactive variants or derivatives. In one non-limiting example, amino acid substitution, L372P, substitutes a leucine amino acid for a proline amino acid which results in an alpha helix break, thus inducing a conformational change to the C-terminal domain. The alpha helix break separates the C-terminal domain and N-terminal domain sufficiently to promote higher transposition event activity (See, Reznikoff, W. S., Tn5 as a model for understanding DNA transposition, *Mol Microbiol,* 47(5): 1199-1206 (2003)). Other amino acid substitutions resulting in hyperactive Tn5 are known in the art. For example, the improved avidity of the modified transposase enzyme (e.g., modified Tn5 transposase enzyme) for the repeat sequences for OE termini (class (1) mutation) can be achieved by providing a lysine residue at amino acid 54, which is glutamic acid in wild-type Tn5 transposase enzyme (See U.S. Pat. No. 5,925,545). The mutation strongly alters the preference of the modified transposase enzyme (e.g., modified Tn5 transposase enzyme) for OE termini, as opposed to IE termini. The higher binding of this mutation, known as EK54, to OE termini results in a transposition rate that is about 10-fold higher than is seen with wild-type transposase enzyme (e.g., wild type Tn5 transposase enzyme). A similar change at position 54 to valine (e.g., EV54) also results in somewhat increased binding/transposition for OE termini, as does a threonine to proline change at position 47 (e.g., TP47; about 10-fold higher) (See U.S. Pat. No. 5,925,545).

Other examples of modified transposase enzymes (e.g., modified Tn5 transposase enzymes) are known. For example, a modified Tn5 transposase enzyme that differs from wild-type Tn5 transposase enzyme in that it binds to the repeat sequences of the donor DNA with greater avidity than wild-type Tn5 transposase enzyme and also is less likely than the wild-type transposase enzyme to assume an inactive multimeric form (U.S. Pat. No. 5,925,545, which is incorporated by reference in its entirety). Furthermore, techniques generally describing introducing any transposable element (e.g., Tn5) from a donor DNA (e.g., adapter sequence, e.g., Nextera adapters (e.g., top and bottom adapter) into a target are known in the art. (See, e.g., U.S. Pat. No. 5,925,545). Further study has identified classes of mutations resulting in a modified transposase enzyme (e.g., modified Tn5 transposase enzyme) (See, U.S. Pat. No. 5,965,443, which is incorporated by reference in its entirety). For example, a modified transposase enzyme (e.g., modified Tn5 transposase enzyme) with a "class 1 mutation" binds to repeat sequences of donor DNA with greater avidity than wild-type Tn5 transposase enzyme. Additionally, a modified transposase enzyme (e.g., modified Tn5 transposase enzyme) with a "class 2 mutation" is less likely than the wild-type Tn5 transposase enzyme to assume an inactive multimeric form. It has been shown that a modified transposase enzyme that contains both a class 1 and a class 2 mutation can induce at least about 100-fold (+10%) more transposition than the wild-type transposase enzyme, when tested in combination with an in vivo conjugation assay as described by Weinreich, M. D., "Evidence that the cis Preference of the Tn5 Transposase is Caused by Nonproductive Multimerization," Genes and Development 8:2363-2374 (1994), incorporated herein by reference (See e.g., U.S. Pat. No. 5,965,443). Further, under sufficient conditions, transposition using the modified transposase enzyme (e.g., modified Tn5 transposase enzyme) may be higher. A modified transposase enzyme containing only a class 1 mutation can bind to the repeat sequences with sufficiently greater avidity than the wild-type Tn5 transposase enzyme such that a Tn5 transposase enzyme induces about 5- to about 50-fold more transposition than the wild-type transposase enzyme, when measured in vivo. A modified transposase enzyme containing only a class 2 mutation (e.g., a mutation that reduces the Tn5 transposase enzyme from assuming an inactive form) is sufficiently less likely than the wild-type Tn5 transposase enzyme to assume the multimeric form that such a Tn5 transposase enzyme also induces about 5- to about 50-fold more transposition than the wild-type transposase enzyme, when measured in vivo (See U.S. Pat. No. 5,965,443)

Other methods of using a modified transposase enzyme (e.g., modified Tn5 transposase enzyme are further generally described in U.S. Pat. Nos. 5,965,443 and 9,790,476. For example, a modified transposase enzyme could provide selective markers to target DNA, to provide portable regions of homology to a target DNA, to facilitate insertion of specialized DNA sequences into target DNA, to provide primer binding sites or tags for DNA sequencing, or to facilitate production of genetic fusions for gene expression. Studies and protein domain mapping, as well as, to bring together other desired combinations of DNA sequences (combinatorial genetics) (U.S. Pat. No. 5,965,443).Still other methods of inserting a transposable element (e.g., transposon) at random or semi-random locations in chromosomal or extra-chromosomal nucleic acid are known. For example, methods including a step of combining in a biological sample nucleic acid (e.g., genomic DNA) with a synaptic complex that comprises a Tn5 transposase enzyme complexed with a sequence comprising a pair of nucleotide sequences adapted for operably interacting with Tn5 transposase enzyme and a transposable element (e.g., transposon) under conditions that mediate transposition events into the genomic DNA. In this method, a synaptic complex can be formed in vitro under conditions that disfavor or prevent synaptic complexes from undergoing a transposition event. The frequency of transposition (e.g., transposition events) can be increased by using either a hyperactive transposase enzyme (e.g., a mutant transposase enzyme) or a transposable element (e.g., transposon) that contains sequences well adapted for efficient transposition events in the presence of a hyperactive transposase enzyme (e.g., hyperactive Tn5 transposase enzyme), or both (U.S. Pat. No. 6,159,736, which is incorporated herein by reference).

In some instances, the transposome can be fused to (e.g., joined with, linked to, associated with, complexed to) anantibody-binding moiety to form a transposome-antibody binding moiety (e.g. an antibody-binding protein that contains an antibody-binding moiety, such as protein A, protein G, or a fusion protein thereof) complex, or a "transposome complex". In some instances, the transposome is fused to protein A. In some instances, the transposome is fused to protein G. In some instances, the transposome is fused to a fusion protein of protein A and protein G (protein A/G). A variety of linkers (e.g. amino acid linkers) that are flexible or rigid can be used. Linkers can include cyclopeptide linkers, disulfide linkers, and protease-sensitive linkers that are cleavable. In some instances, the transposome is fused to the antibody with a DDDKEF$(GGGGS)_4$ linker. Other fusion protein linkers are described in Chen et al. (2013) Adv. Drug Deliv. Rev. 65(10):1357-1369, which is incorporated by reference in its entirety. The transposome can also be fused to the antibody or protein binding moiety post translational linkers, such as generation of covalent or non-covalent bonds.

An antibody can bind to a target protein that may be associated with chromatin (e.g. bound to), for example a transcription factor, histones, histone PTMs, nucleosomes, ChAPs, and DNA methylation, or any protein binding moiety. A protein that binds in a general manner to antibodies, such as protein A, protein G, a fusion protein, a fusion between protein A and protein G, protein L, protein Y, or functional derivatives thereof, can be used to bind to the antibody that is bound to the target protein. The protein biding moiety can include biotin, glutathione-S-transferase (GST), etc. In some instances, the antibody binding protein can be protein A, or a functional derivative thereof. In some instances, the antibody binding protein is protein G, or a functional derivative thereof.

Methods, compositions, and kits for treating nucleic acid, and in particular, methods and compositions for fragmenting and tagging DNA using transposon compositions are described in detail in U.S. Patent Application Publication No. US 2010/0120098, U.S. Patent Application Publication No. US2011/0287435, and Satpathy, A. T., et. al., Massively parallel single-cell chromatin landscapes of human immune cell development and intratumoral T-cell exhaustion, *Nat Biotechnol.,* 37, 925-936 (2019), the contents of which are herein incorporated by reference in their entireties.

Any transposase enzyme with tagmentation activity, e.g., any transposase enzyme capable of fragmenting DNA and inserting oligonucleotides (e.g., adapters, e.g. Nextera index adapters) to the ends of the fragmented (e.g., tagmented) DNA, can be used. In some instances, the transposase is any transpose capable of conservative transposition. In some instances, the transposase is a cut and paste transposase. Other kinds of transposase are known in the art and are within the scope of this disclosure. For example, suitable transposase enzymes include, without limitation, Mos-1, HyperMu™, Ts-Tn5, Ts-Tn5059, Hermes, Tn7, a *vibhar* species transposase (See e.g., U.S. Patent Application No. 20120301925A1 and WO 2015/069374, the contents of which are herein incorporated by reference in their entireties), or any functional variant or derivative of the previously listed transposase enzymes.

In some instances, a hyperactive variant of the Tn5 transposase enzyme is capable of mediating the fragmentation of double-stranded DNA and ligation of synthetic oligonucleotides (e.g., Nextera adapters) at both 5' ends of the DNA in a reaction that takes a short period of time (e.g., about 5 minutes). However, as wild-type end sequences have a relatively low activity, they are sometimes replaced in vitro by hyperactive mosaic end (ME) sequences. A complex of the Tn5 transposase with 19-bp ME facilitates transposition, provided that the intervening DNA is long enough to bring two of these sequences close together to form an active Tn5 transposase enzyme homodimer.

In some instances, the Tn5 transposase enzyme, or functional variant or derivative thereof, comprises an amino acid sequence having at least 80% sequence identity to SEQ. ID NO. 1. In some instances, the Tn5 transposase enzyme, or functional variant or derivative thereof, comprises an amino acid sequence having a sequence identity of at least about 90, 91, 92, 93, 94, 95, 96, 97, 98, or 99% amino acid sequence identity to SEQ ID NO. 1.

In some instances, the transposase enzyme is a Mu transposase enzyme, or a functional variant or derivative thereof.

The adaptors (e.g., Nextera adaptors) in the complex with the transposase enzyme (e.g., that form part of the transposome, e.g., MEDS described herein) can include partially double stranded oligonucleotides. In some instances, there is a first adapter and a second adapter. In some instances, the first adapter can be complexed with a first monomer. In some instances, the second adapter can be complexed with a second monomer. In some instances, the first monomer complexed with the first adapter and the second monomer complexed with the second monomer can be assembled to form a dimer. In some instances, the double stranded portion of the adaptors contains transposon end sequences (e.g., Mosaic End (ME)) sequences. In some instances, the single stranded portion of the adaptors (e.g., Nextera index adapters) (5' overhang) contains the functional domain or sequence to be incorporated in the tagmented DNA. In some instances, the adapters can be Nextera adapters (e.g., index adapter) (for example, reagents including, Nextera DNA Library Prep Kit for ATAC-seq (no longer available), TDE-1 Tagment DNA Enzyme (Catalog No. 15027865), TD Tagment DNA Buffer (Catalog No. 15027866), available from Illumina, Illumina.com). In some instances, the sequence incorporated into the tagmented DNA is a sequence complementary to a capture domain of a capture probe. In some instances, the sequence complementary to the capture domain of the capture probe is a transposon end sequence. In such instances, the functional domain is on the strand of the adaptor that will be ligated to the capture probe. In other words, the functional domain can be located upstream (e.g., 5' to) the ME sequence, e.g., in the 5' overhang of the adapter.

The adaptors (e.g., Nextera index adapters, e.g., first and second adapters) ligated to the tagmented DNA can be any suitable sequence. For example, the sequence can be a viral sequence. In some instances, the sequence can be a CRISPR sequence. In some instances, the adaptor (e.g., oligonucleotides) ligated to the tagmented DNA can be a CRISPR guide sequence. In some instances, the CRISPR guide sequence can target a sequence of interest (e.g., genomic locus of interest e.g., gene specific).

In some instances, the ME sequence is a Tn5 transposase recognition sequence. In some instances, the mosaic end (e.g., ME) sequence is a Mu transposase recognition sequence.

In some instances, a composition comprising a transposase enzyme (e.g., any transposase enzyme described herein) complexed with adapters (e.g., first and second adapters complexed with first and second monomers, respectively) comprising transposon end sequences (e.g., mosaic end sequences) is used in a method for spatially tagging nucleic acids in a biological sample. In some instances, a composition comprising a transposase enzyme further comprises a domain that binds to a capture probe as described herein (e.g., Nextera adapter, e.g., first adapter) and a second adapter is used in a method for spatially tagging nucleic acids of a biological sample, such as any of the methods described herein.

In some instances, the transposase enzyme can be in the form of a transposome comprising adaptors (MEDS) in which the 5' overhang can be phosphorylated. In some instances, the adaptors (e.g., Nextera adaptors, e.g., first and second adapters) may be phosphorylated prior to their assembly with the transposase enzyme to form the transposome. In some instances, phosphorylation of adaptors can occur when complexed with a transposase enzyme (e.g., phosphorylation in situ in the transposome).

In some instances, the 5' overhang of the adaptor is not phosphorylated prior to its assembly in the transposome. In such instances, the 5' overhang can have accessible 5' hydroxyl groups outside of the mosaic-end transposase sequence. In some instances, phosphorylation of the 5' overhang of the assembled transposome complexes can be achieved by exposing these 5' ends of transposome complexes to a polynucleotide kinase (e.g., T4-polynucleotide kinase (T4-PNK)) in the presence of ATP.

In some instances, tagmenting genomic DNA of the biological sample with a transposome (e.g., any of the transposomes described herein) can comprise a further step of phosphorylating the 5' ends of the adaptors (e.g., the 5' overhangs of the Nextera adaptors, e.g., MEDS) in the transposome complex.

In some instances, methods provided herein comprise a step of providing a transposome that has been treated to phosphorylate the 5' ends of the adaptors (e.g., the 5' overhangs of the Nextera adaptors (e.g., first and second adapters), e.g., MEDS) in the transposome complex, thus fragmenting the biological sample with a transposome that has been treated to phosphorylate the 5' ends of the adaptors in the transposome complex.

In some instances, the transposome (e.g., the transposase dimer complexed with adapters) can be linked to an antibody or peptide with a protein binding domain. In some instances, the antibody is protein A, protein G, a fusion protein of all or parts of protein A and protein G, or derivatives thereof.

Any suitable enzyme and/or conditions can be used to phosphorylate the 5' ends of the adaptors (e.g., the 5' overhangs of the adaptors, e.g., MEDS) in the transposome complex, e.g., T4-PNK or T7-PNK. In some instances, the phosphorylation reaction can be carried out by contacting the transposome with a polynucleotide kinase (e.g., T4-PNK or T7-PNK) in a buffered solution (e.g., Tris-HC1, pH about 7.0 to about 8.0, e.g., about 7.6) at about 20 to about 40° C., e.g., about 25 to about 37° C., for about 1 to about 60 minutes, e.g., about 5 to about 50, about 10 to about 40, about 20 to about 30 minutes.

In some instances, gap filling and ligating breaks can be performed on the fragmented (e.g., tagmented) DNA. For example, the Tn5 transposition event results in a 9 base pair gap between an inserted transposon end sequence and the genomic DNA. In some instances, the gap filling is performed between the inserted transposon end sequence and fragmented genomic DNA.

In some instances, the transposon end sequences adjacent to the 9 base pair gap followed by the fragmented genomic DNA are released. In some examples, the transposon end sequences adjacent to the gap are released (e.g., removed) from the fragmented genomic DNA (e.g., released from the complementary transposon end sequence). In some instances, the released transposon end sequences are not ligated to the splint oligonucleotide (e.g., non-ligated transposon end sequences). In some instances, the non-ligated transposon end sequences are released with a heat gradient. In some instances, the ligated transposon end sequences are ligated to the capture probe. In some instances, the splint oligonucleotide is hybridized to the capture domain of the capture probe, or a portion thereof, and the remaining transposon end sequence (e.g., ligated transposon end sequence). In some instances, a gap filling reaction is performed. In some instances, gap filling occurs between the splint oligonucleotide and the fragmented genomic DNA. For example, a gap filling polymerase can fill the gap between the splint oligonucleotide and the fragmented genomic DNA (e.g., a portion of which included the released transposon end sequence).

In some instances, the non-ligated transposon end sequences (e.g., transposon end sequences adjacent to 9 base pair gap) are released with a heat gradient from about 20° C. to about 90° C., from about 25° C. to about 85° C., from about 30° C. to about 80° C., from about 35° C. to about 75° C., from about 40° C. to about 75° C., from about 45° C. to about 75° C., 50° C. to about 75° C., or about 50° C. to about 70° C. In some instances, releasing the non-ligated transposon end sequences occurs at about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., or about 90° C.

In some instances, releasing the non-ligated transposon end sequences (e.g., transposon end sequences adjacent to the 9 base pair gap) are released with a heat gradient for about 10 minutes to about 150 minutes, from about 20 minutes to about 140 minutes, from about 30 minutes to about 130 minutes, from about 40 minutes to about 120 minutes, from about 40 minutes to about 110 minutes, from about 50 minutes to about 110 minutes, from about 60 minutes to about 100 minutes, from about 70 minutes to about 90 minutes, from about 10 minutes, about 15 minutes, about 20 minutes, about 25 minutes, about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes, about 120 minutes, about 125 minutes, about 130 minutes, about 135 minutes, about 140 minutes, about 145 minutes, about 150 minutes, about 155 minutes, about 160 minutes, about 165 minutes, about 170 minutes, about 175 minutes, about 180 minutes, about 185 minutes, about 190 minutes, about 195 minutes, about 200 minutes, about 205 minutes, about 210 minutes, about 215 minutes, about 220 minutes, about 225 minutes, about 230 minutes, about 235 minutes, about 240 minutes, about 245 minutes, or about 250 minutes.

In some instances, spatially tagging the genomic DNA can be performed by insertion of the transposon sequence into the genomic DNA with adapters described herein. An amplification step can be performed with primers to the adapters (e.g., inserted adapters into the genomic DNA). The amplified products can contain accessible genomic DNA which can be spatially tagged by methods described herein.

In some instances, spatially tagging the genomic DNA can be performed by transposome complexes immobilized on the surface of the substrate. In some instances, spatially tagging the genomic DNA can be performed by transposome complexes immobilized on a feature (e.g., a bead). In some instances, the transposome complexes are assembled prior to adding the biological sample to the substrate or features. In some instances, the transposome complexes are assembled after adding the biological sample to the substrate or features on a substrate. For example, a spatially barcoded substrate (e.g., array) can include a plurality of capture probes that include a Mosaic End sequence (e.g., a transposase recognition sequence). The Mosaic End sequence can be at the 3' end of the capture probe (e.g., the capture probe is immobilized by its 5' end and the Mosaic End sequence is at the 3' most end of the capture probe). The Mosaic End sequence can be a Mosaic End sequence for any of the transposase enzymes described herein. The Mosaic End sequence (e.g., a transposase recognition sequence) can be hybridized to a reverse complement sequence (e.g., oligonucleotide). For example, the reverse complement sequence (e.g., reverse complement to the Mosaic End sequence) can hybridize to the Mosaic End sequence thereby generating a portion of double stranded DNA on the capture probe. The reverse complement to the Mosaic End sequence (e.g., oligonucleotide) can be provided to the spatially barcoded array prior to the biological sample being provided to the substrate. In some instances, the reverse complement to the Mosaic End sequence can be provided after the biological sample has been provided to the substrate. Transposase enzymes can be provided to the substrate and assemble at the double stranded portion of the capture probe (e.g., reverse complement oligonucleotide and the Mosaic End sequence hybridized to each other) thereby generating a transposome complex. For example, a transposome homodimer can be formed at the double stranded portion of the capture probe. Additionally, a transposase and antibody, or a transposase complexed to an antibody or protein binding moiety) can be provided to the substrate and assembled at the double stranded portion of the capture probe (e.g., reverse complement oligonucleotide and the Mosaic End sequence hybridized to each other) thereby generating a transposome complex. A biological sample can be provided to the substrate such that the position of the capture probe on the substrate can be correlated with a position (e.g., location) in the biological sample. The transposome complexes or transposome complex can fragment (e.g., tagment) and spatially tag the genomic DNA.

In some instances, spatially tagging genomic DNA can be performed by hybridizing a single stranded capture probe to the tagmented DNA. In some instances the single stranded capture probe can be a degenerate sequence. In some instances, the single stranded capture can be a random sequence. The single stranded capture probe can have a functional domain, a spatial barcode, a unique molecular identifier, a cleavage domain, or combinations thereof. The single stranded capture probe (e.g., random sequence, degenerate sequence) can non-specifically hybridize tagmented genomic DNA, thereby spatially capturing the tagmented DNA. Methods for extension reactions are known in the art and any suitable extension reaction method described herein can be performed.

Figure 9:
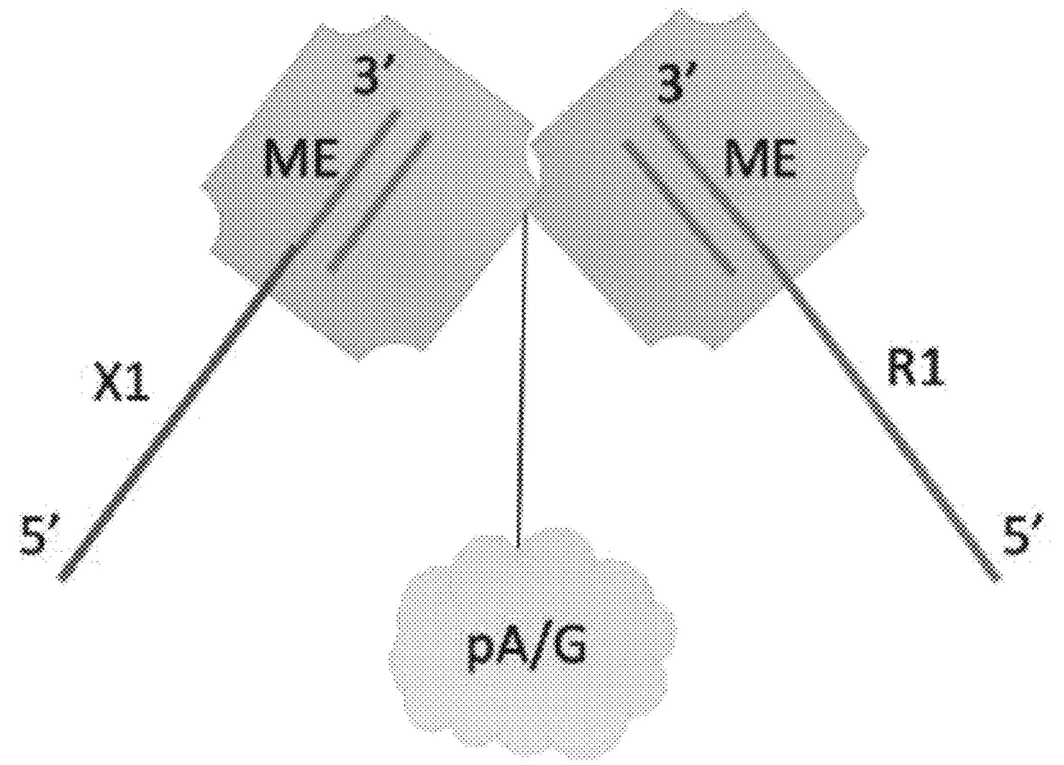
FIG. 9 shows an exemplary transposome complex. For example, a transposome, depicted here as a Tn5 transposome, can be conjugated to an antibody-binding protein, such as protein A (pA) or protein G (pG), thereby creating a transposome-antibody-binding protein complex, such as a protein A/G-transposome complex. ME: mosaic ends; X1: sequence complimentary to a splint oligo; pA/G: protein A antibody, protein G antibody-binding protein, or an antibody-binding protein A/protein G fusion; R1: read 1.

In other instances, tagmented DNA can be captured by the capture domain of the capture probe by binding (e.g., hybridizing) a poly(A) tailed tagmented DNA (e.g., by including a sequence complementary to a capture probe on one or more adaptors or recognition sequences (e.g., X1 as shown in FIG. 9).

In some instances, after fragmenting the genomic DNA, gap filing (e.g., no strand displacement) polymerases and ligases can repair gaps and ligate breaks in the tagmented DNA. In some instances, a sequence complementary to the capture domain can be introduced to the fragmented DNA. For example, a poly(A) tail can be added to the tagmented DNA, such that the capture domain (e.g., poly(T) sequence) of the capture probe can bind (e.g., hybridize) to the poly(A) tailed tagmented DNA (See, e.g., WO 2012/140224, which is incorporated herein by reference). In some instances, a poly(A) tail is added to the tagmented by a terminal transferase enzyme. In some instances, the terminal transferase enzyme is a terminal deoxynucleotidyl transferase (TdT), or a mutant variant thereof. TdT is an independent polymerase (e.g., it does not require a template molecule) that can catalyze the addition of deoxynucleotides to the 3' hydroxyl terminus of DNA molecules. Other template independent polymerases are known in the art. For example, Polymerase θ, or a mutant variant thereof, can be used as a terminal transferase enzyme (See, e.g., Kent, T., Polymerase θ is a robust terminal transferase that oscillates between three different mechanisms during end-joining, eLIFE, 5: e13740 doi: 10.7554/eLife.13740, (2016)). Other methods of introducing a poly(A) tail are known in the art. In some instances, a poly(A) tail can be introduced to the tagmented DNA by a non-proof reading polymerase. In some instances, a poly (A) tail can be introduced to the fragmented DNA by a polynucleotide kinase.

In some instances, the TDT enzyme will generate tagments with a 3' poly(A) tail, thereby mimicking the poly(A) tail of an mRNA. In some instances, the capture domain (e.g., poly(T) sequence) of the capture probe would interact with the poly(A) tail of the mRNA and the generated (e.g., synthesized) poly(A) tail added to the fragmented (e.g., tagmented) DNA, thereby simultaneously capturing the fragmented DNA (e.g., tagmented DNA) and the mRNA transcript. The generated (e.g., synthesized) poly(A) tail on the fragmented DNA (e.g., tagmented DNA) could be between about 10 nucleotides to about 30 nucleotides long. The generated (e.g., synthesized) poly(A) tail on the fragmented DNA (e.g., tagmented DNA) could be about 11, about 12, about 13, about 14, about 15, about 16, about 17, about 18, about 19, about 20, about 21, about 22, about 23, about 24, about 25, about 26, about 27, about 28, or about 29 nucleotides long.

Splint Oligonucleotides

As used herein, the term "splint oligonucleotide" refers to an oligonucleotide that, when hybridized to other polynucleotides, acts as a "splint" (e.g., splint helper probe) to position the polynucleotides next to one another so that they can be ligated together. In some instances, the splint oligonucleotide is DNA or RNA. The splint oligonucleotide can include a nucleotide sequence that is partially complementary to nucleotide sequences from two or more different oligonucleotides. In some instances, the splint oligonucleotide assists in ligating a "donor" oligonucleotide and an "acceptor" oligonucleotide. In some instances, an RNA ligase, a DNA ligase, or other ligase can be used to ligate two nucleotide sequences together.

In some instances, the splint oligonucleotide can be between about 10 and about 50 nucleotides in length, e.g., between about 10 and about 45, about 10 and about 40, about 10 and about 35, about 10 and about 30, about 10 and about 25, or about 10 and about 20 nucleotides in length. In some instances, the splint oligonucleotide can be between about 15 and about 50, about 15 and about 45, about 15 and about 40, about 15 and about 35, about 15 and about 30, about 15 and about 30, or about 15 and about 25 nucleotides in length.

In some instances, the fragmented DNA can include a sequence that is added (e.g., ligated) during fragmentation of the DNA. For example, during a transposition event (e.g., a Tn5 transposition event) an additional sequence (e.g., transposon end sequences) can be attached (e.g., covalently attached, e.g., via a ligation event) to the fragmented DNA (e.g., fragmented genomic DNA, e.g., tagmented genomic DNA). In some instances, the splint oligonucleotide can have a sequence that is complementary (e.g., a capture domain) to the fragmented DNA (e.g., fragmented genomic DNA, e.g., fragmented genomic DNA that includes a sequence that is added during fragmentation of the DNA, e.g. a first adapter attached during fragmentation of the DNA, e.g., a transposon end sequence) and a sequence that is complementary to the capture domain of the capture probe. In some instances, the splint oligonucleotide can be viewed as part of the capture probe. For example, the capture probe can be partially double stranded where a portion of the capture probe can function as a splint oligonucleotide that binds a portion of the capture probe (e.g., dsDNA portion) and can have a single strand portion that can bind (e.g., capture domain) the fragmented DNA (e.g., fragmented genomic DNA e.g., tagmented, e.g., an adapter attached during fragmentation of the DNA, e.g., a Nextera adapter). The first adapter sequence (e.g., the sequence attached to the fragmented DNA complementary to the capture domain, e.g., Nextera adapter) can be any suitable sequence. In some instances, the adapter sequence can be between about 15 and 25 nucleotides long. In some instances, the adapter sequence can be about 16, about 17, about 18, about 19, about 20, about 21, about 22, about 23, or about 24 nucleotides long.

In some instances, a splint oligonucleotide can include a sequence that is complementary (e.g., capture domain) to the first adapter attached to the fragmented DNA (e.g., tagmented DNA). In some instances, the splint oligonucleotide includes a sequence that is not perfectly complementary to the first adapter (e.g., Nextera adapter) attached to the fragmented DNA (e.g., tagmented DNA), but is still capable of hybridizing the first adapter sequence (e.g., sequence complementary to the capture domain) ligated on to the fragmented DNA (e.g., Nextera adapter).

Any of a variety of capture probes having capture domains that hybridize to a splint oligonucleotide can be used in accordance with materials and methods described herein. As described herein, a capture domain is a domain on a capture probe capable of hybridizing the splint oligonucleotide to form a partially double stranded capture probe. For example, a single stranded capture probe can have a sequence complementary (e.g., capture domain) to a portion of the splint oligonucleotide, such that a partially double stranded capture probe is formed with a single stranded portion capable of binding the inserted transposon end sequences. In some instances, a splint oligonucleotide includes a sequence that is complementary (e.g., at least partially complementary) to the capture domain of the capture probe.

In some instances, the splint oligonucleotide includes a sequence that is not perfectly complementary to the capture domain of the capture probe, but is still capable of hybridizing the capture domain of the capture probe. In some instances, the splint oligonucleotide can hybridize to both the transposon end sequence (e.g., additional sequence attached to the tagmented DNA) and the capture domain of the capture probe via its sequence complementary to the capture domain. In such instances, where the splint oligonucleotide can hybridize to both the transposon end sequence (e.g., Nextera adapter, additional sequence attached to the fragmented DNA e.g., tagmented DNA), and the capture domain of the capture probe, the splint oligonucleotide can be viewed as part of the capture probe.

In some instances, the splint oligonucleotide can have a capture domain that is homopolymeric. For example, the capture domain can be a poly(T) capture domain.

In some instances, a splint oligonucleotide can facilitate ligation of the tagmented DNA and the capture probe. Any variety of suitable ligases known in the art or described herein can be used. In some instances, the ligase is T4 DNA ligase. In some instances, the ligation reaction can last for about 1 to about 5 hours. In some instances, the ligation reaction can last for about 2, about 3, or about 4 hours. In some instances, after ligation, strand displacement polymerization can be performed. In some instances, a DNA polymerase can be used to perform the strand displacement polymerization. In some instances, the DNA polymerase is DNA polymerase I.

Multiplex Analysis

The present disclosure describes methods for permeabilizing biological samples under conditions sufficient to allow tagmentation of genomic DNA. The genomic DNA, or accessible chromatin, also known as open chromatin, can be tagmented with a transposome complex (e.g. a transposase and an antibody-binding moiety, bound to an antibody bound to, for example, a histone; or a multi-complex of a transposase, antibody-binding moiety, and an antibody, the complex bound to, for example, a histone). The tagmented genomic DNA can be captured via a capture probe (e.g., a capture probe and a splint oligonucleotide), however, at times it can be useful to simultaneously capture tagmented genomic DNA and other nucleic acids (e.g., mRNA). For example, expression profiles of transcripts can be correlated, anti-correlated, or not correlated with open (e.g. accessible) chromatin. Put another way, the presence of transcripts can correlate with open chromatin (e.g., accessible chromatin) corresponding to the genes (e.g., genomic DNA) from which the RNA transcripts were transcribed.

The present disclosure also describes methods regarding the simultaneous capture of tagmented genomic DNA and mRNA or protein on spatially barcoded arrays from biological samples (e.g., fresh or frozen tissue samples). Methods of detecting RNA molecules having poly(A) sequences, proteins, and derivatives of RNA molecules (e.g., RTL products) have been described previously in WO 2020/176788 and in U.S. Patent Application Publication Nos. 2020/0277663, 2021/0285046 and 2021/0285036, each of which is incorporated by reference in its entirety.

For example, multiplex capture (e.g. capturing genomic DNA, DNA, RNA and/or mRNA) can be performed on a spatially barcoded array having a plurality of capture probes immobilized on a substrate surface. The plurality of capture probes can have substantially the same capture sequence (e.g. a poly(T) capture sequence) and can capture both tagmented gDNA or mRNA.

Alternatively, multiplex capture can be performed on a spatially barcoded array having multiple pluralities of capture probes immobilized on a substrate surface (e.g. different types of capture probes). In some instance, tagmented genomic DNA (e.g. tagmented with a transposome complex or a multi-complex) can be captured on the array using a splint oligo, as described above. In some instances, the splint oligo is capable of hybridizing to both a capture probe on an array and to the tagmented DNA. In some instances, the capture probes have capture sequences that are specific to either tagmented DNA or RNA molecules or derivatives of RNA molecules (e.g. RTL products). In some cases, the capture probes for the RNA molecules or derivatives of RNA molecules (e.g. RTL products) are poly(T) sequences.

In any of the methods described herein, the feature with a plurality of capture probes can be on a substrate. The capture probes can have spatial barcodes corresponding to a position (e.g., location) on the substrate. In some instances, the capture probes can further have a unique molecular identifier, one or more functional domains, and a cleavage domain, or combinations thereof. In some instances, the capture probe includes a capture domain. In some instances, the capture probe can be a homopolymeric sequence. For example, in a non-limiting way, the homopolymeric sequence can be a poly(T) sequence. In some instances, nucleic acid (e.g., mRNA) can be captured by the capture domain by binding (e.g., hybridizing) of poly(A) tails of mRNA transcripts. Tagmented genomic DNA can also be captured by the capture domain of the capture probe by binding (e.g., hybridizing) a poly(A) tailed tagmented genomic DNA (e.g., by including a sequence complementary to a capture probe on one or more adaptors or recognition sequences (e.g., X1 as shown in FIG. 9).

In some instances, after fragmenting the genomic DNA and optionally capturing RNA molecules having poly(A) sequences or derivatives of RNA molecules (e.g. via RTL products), gap filing (e.g., no strand displacement) polymerases and ligases can repair gaps and ligate breaks in the tagmented DNA. In some instances, a sequence complementary to the capture domain can be introduced to the fragmented DNA. For example, a poly(A) tail can be added to the tagmented DNA, such that the capture domain (e.g., poly(T) sequence) of the capture probe can bind (e.g., hybridize) to the poly(A) tailed tagmented DNA (See, e.g., WO 2012/140224, which is incorporated herein by reference). In some instances, a poly(A) tail is added to the tagmented DNA by a terminal transferase enzyme. In some instances, the terminal transferase enzyme is a terminal deoxynucleotidyl transferase (TdT), or a mutant variant thereof. TdT is an independent polymerase (e.g., it does not require a template molecule) that can catalyze the addition of deoxynucleotides to the 3' hydroxyl terminus of DNA molecules. Other template independent polymerases are known in the art. For example, Polymerase θ, or a mutant variant thereof, can be used as a terminal transferase enzyme (See, e.g., Kent, T., Polymerase θ is a robust terminal transferase that oscillates between three different mechanisms during end-joining, eLIFE, 5: e13740 doi: 10.7554/eLife.13740, (2016)). Other methods of introducing a poly (A) tail are known in the art. In some instances, a poly(A) tail can be introduced to the tagmented DNA by a non-proof reading polymerase. In some instances, a poly(A) tail can be introduced to the fragmented DNA by a polynucleotide kinase. The captured RNA molecules (e.g. via RTL products) lack gaps and are substantially not affected by the gap-filling process used on the tagmented DNA.

In some instances, the TDT enzyme will generate tagments with a 3' poly(A) tail, thereby mimicking the poly(A) tail of an mRNA. In some instances, the capture domain (e.g., poly(T) sequence) of the capture probe would interact with the poly(A) tail of the mRNA and the generated (e.g., synthesized) poly(A) tail added to the fragmented (e.g., tagmented) DNA, thereby simultaneously capturing the fragmented DNA (e.g., tagmented DNA) and the mRNA transcript. The generated (e.g., synthesized) poly(A) tail on the fragmented DNA (e.g., tagmented DNA) could be between about 10 nucleotides to about 30 nucleotides long. The generated (e.g., synthesized) poly(A) tail on the fragmented DNA (e.g., tagmented DNA) could be about 11, about 12, about 13, about 14, about 15, about 16, about 17, about 18, about 19, about 20, about 21, about 22, about 23, about 24, about 25, about 26, about 27, about 28, or about 29 nucleotides long.

In some instances, provided herein are methods of multiplexing that capture both gDNA and RNA. In some instances, in addition to methods of associating gDNA (either using a splint oligonucleotide or via hybridization directly), the methods of detecting RNA include hybridizing the analyte (e.g., RNA) or a portion thereof to the capture domain; and determining (i) all or part of a sequence of the spatial barcode or a complement thereof, and (ii) all or part of a sequence of the analyte, or a complement thereof, and using the determined sequences of (i) and (ii) to determine the abundance and the location of the analyte in the biological sample. Methods of RNA capture have been described previously in WO 2020/176788 and in U.S. Patent Application Publication No. 2020/0277663, each of which is incorporated by reference. These methods generally include tissue staining and imaging, cDNA synthesis, second strand synthesis and denaturation, cDNA amplification, library construction, and sequencing.

In some instances, the methods can include determining abundance and location of a second analyte in the biological sample by detecting an analyte derivative such as an RTL product. In some instances, at the same time as capture of gDNA, the multiplex methods can include contacting a first templated ligation (RTL) probe and a second RTL probe with the biological sample, wherein the first RTL probe and the second RTL probe each comprise sequences that are substantially complementary to adjacent sequences of the second analyte, and wherein the second probe comprises a capture probe capture domain that is complementary to all or part of the capture domain; (b) hybridizing the first probe and the second probe to the second analyte; (c) generating an RTL ligation product by ligating the first probe and the second probe; (d) releasing the RTL ligation product from the second analyte; (e) hybridizing the RTL ligation product to the capture domain; and (f) determining (i) all or part of the sequence of the RTL ligation product bound to the capture domain, or a complement thereof, and (ii) all or part of the sequence of the spatial barcode, or a complement thereof, and using the determined sequences of (i) and (ii) to identify determine the location of the second analyte in the biological sample.

Detection of gDNA using methods described herein can be achieved concurrently with RNA templated ligation. In some cases, sample processing for determining the location of tagmented gDNA can occur before, after, or concurrently with the sample processing for determining the location of RNA or RNA-derived products (e.g. via RTL products). In some instances, both RTL probes and transposome complexes or RTL probes and multi-complexes can be added to the biological sample on a spatially barcoded array at the same time. In some instances, RTL probes are added to the biological sample on a spatially barcoded array before the transposome complexes or multi-complexes are added. In some instances, RTL probes are added to the biological sample on a spatially barcoded array after the transposome complexes or multi-complexes are added.

In some instances, one of the RTL probes includes a poly(A) sequence, or a complement thereof. In some instances, the poly(A) sequence, or a complement thereof, is on the 5' end of one of the RTL probes. In some instances, the poly(A) sequence, or a complement thereof, is on the 3' end of one of the RTL probes. In some instances, one RTL probe includes a degenerate or UMI sequence. In some instances, the UMI sequence is specific to a particular target or set of targets. In some instances, the UMI sequence, or a complement thereof, is on the 5' end of one of the RTL probe. In some instances, the UMI sequence, or a complement thereof, is on the 3' end of one of the RTL probe.

After addition of the RTL probes, RTL probes hybridize to target mRNA and are ligated together. After ligation of the RTL probes, an endonuclease such as RNAse H is added to the sample. RNAse H digests both the RNA analyte and the undesirable RNA. In some instances, at least one of the RTL probes includes a probe capture sequence such as a poly-A sequence, an oligo-d(T) sequence, or a particular capture sequence (in the setting of targeted RNA analysis).

In some instances, the first RTL probe hybridizes to an analyte and a second RTL probe hybridizes to an analyte in proximity to the first RTL probe. Hybridization can occur at a target having a sequence that is 100% complementary to the probe RTL probe(s). In some instances, hybridization can occur at a target having a sequence that is at least (e.g., at least about) 80%, at least (e.g., at least about) 85%, at least (e.g., at least about) 90%, at least (e.g., at least about) 95%, at least (e.g., at least about) 96%, at least (e.g., at least about) 97%, at least (e.g., at least about) 98%, or at least (e.g., at least about) 99% complementary to the RTL probe (s). After hybridization, in some instances, the first RTL probe is extended. After hybridization, in some instances, the second RTL probe is extended. For example, in some instances a first RTL probe hybridizes to a target sequence upstream of a second RTL probe, whereas in other instances a first RTL probe hybridizes to a target sequence downstream of a second RTL probe.

In some instances, methods disclosed herein include a wash step after hybridizing the first and the second RTL probes. The wash step removes any unbound probes and can be performed using any technique known in the art. In some instances, a pre-Hybridization buffer is used to wash the sample. In some instances, a phosphate buffer is used. In some instances, multiple wash steps are performed to remove unbound probes. For example, it is advantageous to decrease the amount of unhybridized probes present in a biological sample as they may interfere with downstream applications and methods.

In some instances, after hybridization of the RTL probes (e.g., the first and the second RTL probes) to the target analyte, the RTL probes are ligated together, creating a single ligated probe that is complementary to the target analyte. Ligation can be performed enzymatically or chemically, as described herein. For example, the first and second RTL probes are hybridized to the first and second target regions of the analyte, and the RTL probes are subjected to a ligation reaction to ligate them together. For example, the probes may be subjected to an enzymatic ligation reaction using a ligase (e.g., T4 RNA ligase (Rn12), a SplintR ligase, or a T4 DNA ligase). See, e.g., Zhang L., et al.; Archaeal RNA ligase from *Thermoccocus kodakarensis* for template dependent ligation RNA Biol. 2017; 14(1): 36-44 for a description of KOD ligase.

In some instances, adenosine triphosphate (ATP) is added during the ligation reaction. DNA ligase-catalyzed sealing of nicked DNA substrates is first activated through ATP hydrolysis, resulting in covalent addition of an AMP group to the enzyme. After binding to a nicked site in a DNA duplex, the ligase transfers this AMP to the phosphorylated 5'-end at the nick, forming a 5'-5' pyrophosphate bond. Finally, the ligase catalyzes an attack on this pyrophosphate bond by the OH group at the 3'-end of the nick, thereby sealing it, whereafter ligase and AMP are released. If the ligase detaches from the substrate before the 3' attack, e.g., because of premature AMP reloading of the enzyme, then the 5' AMP is left at the 5'-end, blocking further ligation attempts. In some instances, ATP is added at a concentration of about 1 μM, about 10 μM, about 100 μM, about 1000 μM, or about 10000 μM during the ligation reaction.

In some instances, cofactors that aid in ligation of the RTL probes are added during the ligation process. In some instances, the cofactors include magnesium ions ($Mg^{2+}$). In some instances, the cofactors include manganese ions ($Mn^{2+}$). In some instances, $Mg^{2+}$ is added in the form of $MgCl_2$. In some instances, $Mn^{2+}$ is added in the form of $MnCl_2$. In some instances, the concentration of $MgCl_2$ is at about 1 mM, at about 10 mM, at about 100 mM, or at about 1000 mM. In some instances, the concentration of MnCl2 is at about 1 mM, at about 10 mM, at about 100 mM, or at about 1000 mM.

In some instances, after ligation of the first and second RTL probes to generate a ligation product, the ligation product is released from the analyte. At this stage of the method, (1) the ligation product is hybridized to the analyte, and (2) the gDNA has been tagmented. To release the ligation product from the analyte, an endoribonuclease is used. An endoribonuclease such as RNAse H specifically cleaves RNA in RNA:DNA hybrids. Thus, not only does RNAse H cleave the hybridization of the ligation product to the analyte (releasing the ligation product), RNAse H also cleaves the undesirable RNA. In some instances, the ligation product is released enzymatically. In some instances, an endoribonuclease is used to release the ligation product from the analyte. In some instances, the endoribonuclease is one or more of RNase H. In some instances, the RNase H is RNase H1 or RNase H2.

In some instances, after generation of a ligation product from the RTL probes (e.g., a first RTL probe and second RTL probe), the biological sample is permeabilized. In some instances, permeabilization occurs using a protease. In some instances, the protease is an endopeptidase. Endopeptidases that can be used include but are not limited to trypsin, chymotrypsin, elastase, thermolysin, pepsin, clostripan, glutamyl endopeptidase (GluC), ArgC, peptidyl-asp endopeptidase (ApsN), endopeptidase LysC and endopeptidase LysN. In some instances, the endopeptidase is pepsin. In some instances, permeabilization is performed using proteinase K.

In some instances, the ligation product includes a capture probe binding domain, which can hybridize to a capture probe (e.g., a capture probe immobilized, directly or indirectly, on a substrate). In some instances, methods provided herein include contacting a biological sample with a substrate, wherein the capture probe is affixed to the substrate (e.g., immobilized to the substrate, directly or indirectly). In some instances, the capture probe includes a spatial barcode and the capture domain. In some instances, the capture probe binding domain of the ligation product binds (e.g., hybridizes) to the capture domain. After hybridization of the ligation product to the capture probe, the ligation product is extended at the 3' end to make a copy of the additional components (e.g., the spatial barcode) of the capture probe. In some instances, methods of ligation product capture as provided herein include permeabilization of the biological sample such that the capture probe can more easily hybridize to the ligation product (i.e., compared to no permeabilization). In some instances, reverse transcription (RT) reagents can be added to permeabilized biological samples. Incubation with the RT reagents provide for the extension of the capture probe using the ligation product as a template, as well as the extension of the ligation product using the capture probe as a template thereby producing nucleic acid molecules that comprise target analyte sequences, or complements thereof, and sequences of the capture probe, or complements thereof such as spatial barcodes, functional sequences, UMIs, etc.

The resulting nucleic acid molecule can be denatured from the capture probe template and transferred (e.g., to a clean tube) for amplification, and/or library construction as described herein. The spatially-barcoded, full-length nucleic acid molecule can be amplified via PCR prior to library construction. The nucleic acid molecule can then be enzymatically fragmented and size-selected in order to optimize the amplicon size. P5, P7, i7, and i5 can be used as sample indexes, and TruSeq Read 2 can be added via End Repair, A-tailing, Adaptor Ligation, and PCR. The fragments can then be sequenced using paired-end sequencing using TruSeq Read 1 and TruSeq Read 2 as sequencing primer sites.

Post-hybridization steps are also provided in Stahl P. L., et al., Visualization and analysis of gene expression in tissue sections by spatial transcriptomics *Science*, vol. 353, 6294, pp. 78-82 (2016), which in incorporated herein by reference).

In any of the methods described herein, the tissue sample is a formalin-fixed, paraffin-embedded (FFPE) tissue sample, a fresh tissue sample, or a frozen tissue sample. In some instances, the tissue sample is the FFPE tissue sample. In some instances, the biological sample is deparaffinized. Deparaffinization can be achieved using any method known in the art. For example, in some instances, the biological samples is treated with a series of washes that include xylene and various concentrations of ethanol. In some instances, methods of deparaffinization include treatment of xylene (e.g., three washes at 5 minutes each). In some instances, the methods further include treatment with ethanol (e.g., 100% ethanol, two washes 10 minutes each; 95% ethanol, two washes 10 minutes each; 70% ethanol, two washes 10 minutes each; 50% ethanol, two washes 10 minutes each). In some instances, after ethanol washes, the biological sample can be washed with deionized water (e.g., two washes for 5 minutes each). It is appreciated that one skilled in the art can adjust these methods to optimize deparaffinization.

In some instances, the biological sample is decrosslinked. In some instances, the biological sample is decrosslinked in a solution containing TE buffer (comprising Tris and EDTA). In some instances, the TE buffer is basic (e.g., at a pH of about 9). In some instances, decrosslinking occurs at about 50° C. to about 80° C. In some instances, decrosslinking occurs at about 70° C. In some instances, decrosslinking occurs for about 1 hour at 70° C. Just prior to decrosslinking, the biological sample can be treated with an acid (e.g., 0.1M HCl for about 1 minute). After the decrosslinking step, the biological sample can be washed (e.g., with 1× PBST).

Methods of Making a Protein A/G Transposome Complex

Protein A is a 40-60 kDA surface protein found in *Staphylococcus aureus* cell walls. Its ability to bind immunoglobulins and IgG proteins, the heavy chain within the Fc region of most immunoglobulins, from many mammalian species makes it a useful protein for complexing with antibodies. It has the ability to interact and associate with a number of antibodies to create multiple options for protein-transposome-antibody complexing. Protein G is an immunoglobulin binding protein found in *Streptococcal* bacteria, but differs from Protein A in its binding properties. Protein G is a cell surface binding protein of 40-65 kDa, that binds to the Gav and Fc region of multiple antibodies, and indeed it finds utility in purifying antibodies because of its wide ability for antibody binding. Associating either protein A, protein G, or a protein A/G fusion protein with the transposase to create a protein A/G-Tn5 transposome can include generating a contiguous nucleic acid sequence via, e.g., standard cloning techniques. Adapters to be inserted into the transposome are added by complexing the protein A/G transposase complex with the associated transposon sequences as known in the art.

For example, Kaya-Okur et al (2019, Nature Communications 10:1930 CUT&Tag for efficient epigenomic profiling of small samples and single cells (incorporated herein by reference), provides a method for generating a protein A-Tn5 transposome complex by first generating a C-terminal fusion protein with protein A separated from the transposase by a 26 amino acid long flexible peptide linker, followed by transposome generation with the generated protein A-transposase fusion protein complexed with the transposon mosaic ends. Another method for generating a protein A-Tn5 transposome complex can be found in Bartosovic et al (2021, Nat Biotech, doi.org/10.1038/s41587-021-00869-9, incorporated herein by reference). Commercially available protein A-Tn5 transposase complexes for generating a protein A fused transposomes are available, for example from Vazyme (Hyperactive pA-Tn5 Transposase for CUT&Tag).

The present disclosure is not limited by the methods in which a protein A or protein G-transposome complexes are generated, further the present disclosure is not limited by the methods of generating an antibody-transposome complex, where the antibody-transposome complex comprises an antibody bound to protein A or protein G of a protein A-transposome complex or a protein G-transposome complex.

Compositions and Kits

Also provided herein are compositions including capture probes, transposome complexes, tagmented DNA, splint oligonucleotides, and one or more polymerases. In some instances, a splint oligonucleotide is hybridized to the capture domain of a capture probe. In some instances, a splint oligonucleotide is hybridized to a transposon end sequence of fragmented (e.g., tagmented) genomic DNA. In some instances, a splint oligonucleotide is hybridized to the captured domain of a capture probe and a transposon end sequence of fragmented genomic DNA. In some instances, the composition comprises one or more transposon end sequences. In some instances, one or more transposon end sequences are ligated to the capture probe. In some instances, one or more transposon sequences are released from the fragmented DNA either before or after ligation of the fragmented genomic DNA to the capture probe. In some instances, the composition includes a ligase (e.g., T4 DNA ligase). In some instances, the composition includes a gap filling polymerase. In some instances, the composition includes a DNA polymerase.

In some instances, the capture domain of the capture probe binds the transposon end (e.g., without the facilitation by a splint oligonucleotide). In some instances, the composition includes a strand-displacing polymerase. In some instances, the composition includes a gap filling polymerase.

In some instances, the composition includes an array comprising a plurality of capture probes. In some instances, a capture probe of the plurality of capture probes include a spatial barcode and a capture domain.

In some instances, the composition includes a transposome. In some instances, the composition includes a protein binding protein-transposome complex. In some instance, the transposome complex includes a protein binding moiety, a transposase, a first transposon end sequence comprising a splint sequence that is substantially complementary to a portion of a splint oligonucleotide, and a second transposon end sequence.

Also provided herein are kits that include one or more reagents to detect one or more analytes described herein. In some instances, the kit includes an array comprising a plurality of capture probes comprising a spatial barcode and a capture domain. In some instances, the kit includes a transposome complex comprising an antibody, a transposase, a first transposon end sequence comprising a splint sequence that is substantially complementary to a portion of a splint oligonucleotide, and a second transposon end sequence comprising a functional sequence. In some instances, the kit includes a plurality of probes (e.g., RD probes, a first RTL probe, a second RTL probe, one or more spanning probes, and/or a third oligonucleotide).

A non-limiting example of a kit used to perform any of the methods described herein includes: (a) an array comprising a plurality of capture probes, wherein a capture probe of the plurality of capture probes comprises: (i) a spatial barcode and (ii) a capture domain; (b) a transposome complex comprising: (i) an antibody, (ii) a transposase, (iii) a first transposon end sequence comprising a splint sequence that is substantially complementary to a portion of a splint oligonucleotide, and (iv) a second transposon end sequence comprising a functional sequence; and (c) instructions for performing any one of the methods described herein.

In some instances of any of the kits described herein, the kit includes a second RTL probe that includes a preadenylated phosphate group at its 5' end and a first RTL probe comprising at least two ribonucleic acid bases at the 3' end.

qPCR and Analysis

Also provided herein are methods and materials for quantifying capture efficiency. In some instances, quantification of capture efficiency includes quantification of captured fragments (e.g., genomic DNA fragments, e.g., tagmented DNA fragments) from any of the spatial analysis methods described herein. In some instances, quantification includes PCR, qPCR, electrophoresis, capillary electrophoresis, fluorescence spectroscopy and/or UV spectrophotometry. In some instances, qPCR includes intercalating fluorescent dyes (e.g., SYBR green) and/or fluorescent labeled-probes (e.g., without limitation, Taqman probes or PrimeTime probes). In some instances, a NGS library quantification kit is used for quantification. For example, quantification can be performed using a KAPA library quantification kit (KAPA Biosystems), qPCR NGS Library Quantification Kit (Agilent), GeneRead Library Quant System (Qiagen), and/or PerfeCTa NGS Quantification Kit (Quantabio). In some instances that use qPCR for quantification, qPCR can include, without limitation, digital PCR, droplet digital (ddPCR), and ddPCR-Tail. In some instances that use electrophoresis for quantification, electrophoresis can include, without limitation, automated electrophoresis (e.g., TapeStation System, Agilent, and/or Bioanalzyer, Agilent) and capillary electrophoresis (e.g., Fragment Analyzer, Applied Biosystems). In some instances that use spectroscopy for quantification, the spectroscopy can include, without limitation, fluorescence spectroscopy (e.g., Qubit, Thermo Fisher). In some instances, NGS can be used to quantify capture efficiency.

In some instances, quantitative PCR (qPCR) is performed on the captured tagments. In some instances, the fragmented (e.g., tagmented) DNA is amplified, by any method described herein, before capture. For example, after capture of the fragmented DNA (e.g., tagmented DNA), ligation and strand displacement hybridization qPCR can be performed.

Methods of staining a biological sample (e.g., immunofluorescence, immunohistochemistry, H&E) are known in the art and are provided herein. In some instances, the biological sample can be imaged.

EXAMPLES

Example 1. Assessing Accessible Chromatin in a Spatial Context with a Transposome Complex Workflow An antibody binding moiety-transposome complex (FIG. 9) is constructed of a Tn5 dimerized transposase linked to a protein A or protein G. The Tn5 transposase is loaded with transposon sequences that contain 19-bp mosaic ends (ME), optionally capture domains, and primer sequences. The transposase and complexed transposons collectively form a transposome.

Figure 10:
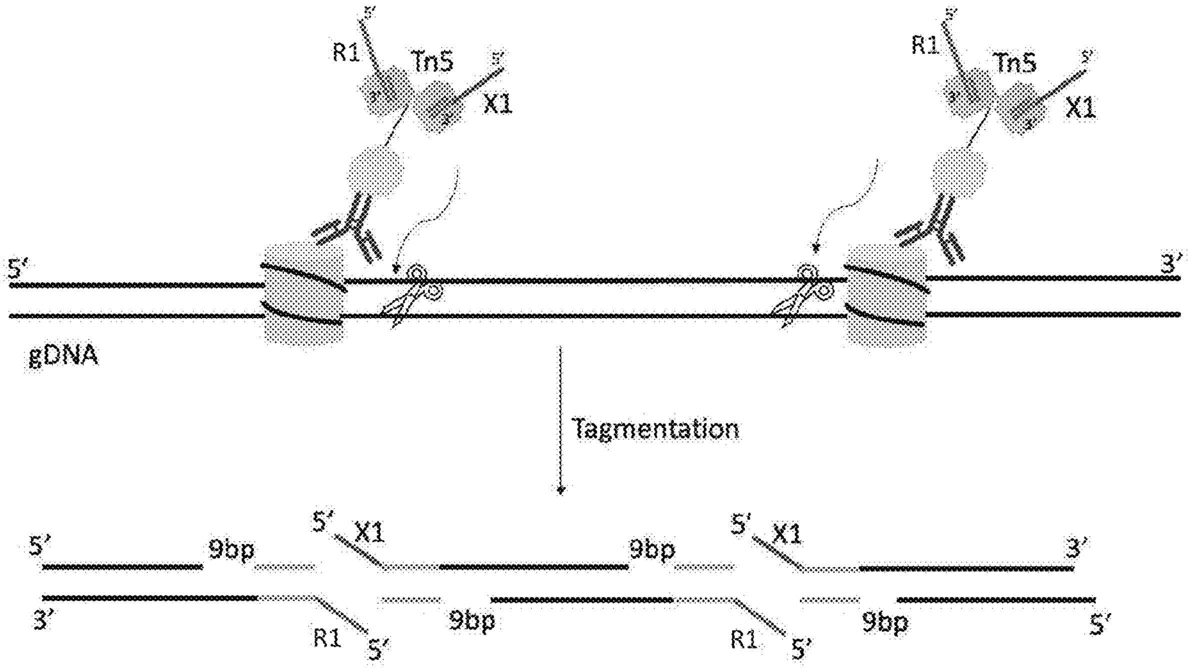
FIG. 10 shows an exemplary tagmentation step using a transposome complex bound to an antibody, which is in turn bound to its antigen site on an exemplary histone.

An antibody that binds, for example, a histone is applied to the biological sample and the antibody is allowed to bind to its target antigen, The transposome complex is applied to a biological sample which is located on a spatial array, and the protein A or protein G moiety binds to the antibody that is bound to the target protein (such as a histone). The genomic DNA, or open chromatin, of the cell of the tissue can undergo tagmentation, mediated by the transposome complex. The open chromatin or open genomic DNA that may be present between histones is available for a potential transpositional event as the transposase cuts the genomic DNA and inserts the transposon ends into the cut genomic DNA (FIG. 10). As such, the fragmented genomic DNA includes on either end one of the transposon end sequences (e.g., R1 or X1 related ends).

Figure 11:
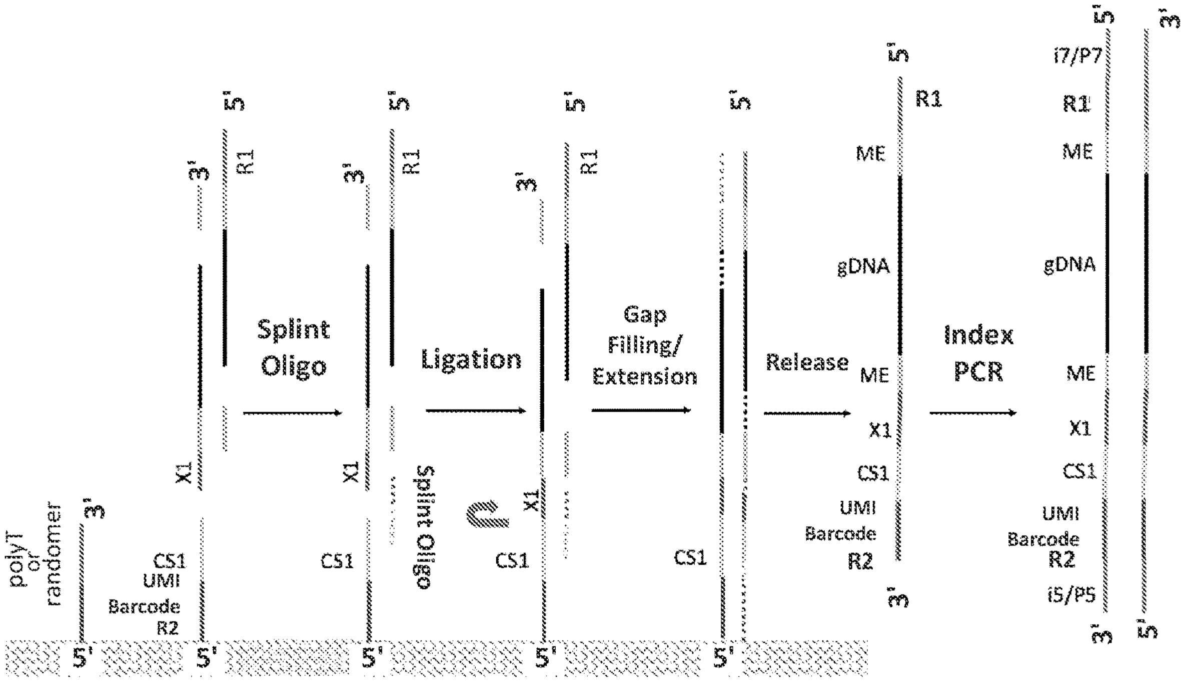
FIG. 11 shows an exemplary spatial assay for transposase accessible chromatin. UMI: universal molecular identifier: CS1: capture sequence 1.

The resulting tagmented gDNA in the biological sample can interact with capture probes on the spatial array, each capture probe having a capture domain and a spatial barcode, wherein the tagmented gDNA is attached to the capture probe using a splint oligonucleotide (FIG. 11). The resulting nucleic acid comprising the capture probe, splint oligonucleotide ("splint oligo" in FIG. 11), and tagmented gDNA are ligated and a gap-filling extension step to fill the gap between tagmented gDNA and the capture probe is performed, as well as gaps generated by the tagmentation process (e.g., at the 3' end of the capture domain). As a result, a primary strand attached to the capture probe and immobilized on the array is generated, the primary strand includes the capture probe and a sequence comprising the tagmented gDNA or a complement thereof. Attached to the primary strand is a second strand full-length product that is released by heating, and used e.g., as a PCR template. A library can be generated from the released product which can be sequenced and the spatial location of the sequenced product can be determined and correlated with a location in the biological tissue sample by determining all or part of the sequence of the spatial barcode on the capture probe and all or part of the tagmented gDNA sequence.

Example 2. Gap-Filling Between the Tagmented DNA and the Capture Probe

After the tagmented gDNA of Example 1 interacts with capture probes on the spatial array, with each capture probe having a capture domain and a spatial barcode, the tagmented gDNA is attached to the capture probe using a splint oligonucleotide (FIG. 11). The resulting nucleic acid comprising the capture probe, splint oligonucleotide ("splint oligo" in FIG. 11), and tagmented gDNA can have gaps, or spaces of non-ligated nucleic acids, between the end of one oligonucleotide and the beginning of another. For example, there may be a gap between the splint oligo and the X1 mosaic end, and/or between the X1 mosaic end and the gDNA.

The gaps can be filled, for example, by a "gap-filling" step which includes incorporation of one or more nucleic acids by a polymerase, based on the nucleic acid sequence of a template nucleic acid molecule, spanning a distance between the two nucleic acid molecules of interest, followed by ligation of the two now adjacent ends. As such, a non-interrupted nucleic acid is produced that contains at least the UMI, capture sequence, transposon sequences with mosaic ends, genomic DNA, another transposon sequence, and sequencing primer binding sites (FIG. 11).

Example 3. Assessing Accessible Chromatin in a Spatial Context with a Multi-Complex Workflow A multi-complex of a transposome, an antibody-binding moiety, and an antibody complex (FIG. 10) is constructed of a Tn5 transposome linked to a protein A or protein G, which is bound to an antibody that can bind, for example, histones. The Tn5 transposase is loaded with transposon sequences that contain 19-bp mosaic ends (ME) (e.g., transposome collectively), optionally capture domains, and primer sequences. The transposase, complexed transposons, and antibody is collectively referred to as a multi-complex.

The multi-complex with the antibody that binds, for example, a histone, is applied to the biological sample located on a spatial array. The antibody of the multi-complex binds to its target antigen, such as a target protein (e.g., histone). The genomic DNA, or open chromatin, of the cell of the biological sample, such as a tissue, can undergo tagmentation, mediated by the transposome of the multi-complex. The open chromatin or open genomic DNA that may be present between histones is available for a potential transpositional event as the transposase cuts the genomic DNA and inserts the transposon ends into the cut genomic DNA (FIG. 10). As such, the fragmented genomic DNA includes, on either end, transposon end sequences (e.g. R1 or X1 related ends).

The resulting tagmented gDNA in the biological sample can interact with capture probes on the spatial array, each capture probe having a capture domain and a spatial barcode, wherein the tagmented gDNA is attached to the capture probe using a splint oligonucleotide, as described in Example 1 (FIG. 11). A library can be generated from the released product which can be sequenced and the spatial location of the sequenced product can be determined and correlated with a location in the biological tissue sample by determining all or part of the sequence of the spatial barcode on the capture probe and all or part of the tagmented gDNA sequence.

Sequence Listing

```
SEQ ID NO: 1-Tn5 Transposase
MITSALHRAADWAKSVFSSAALGDPRRTARLVNVAAQLAKYSGKSITI
SSEGSEAMQEGAYRFIRNPNVSAEAIRKAGAMQTVKLAQEFPELLAIE
DTTSLSYRHQVAEELGKLGSIQDKSRGWWVHSVLLLEATTFRTVGLLH
QEWWMRPDDPADADEKESGKWLAAAATSRLRMGSMMSNVIAVCDREAD
IHAYLQDKLAHNERFVVRSKHPRKDVESGLYLYDHLKNQPELGGYQIS
IPQKGVVDKRGKRKNRPARKASLSLRSGRITLKQGNITLNAVLAEEIN
PPKGETPLKWLLLTSEPVESLAQALRVIDIYTHRWRIEEFHKAWKTGA
GAERQRMEEPDNLERMVSILSFVAVRLLQLRESETLPQALRAQGLLKE
AEHVESQSAETVLTPDECQLLGYLDKGKRKRKEKAGSLQWAYMAIARL
GGFMDSKRTGIASWGALWEGWEALQSKLDGFLAAKDLMAQGIKI

SEQ ID NO: 2-Tn5 Transposase (UniProtKB/Swiss-
Prot: Q46731.1)
MITSALHRAADWAKSVFSSAALGDPRRTARLVNVAAQLAKYSGKSITI
SSEGSEAMQEGAYRFIRNPNVSAEAIRKAGAMQTVKLAQEFPELLAIE
DTTSLSYRHQVAEELGKLGSIQDKSRGWWVHSVLLLEATTFRTVGLLH
QEWWMRPDDPADADEKESGKWLAAAATSRLRMGSMMSNVIAVCDREAD
IHAYLQDKLAHNERFVVRSKHPRKDVESGLYLYDHLKNQPELGGYQIS
IPQKGVVDKRGKRKNRPARKASLSLRSGRITLKQGNITLNAVLAEEIN
PPKGETPLKWLLLTSEPVESLAQALRVIDIYTHRWRIEEFHKAWKTGA
GAERQRMEEPDNLERMVSILSFVAVRLLQLRESFTLPQALRAQGLLKE
AEHVESQSAETVLTPDECQLLGYLDKGKRKRKEKAGSLQWAYMAIARL
GGFMDSKRTGIASWGALWEGWEALQSKLDGFLAAKDLMAQGIKI
```

What is claimed is:

1. A method for determining the location of accessible genomic DNA in a biological sample, the method comprising:

(a) providing the biological sample on an array comprising a plurality of capture probes, wherein a capture probe of the plurality of capture probes comprises: (i) a spatial barcode and (ii) a capture domain;

(b) binding an antibody specific to a chromatin protein in the biological sample to the chromatin protein;

(c) binding a transposome-antibody-binding moiety complex to the antibody, wherein the transposome-antibody-binding moiety complex comprises:

(i) a transposase, (ii) an antibody-binding moiety, (iii) a first transposon end sequence comprising a splint sequence, and (iv) a second transposon end sequence comprising a functional sequence; and (d) generating, by the transposase, fragmented genomic DNA comprising the first transposon end sequence and the second transposon end sequence;

(e) adding a plurality of splint oligonucleotides to the biological sample, wherein a portion of a splint oligonucleotide of the plurality of splint oligonucleotides hybridizes to a portion of the capture domain and another portion of the splint oligonucleotide hybridizes to the splint sequence of the fragmented genomic DNA;

(f) hybridizing the splint sequence of the fragmented genomic DNA to the splint oligonucleotide hybridized to the capture domain; and g) determining (i) the spatial barcode or a complement thereof, of the capture probe and (ii) all or part of a sequence of the fragmented genomic DNA, or a complement thereof, to determine the location of the accessible genomic DNA in the biological sample.

2. The method of claim 1, wherein steps (b) and (c) are performed at the same time, and wherein the antibody and the transposome-antibody-binding moiety complex are combined to form a multi-complex.

3. The method of claim 1, wherein the splint oligonucleotide comprises about 12 to about 40 nucleotides.

4. The method of claim 1, wherein steps (b) through (f) are performed at substantially the same time.

5. The method of claim 1, further comprising ligating the splint sequence of the fragmented genomic DNA to the capture domain of the capture probe.

6. The method of claim 1, further comprising performing gap filling and ligation between the 5' end of the first or second transposon end sequence and the 3' end of the fragmented genomic DNA.

7. The method of claim 6, further comprising extending a 3' end of the fragmented genomic DNA using the capture probe as a template, wherein the gap filling, ligation, and extension occur at substantially the same time.

8. The method of claim 1, wherein the functional sequence of the second transposon end sequence comprises a primer sequence.

9. The method of claim 1, wherein the antibody-binding moiety is protein A, protein G, or functional derivatives thereof.

10. The method of claim 1, wherein the transposase is a Tn5 transposase enzyme, a Mu transposase enzyme, a Tn7 transposase enzyme, a *vibhar* species transposase, or functional derivatives thereof.

11. The method of claim 1, further comprising extending a 3' end of the capture probe using the fragmented genomic DNA as a template, wherein the extending step is performed using a DNA polymerase having strand displacement activity.

12. The method of claim 1, further comprising staining the biological sample, optionally wherein the staining comprises hematoxylin and eosin (H&E) staining or immunofluorescence staining.

13. The method of claim 1, wherein the biological sample is permeabilized prior to step (b), wherein permeabilization is chemical or enzymatic.

14. The method of claim 13, wherein the enzymatic permeabilization comprises a protease selected from the group consisting of pepsin, collagenase, proteinase K, and combinations thereof.

15. The method of claim 1, wherein the biological sample is a fresh tissue sample or section, a frozen tissue sample or section, or a fixed tissue sample or section.

16. The method of claim 15, wherein the fixed tissue sample or section is a formalin-fixed, paraffin embedded (FFPE) tissue sample or section.

17. The method of claim 1, wherein the capture probe further comprises a cleavage domain, one or more functional domains, a unique molecular identifier, or combinations thereof.

18. The method of claim 1, further comprising determining the location of an mRNA in the biological sample by:

hybridizing the mRNA or a portion thereof to a capture domain of a second capture probe of the plurality of capture probes, wherein the second capture probe further comprises a spatial barcode; and determining (i) the spatial barcode or a complement thereof, of the second capture probe, and (ii) all or part of a sequence of the mRNA, or a complement thereof, and using the determined sequences of (i) and (ii) to determine the location of the mRNA in the biological sample.

19. The method of claim 18, wherein hybridizing the mRNA or a portion thereof to the capture domain is performed concurrent with or after step (b).

20. The method of claim 18, wherein determining (i) the spatial barcode or a complement thereof, and (ii) all or part of a sequence of the mRNA, or a complement thereof occurs concurrent with step (g).

21. The method of claim 18, wherein determining (i) the spatial barcode or a complement thereof, and (ii) all or part of a sequence of the mRNA, or a complement thereof comprises sequencing.

22. A method for determining the location of accessible genomic DNA in a biological sample, the method comprising:

(a) providing the biological sample on a first substrate;

(b) binding an antibody specific to a chromatin protein in the biological sample to the chromatin protein;

(c) binding a transposome-antibody-binding moiety complex to the antibody, wherein the transposome-antibody-binding moiety complex comprises:

(i) a transposase, (ii) an antibody-binding moiety, (iii) a first transposon end sequence comprising a splint sequence, and (iv) a second transposon end sequence comprising a functional sequence; and (d) generating, by the transposase, fragmented genomic DNA comprising the first transposon end sequence and the second transposon end sequence;

(e) aligning the first substrate with a second substrate comprising an array, such that at least a portion of the biological sample is aligned with at least a portion of the array, wherein the array comprises a plurality of capture probes, wherein a capture probe of the plurality of capture probes comprises: (i) a spatial barcode and (ii) a capture domain;

(f) adding a plurality of splint oligonucleotides to the biological sample, wherein a portion of a splint oligonucleotide of the plurality of splint oligonucleotides hybridizes to a portion of the capture domain and another portion of the splint oligonucleotide hybridizes to the splint sequence of the fragmented genomic DNA;

(g) hybridizing the splint sequence of the fragmented genomic DNA to the splint oligonucleotide hybridized to the capture domain; and (h) determining (i) the spatial barcode or a complement thereof, of the capture probe and (ii) all or part of a sequence of the fragmented genomic DNA, or a complement thereof, to determine the location of the accessible genomic DNA in the biological sample.

23. The method of claim 22, wherein the aligning comprises:

mounting the first substrate on a first member of a support device, the first member configured to retain the first substrate;

mounting the second substrate on a second member of the support device;

applying a reagent medium to the first substrate and/or the second substrate; and operating an alignment mechanism of the support device to move the first member and/or the second member such that at least a portion of the biological sample is aligned with at least a portion of the array, and such that the portion of the biological sample and the portion of the array contact the reagent medium.

24. The method of claim 23, wherein the reagent medium comprises a permeabilization agent selected from the group consisting of trypsin, pepsin, elastase, and proteinase K.

25. The method of claim 22, wherein at least one of the first substrate and the second substrate further comprises a spacer disposed on the first substrate or the second substrate, wherein when at least the portion of the biological sample is aligned with at least the portion of the array such that the portion of the biological sample and the portion of the array contact a reagent medium, the spacer is disposed between the first substrate and the second substrate and is configured to maintain the reagent medium within a chamber formed by the first substrate, the second substrate, and the spacer, and to maintain a separation distance between the first substrate and the second substrate, wherein the spacer is positioned to surround an area on the first substrate on which the biological sample is disposed and/or the array disposed on the second substrate, wherein the area of the first substrate, the spacer, and the second substrate at least partially encloses a volume comprising the biological sample.

26. The method of claim 22, wherein steps (b) and (c) are performed at the same time, and wherein the antibody and the transposome-antibody-binding moiety complex are combined to form a multi-complex.

27. The method of claim 22, wherein the transposase is a Tn5 transposase enzyme, a Mu transposase enzyme, a Tn7 transposase enzyme, a *vibhar* species transposase, or functional derivatives thereof.

28. The method of claim 1, wherein determining (i) the spatial barcode or a complement thereof, of the capture probe and (ii) all or part of a sequence of the fragmented genomic DNA, or a complement thereof, comprises sequencing.

29. The method of claim 13, wherein the chemical permeabilization comprises a detergent, optionally wherein the detergent is one or more of NP-40, polysorbate-20, and digitonin.

* * * * *

SEQUENCE LISTING

```
Sequence total quantity: 2
SEQ ID NO: 1             moltype = AA  length = 476
FEATURE                  Location/Qualifiers
source                   1..476
                         mol_type = protein
                         organism = synthetic construct
SEQUENCE: 1
MITSALHRAA DWAKSVFSSA ALGDPRRTAR LVNVAAQLAK YSGKSITISS EGSEAMQEGA  60
YRFIRNPNVS AEAIRKAGAM QTVKLAQEFP ELLAIEDTTS LSYRHQVAEE LGKLGSIQDK  120
SRGWWVHSVL LLEATTFRTV GLLHQEWWMR PDDPADADEK ESGKWLAAAA TSRLRMGSMM  180
SNVIAVCDRE ADIHAYLQDK LAHNERFVVR SKHPRKDVES GLYLYDHLKN QPELGGYQIS  240
IPQKGVVDKR GKRKNRPARK ASLSLRSGRI TLKQGNITLN AVLAEEINPP KGETPLKWLL  300
LTSEPVESLA QALRVIDIYT HRWRIEEFHK AWKTGAGAER QRMEEPDNLE RMVSILSFVA  360
VRLLQLRESF TLPQALRAQG LLKEAEHVES QSAETVLTPD ECQLLGYLDK GKRKRKEKAG  420
SLQWAYMAIA RLGGFMDSKR TGIASWGALW EGWEALQSKL DGFLAAKDLM AQGIKI      476

SEQ ID NO: 2             moltype = AA  length = 476
FEATURE                  Location/Qualifiers
source                   1..476
                         mol_type = protein
                         organism = synthetic construct
SEQUENCE: 2
MITSALHRAA DWAKSVFSSA ALGDPRRTAR LVNVAAQLAK YSGKSITISS EGSEAMQEGA  60
YRFIRNPNVS AEAIRKAGAM QTVKLAQEFP ELLAIEDTTS LSYRHQVAEE LGKLGSIQDK  120
SRGWWVHSVL LLEATTFRTV GLLHQEWWMR PDDPADADEK ESGKWLAAAA TSRLRMGSMM  180
SNVIAVCDRE ADIHAYLQDK LAHNERFVVR SKHPRKDVES GLYLYDHLKN QPELGGYQIS  240
IPQKGVVDKR GKRKNRPARK ASLSLRSGRI TLKQGNITLN AVLAEEINPP KGETPLKWLL  300
LTSEPVESLA QALRVIDIYT HRWRIEEFHK AWKTGAGAER QRMEEPDNLE RMVSILSFVA  360
VRLLQLRESF TLPQALRAQG LLKEAEHVES QSAETVLTPD ECQLLGYLDK GKRKRKEKAG  420
SLQWAYMAIA RLGGFMDSKR TGIASWGALW EGWEALQSKL DGFLAAKDLM AQGIKI      476
```